(12) United States Patent
Takemura et al.

(10) Patent No.: US 10,216,085 B2
(45) Date of Patent: Feb. 26, 2019

(54) TETRACARBOXYLIC ACID DIESTER COMPOUND, POLYIMIDE PRECURSOR POLYMER AND METHOD FOR PRODUCING THE SAME, NEGATIVE PHOTOSENSITIVE RESIN COMPOSITION, PATTERNING PROCESS, AND METHOD FOR FORMING CURED FILM

(71) Applicant: SHIN-ETSU CHEMICAL CO., LTD., Tokyo (JP)

(72) Inventors: Katsuya Takemura, Jyoetsu (JP); Hiroyuki Urano, Jyoetsu (JP); Masashi Iio, Jyoetsu (JP); Masayoshi Sagehashi, Jyoetsu (JP); Koji Hasegawa, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/616,237

(22) Filed: Jun. 7, 2017

(65) Prior Publication Data

US 2018/0024434 A1    Jan. 25, 2018

(30) Foreign Application Priority Data

Jul. 25, 2016    (JP) .................................. 2016-145802

(51) Int. Cl.
| | | |
|---|---|---|
| *G03F 7/16* | (2006.01) | |
| *G03F 7/20* | (2006.01) | |
| *G03F 7/32* | (2006.01) | |
| *G03F 7/38* | (2006.01) | |
| *G03F 7/40* | (2006.01) | |
| *C07C 69/76* | (2006.01) | |
| *C07C 69/80* | (2006.01) | |
| *C08G 73/10* | (2006.01) | |
| *C08G 73/12* | (2006.01) | |
| *G03F 7/004* | (2006.01) | |
| *G03F 7/031* | (2006.01) | |

(Continued)

(52) U.S. Cl.
CPC ............ *G03F 7/0387* (2013.01); *C07C 69/76* (2013.01); *C07C 69/80* (2013.01); *C08G 73/1007* (2013.01); *C08G 73/1042* (2013.01); *C08G 73/121* (2013.01); *C08G 73/123* (2013.01); *C08G 73/127* (2013.01); *G03F 7/0045* (2013.01); *G03F 7/0046* (2013.01); *G03F 7/031* (2013.01); *G03F 7/037* (2013.01); *G03F 7/038* (2013.01); *G03F 7/0385* (2013.01); *G03F 7/0388* (2013.01); *G03F 7/162* (2013.01); *G03F 7/168* (2013.01); *G03F 7/2004* (2013.01); *G03F 7/325* (2013.01); *G03F 7/38* (2013.01); *G03F 7/40* (2013.01)

(58) Field of Classification Search
CPC . G03F 7/0387; C08G 73/1042; C08G 73/121; C08G 73/1007; C08G 73/123; C08G 73/127; C07C 69/80
See application file for complete search history.

(56) References Cited

U.S. PATENT DOCUMENTS 3,819,666 A    6/1974 Kleiner et al.
3,957,512 A    5/1976 Kleeberg et al.
(Continued)

FOREIGN PATENT DOCUMENTS

EP    0 532 183 A2 *   8/1992    ........... G03F 7/0387
EP    1013650 A2    6/2000
(Continued)

OTHER PUBLICATIONS

English translation of JP, 3035672 B2 (2000) from machine translation from AIPN Japan Patent Office National Center for Industrial Property Information and Training, generated Dec. 29, 2017, 9 pages.*

(Continued)

*Primary Examiner* — Cynthia Hamilton
(74) *Attorney, Agent, or Firm* — Oliff PLC

(57) ABSTRACT

The present invention provides a tetracarboxylic acid diester compound shown by the following general formula (1), $$\text{(1)}$$

[Structural formula showing: HO-C(=O)-X_1-C(=O)-OH with R_1-O-C(=O) and C(=O)-O-R_1 groups attached to X_1]

wherein $X_1$ represents a tetravalent organic group; and $R_1$ represents a group shown by the following general formula (2), $$-(Y_1)_n-(Rf)_k \quad (2)$$

wherein the dotted line represents a bond; $Y_1$ represents an organic group with a valency of k+1; Rf represents a linear, branched, or cyclic alkyl group having 1 to 20 carbon atoms or an aromatic group in which a part or all of hydrogen atoms is/are substituted with a fluorine atom(s); "k" represents 1, 2, or 3; and "n" represents 0 or 1. There can be provided a tetracarboxylic acid diester compound that can give a polyimide precursor polymer soluble in a safe organic solvent widely used as a solvent of a composition, and usable as a base resin of a negative photosensitive resin composition.

8 Claims, No Drawings

(51) Int. Cl.
*G03F 7/037* (2006.01)
*G03F 7/038* (2006.01)

(56) References Cited

U.S. PATENT DOCUMENTS

| | | | | |
|---|---|---|---|---|
| 4,435,294 | A * | 3/1984 | Oxenrider | D06M 13/213 252/8.62 |
| 4,647,284 | A * | 3/1987 | Karydas | C07C 317/00 252/8.62 |
| 4,897,461 | A * | 1/1990 | Uekita | C08G 73/10 525/436 |
| 6,001,534 | A | 12/1999 | Kato | |
| 2002/0037991 | A1 | 3/2002 | Arai et al. | |
| 2017/0298186 | A1* | 10/2017 | Takemura | C07C 69/92 |

FOREIGN PATENT DOCUMENTS

| | | |
|---|---|---|
| JP | S49-115541 A | 11/1974 |
| JP | S55-45746 A | 3/1980 |
| JP | 3035672 b2 * | 3/2000 |
| JP | 2000-281671 A | 10/2000 |
| JP | 3232022 B2 | 11/2001 |
| JP | 2005-049504 A | 2/2005 |
| JP | 3627488 B2 | 3/2005 |
| JP | 5417623 B2 | 2/2014 |
| WO | 2013/168675 A1 | 11/2013 |

OTHER PUBLICATIONS

Dec. 22, 2017 extended European Search Report issued in Application No. 17001064.9.
Dennis P. Curran et al., "Synthesis and Reactions of Fluorous Carbonzyloxy (Fcbz) Derivatives of α-Amino Acids", J. Org. Chem., 2003, 68, 4643-4647.
Dale L. Boger, et al., "Identification of a Novel Class of Small-Molecule Antiangiogenic Agents through the Screening of Combinatorial Libraries Which Function by Inhibiting the Binding and Localization of Proteinase MMP2 to Integrin αvβ3", J. Am. Chem. Soc. 2001, 123, 120-1288.
Sep. 5, 2018 Office Action issued in Korean Application No. 10-2017-0093292.

* cited by examiner ents. However, Patent Document 3 fails to specifically describe the resolution capacity in patterning.

TETRACARBOXYLIC ACID DIESTER COMPOUND, POLYIMIDE PRECURSOR POLYMER AND METHOD FOR PRODUCING THE SAME, NEGATIVE PHOTOSENSITIVE RESIN COMPOSITION, PATTERNING PROCESS, AND METHOD FOR FORMING CURED FILM

BACKGROUND OF THE INVENTION

Field of the Invention

The present invention relates to a tetracarboxylic acid diester compound useful as a structural unit of a polyimide precursor polymer, a polyimide precursor polymer obtained by using the tetracarboxylic acid diester compound, a method for producing the same, a negative photosensitive resin composition using the polyimide precursor polymer as a base resin, a patterning process using the negative photosensitive resin composition, and a method for forming a cured film.

Description of the Related Art

As various electronic devices including a personal computer, a digital camera, and a mobile phone progress toward downsizing and higher performance, requirements are rapidly increasing for further downsizing, thinning, and densifying in semiconductor devices. It is thus desired to develop a photosensitive insulating material that can accommodate an increase in surface area of a substrate for the sake of higher productivity and can form a fine pattern with high aspect ratio on a substrate, in high density mounting technologies including chip size package or chip scale package (CSP) and three-dimensional lamination.

As the photosensitive insulating material capable of forming a pattern on a substrate in the high density mounting technology including three-dimensional lamination, a polyimide film has been used for a top coat or an insulator layer. The polyimide film has attracted attention because of its insulating property, mechanical strength, and adhesiveness to a substrate, and has been still actively developed.

Conventional examples of the photosensitive polyimide material include materials using polyamic acid, which is a precursor of polyimide. For example, there are proposed materials in which a photosensitive group is introduced into a carboxyl group of polyamic acid by an ester bond (Patent Documents 1 and 2). However, these proposed materials require imidization treatment at a high temperature exceeding 300° C. after forming a patterned film to obtain an intended polyimide film. Thus, these materials need to restrict a base substrate and oxidize a copper wiring in order to withstand the high temperature.

To solve such problems, there are proposed photosensitive polyimides using a solvent-soluble resin that has been already imidized to lower the temperature for post-curing (Patent Documents 3 and 4). A negative photosensitive resin composition containing the polyimide described in Patent Document 3 uses N-methyl-2-pyrrolidone (NMP) for development in patterning. However, Patent Document 3 fails to specifically describe the resolution capacity in patterning.

On the other hand, a photosensitive resin composition proposed in Patent Document 4 uses a base resin that has been already imidized for curing at low temperature. This composition contains cyclopentanone as a solvent and utilizes an alkaline aqueous solution for development process. However, its resolution capacity still should be improved.

More specifically, patterning using the photosensitive resin composition described in Patent Document 4 is performed with an ultrathin film, and the size of a resolved pattern is large. This insufficient resolution capacity is due to a polyimide resin used as the base resin disclosed in Patent Document 4, which has poor solubility in an alkaline aqueous solution used as the developer. Increasing the solubility in a developer is important for improving the resolution capacity in patterning.

In practice, with respect to the resolution capacity of the photosensitive insulating material recently required in the high density mounting technology including three-dimensional lamination, a pattern to be formed requires an aspect ratio (final film thickness (or pattern height)/pattern dimension) of 1 or more, or about 2. In other words, when a desired final film thickness or pattern height is 10 μm, a pattern must be formed with a dimension of 10 μm or less, or about 5 μm.

Besides, Patent Document 5 describes a patterning process using a photosensitive resin composition that contains a material utilizing polyamic acid, which is a precursor of polyimide, for example, a resin in which an ester bond is introduced into a carboxyl group of polyamic acid. In some examples of this patterning process, a formed film is baked at a relatively low temperature of 250° C. to obtain an intended polyimide film. This development process uses N-methyl-2-pyrrolidone as an organic solvent, but this patent document fails to specifically disclose the resolution capacity.

Patent Document 6 refers to patterning of a negative photosensitive resin composition using a polyimide precursor. The patterning of this photosensitive resin composition uses cyclopentanone for development. This patent document discloses about the resolution capacity, specifically, that an aspect ratio of 1 or more can be achieved. However, this aspect ratio is not a ratio of final film thickness or pattern height to pattern dimension, but a ratio of film thickness to dimension after coating and drying. Thus, this resolution capacity is not a practical value and should be improved. Moreover, although the use of cyclopentanone, which is an organic solvent widely used, as the developer is preferred, the use of an organic solvent sometimes easily causes overhang profile just after development due to swelling of the film during the development.

Furthermore, Patent Document 7 refers to patterning of a negative photosensitive resin composition using a polyimide precursor. The patterning of this photosensitive resin composition uses an alkaline aqueous solution as a developer. In the patterning process, solubility in the alkaline developer is improved by incorporating acidic groups, i.e., alkali-soluble groups such as carboxyl groups into the resin of the polyimide precursor, and a pattern is formed by development with an alkaline aqueous solution. The development with an alkaline aqueous solution is difficult to cause swelling and can improve the pattern profile and the resolution capacity. However, when the alkali-soluble groups, which allow the development with an alkaline aqueous solution, are incorporated into the resin, although the resolution is improved, the resin after curing cannot withstand a removing liquid having an extremely strong alkalinity, which is used for removing a resist pattern for plating in a step of forming a metal wiring. This problem still remain unsolved. To form an excellent insulating top coat, the alkali-soluble groups in the resin require completely sealing or completely removing from the system.

As mentioned above, the pattern miniaturization in rewiring technology of an insulating top coat is expected to progress more and more in future with the increase of density and integration of chips. It is thus strongly desired to develop a photosensitive resin composition using a polymer having a polyimide precursor structural unit that can achieve high resolution while maintaining excellent properties such as mechanical strength and adhesiveness of a pattern and a top coat of polyimide obtained by baking.

It is also strongly desired that the insulating top coat after patterning and curing has resistance to heat in various steps and resistance to various chemicals.

In summary, it is desired to rapidly develop the photosensitive resin composition having all of the above properties without lack.

PRIOR ART DOCUMENTS

Patent Documents

Patent Document 1: Japanese Unexamined Patent Application Publication No. S49-115541
Patent Document 2: Japanese Unexamined Patent Application Publication No. S55-45746
Patent Document 3: Japanese Patent No. 3232022
Patent Document 4: Japanese Patent No. 5417623
Patent Document 5: Japanese Unexamined Patent Application Publication No. 2005-49504
Patent Document 6: WO2013/168675
Patent Document 7: Japanese Patent No. 3627488

SUMMARY OF THE INVENTION

The present invention was accomplished in view of the above-described circumstances. It is an object of the present invention to provide a tetracarboxylic acid diester compound that can give a polyimide precursor polymer usable as a base resin of a negative photosensitive resin composition capable of forming a fine pattern with high resolution; a polyimide precursor polymer obtained by using the tetracarboxylic acid diester compound; and a method for producing the same.

Another object of the present invention is to provide a negative photosensitive resin composition using as a base resin a polyimide precursor polymer that can improve the resolution by increasing the dissolution rate difference between an unexposed part (a part to be dissolved in a developer) given by high solubility in an organic solvent developer and an exposed part (a part to be insolubilized in a developer by crosslinking reaction, photo-polymerization, etc.) of a negative pattern, i.e. the dissolution contrast, and can improve the resolution without deteriorating the pattern profile due to swelling or the like at development with an organic solvent in patterning, and to provide a negative photosensitive resin composition that can utilize a widely used safe organic solvent at the organic solvent development.

To achieve this object, the present invention provides a tetracarboxylic acid diester compound shown by the following general formula (1), $$\text{HO-CO-X}_1\text{-CO-OH} \qquad R_1\text{-O-CO-X}_1\text{-CO-O-}R_1 \tag{1}$$

wherein $X_1$ represents a tetravalent organic group; and $R_1$ represents a group shown by the following general formula (2), $$-(Y_1)_n-(Rf)_k \tag{2}$$

wherein the dotted line represents a bond; $Y_1$ represents an organic group with a valency of k+1; Rf represents a linear, branched, or cyclic alkyl group having 1 to 20 carbon atoms or an aromatic group in which a part or all of hydrogen atoms is/are substituted with a fluorine atom(s); "k" represents 1, 2, or 3; and "n" represents 0 or 1.

This tetracarboxylic acid diester compound can give a polyimide precursor polymer usable as a base resin of a negative photosensitive resin composition that can increase the solubility and prevent swelling at the organic solvent development in patterning.

In the compound, $Y_1$ in the general formula (2) is preferably a linear or branched divalent organic group having 1 to 6 carbon atoms.

This compound sufficiently exhibits the effect of the present invention.

In the compound, $R_1$ in the general formula (1) is preferably an organic group selected from groups shown by the following general formulae (3), (4), (5), and (6), $$-(\underset{Rb}{\underset{|}{\overset{Ra}{\overset{|}{C}}}})_{n1}-Rf \tag{3}$$

$$-(Y_2-O)_{n2}-(CH_2)_{n3}-Rf \tag{4}$$

$$-(Y_3-O)_{n4}-\underset{O}{\overset{\overset{\displaystyle \|}{C}}{}}-(CH_2)_{n5}-Rf \tag{5}$$

$$\cdots\underset{\underset{n6}{}}{\overset{OH}{\underset{|}{\bigwedge}}}-O-(CH_2)_{n7}-Rf \tag{6}$$

wherein the dotted line represents a bond; Rf is as defined above; Ra and Rb represent a hydrogen atom or an alkyl group having 1 to 3 carbon atoms; $Y_2$ and $Y_3$ represent a linear or branched alkylene group having 1 to 6 carbon atoms; n1 represents an integer of 0 to 6; n2 represents an integer of 1 to 6; n3 represents an integer of 0 to 6; n4 represents an integer of 1 to 6; n5 represents an integer of 0 to 6; n6 represents 0 or 1; and n7 represents an integer of 0 to 6.

$R_1$ is preferably the above group since a compound used as a raw material for introducing $R_1$ is available.

$R_1$ in the general formula (1) is still more preferably a group shown by the following general formula (3-1), $$-CH_2-CH_2-Rf \tag{3-1}$$

wherein the dotted line represents a bond; and Rf is as defined above.

Such a group enables stabilization since the fluorine-substituted alkyl group is separated from the ester portion.

Furthermore, the present invention provides a polyimide precursor polymer comprising a structural unit shown by the following general formula (7),

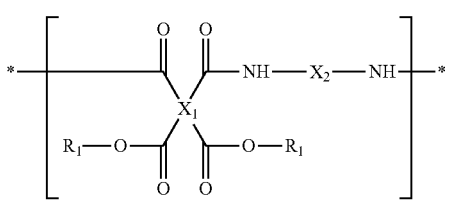

(7)

wherein $X_1$ represents a tetravalent organic group; $X_2$ represents a divalent organic group; and $R_1$ represents a group shown by the following general formula (2),

(2)

wherein the dotted line represents a bond; $Y_1$ represents an organic group with a valency of k+1; Rf represents a linear, branched, or cyclic alkyl group having 1 to 20 carbon atoms or an aromatic group in which a part or all of hydrogen atoms is/are substituted with a fluorine atom(s); "k" represents 1, 2, or 3; and "n" represents 0 or 1.

The polyimide precursor polymer having the structural unit shown by the general formula (7) can be derived from the tetracarboxylic acid diester compound shown by the general formula (1). The tetracarboxylic acid diester compound shown by the general formula (1) contains an organic group $R_1$ shown by the general formula (2) (for example, an organic group selected from groups shown by the formulae (3) to (6)), which contains a linear, branched, or cyclic alkyl group having 1 to 20 carbon atoms (for example, a perfluoroalkyl group) or an aromatic group in which a part or all of hydrogen atoms is/are substituted with a fluorine atom(s). Generally, most polymers having a polyimide precursor structural unit are soluble only in a polar solvent such as N-methyl-2-pyrrolidone. However, the polyimide precursor structural unit shown by the general formula (7) derived from the tetracarboxylic acid diester compound shown by the general formula (1), which incorporates an Rf group such as a perfluoroalkyl group into a substituent terminal of the polymer, allows the polymer to easily dissolve in a widely used organic solvent, to significantly increase the solubility in the widely used organic solvent, and to form a negative photosensitive resin composition with improved resolution.

Moreover, the polyimide precursor polymer having the structural unit shown by the general formula (7) contains the organic group $R_1$ shown by the general formula (2) (for example, an organic group selected from groups shown by the formulae (3) to (6)), which contains the Rf group such as a perfluoroalkyl group at a substituent terminal. This structure prevents a film formed by using this polymer, or a film formed by using a composition containing this polymer from swelling when the film is dissolved in an organic solvent.

The above polyimide precursor polymer preferably further comprises a structural unit shown by the following general formula (8),

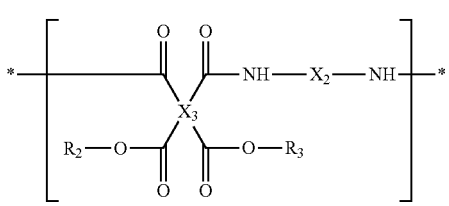

(8)

wherein $X_2$ is as defined above; $X_3$ represents a tetravalent organic group that is the same as or different from $X_1$; and $R_2$ and $R_3$ independently represent a hydrogen atom, a linear, branched, or cyclic alkyl group having 1 to 6 carbon atoms, or an organic group shown by the following general formula (9), provided that at least one of $R_2$ and $R_3$ is an organic group shown by the general formula (9),

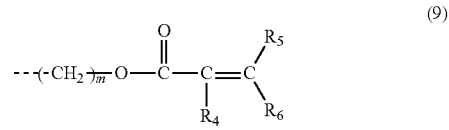

(9)

wherein the dotted line represents a bond; $R_4$ represents a hydrogen atom or an organic group having 1 to 3 carbon atoms; $R_5$ and $R_6$ independently represent a hydrogen atom or an organic group having 1 to 3 carbon atoms; and "m" represents an integer of 2 to 10.

This polymer has a polymerizable unsaturated linking group in its structural unit. Thus, when this polymer is combined with a later-described photo radical initiator, radical polymerization progresses by radicals generated at an exposed part in patterning as an initiator, and the polymer is insolubilized in a developer. This allows the polymer to form a negative photosensitive resin composition without an additional crosslinking agent.

Furthermore, the present invention provides a method for producing the above polyimide precursor polymer, comprising reacting a tetracarboxylic acid diester compound shown by the following general formula (1) with a diamine shown by the following general formula (10),

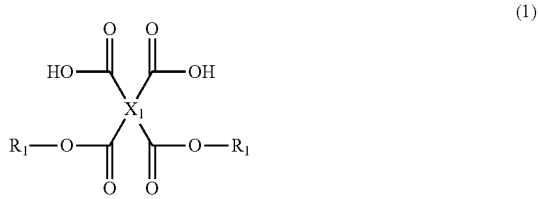

(1)

wherein $X_1$ and $R_1$ are as defined above,

(10)

wherein $X_2$ is as defined above.

The polyimide precursor polymer having the structural unit shown by the general formula (7) can be produced, for example, by the above method.

Furthermore, the present invention provides a method for producing the above polyimide precursor polymer, comprising reacting a tetracarboxylic acid diester compound shown by the following general formula (1) with a diamine shown by the following general formula (10) and a tetracarboxylic acid diester compound shown by the following general formula (11),

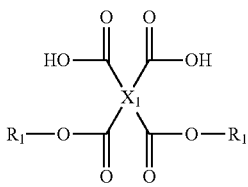
(1)

wherein $X_1$ and $R_1$ are as defined above, $$H_2N-X_2-NH_2 \quad (10)$$

wherein $X_2$ is as defined above,

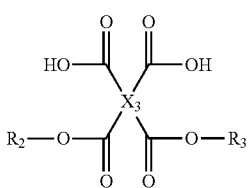
(11)

wherein $X_3$, $R_2$, and $R_3$ are as defined above.

The polyimide precursor polymer having the structural unit shown by the general formula (8) can be produced, for example, by the above method.

Furthermore, the present invention provides a negative photosensitive resin composition comprising:

(A) the polyimide precursor polymer having the structural unit shown by the general formula (8);

(B) a photo-radical initiator; and (D) a solvent.

As mentioned above, the polyimide precursor polymer having the structural unit shown by the general formula (8) has a polymerizable unsaturated linking group in its molecule. Thus, a negative photosensitive resin composition can be obtained by combining this polymer with a photo-radical initiator.

Furthermore, the present invention provides a negative photosensitive resin composition comprising:

(A') the above polyimide precursor polymer;

(B) a photo-radical initiator;

(C) a crosslinking agent having two or more photo-polymerizable unsaturated linking groups per molecule; and (D) a solvent.

In this composition, the polyimide precursor polymer that contains no structural unit shown by the general formula (8) can be a polymer having no polymerizable or crosslinkable structure in its molecule. In this case, a negative composition can be formed by adding a crosslinking agent having photo-polymerizable unsaturated linking groups. On the other hand, the polyimide precursor polymer having the structural unit shown by the general formula (8) already has a polymerizable unsaturated linking group in its molecule, but an additional crosslinking agent may be added.

Furthermore, the present invention provides a negative photosensitive resin composition comprising:

(A') the above polyimide precursor polymer;

(B') a photo acid generator;

(C') one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms having a glycidyl group as shown by the following formula (C-2),

(C-1)

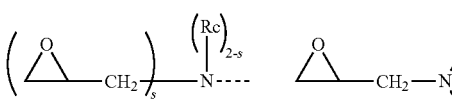
(C-2)

wherein the dotted line represents a bond, Rc represents a linear, branched, or cyclic alkyl group having 1 to 6 carbon atoms, and "s" represents 1 or 2; and (D) a solvent.

Use of the photo acid generator of component (B') generates an acid at an exposed part in patterning, thereby crosslinking between crosslinking groups of the added crosslinking agent of component (C') and crosslinking reaction points of the polymer. This makes the exposed part insoluble in a developer, providing the composition capable of forming a negative image.

Furthermore, the present invention provides a patterning process comprising:

(1) applying the above negative photosensitive resin composition onto a substrate to form a photosensitive material film;

(2) exposing the photosensitive material film to a high energy beam having a wavelength of 190 to 500 nm or an electron beam via a photomask after a heat treatment; and (3) performing development with a developer of an organic solvent.

The polyimide precursor polymer used as the base resin of the inventive negative photosensitive resin composition contains the structural unit shown by the general formula (7) and thus an Rf group such as a perfluoroalkyl group at a substituent terminal. The existence of the Rf group increases the solubility in an organic solvent developer and can prevent concerns of swelling. Moreover, this patterning process is especially suitable for a negative photosensitive resin composition using a polymer having a polymerizable unsaturated linking group as a base resin.

The patterning process preferably further comprises performing post-exposure bake between the exposing step and the development step.

In particular, when the negative photosensitive resin composition containing the polyimide precursor polymer having the structural unit shown by the general formula (8) is used, the post-exposure bake (PEB) step can promote crosslinking reaction between crosslinking groups of the crosslinking agent and crosslinking reaction points of the polymer by using an acid generated from the photo acid generator during exposure as a catalyst.

Furthermore, the present invention provides a method for forming a cured film, comprising baking a film having a pattern formed by the above patterning process at 100 to 300° C. and post-curing the film.

The inventive polyimide precursor polymer contains an Rf group such as a perfluoroalkyl group at a substituent terminal. However, the polyimide precursor structural unit in this polyimide precursor polymer causes imide ring-closure reaction in the post-curing step, consequently eliminating and removing the Rf group such as a perfluoroalkyl group from the system. Thus, the cured film after post-curing becomes a very stable polyimide resin film. This cured film has an extremely improved resistance to chemical agents, especially, a removing liquid having an extremely strong alkalinity, which is used for removing a resist pattern for plating in a step of forming a metal wiring. Such a cured film with a pattern can serve as an excellent top coat for protecting electric and electronic parts or an excellent insulating top coat.

The present invention can provide a tetracarboxylic acid diester compound that can give a polyimide precursor polymer usable as a base resin of a negative photosensitive resin composition of an organic solvent development type. When a negative photosensitive resin composition containing a polyimide precursor polymer obtained from the tetracarboxylic acid diester compound is used for a patterning process, a widely used safe organic solvent can be used for the development, the solubility in this developer is sufficiently increased, and thus the resolution can be improved. Furthermore, since swelling can be prevented during the development, a fine pattern with a good profile can be obtained.

Furthermore, according to the present invention, when the obtained film having a pattern is post-cured, the high-solubility function with respect to an organic solvent, which has effectively served to improve the resolution in patterning, is removed from the system by imide ring-closure reaction, providing a stable polyimide film. Thus, the present invention can provide a cured film having excellent chemical resistance. Moreover, the obtained film can serve as a top coat excellent in mechanical strength, substrate adhesiveness, electric characteristics, and reliability, which are characteristic of polyimide.

DETAILED DESCRIPTION OF THE PREFERRED EMBODIMENTS

As mentioned above, it is desired to develop a tetracarboxylic acid diester compound capable of providing a polyimide precursor polymer usable as a base resin of a negative photosensitive resin composition that allows the development with a widely used safe organic solvent, sufficiently increases the solubility in this developer, and thus can improve the resolution, enabling a fine pattern to be formed.

The present inventors have earnestly investigated to achieve the above object and consequently found the following: a polymer (a polyimide precursor polymer) having a polyimide precursor structural unit obtained from a tetracarboxylic acid diester compound shown by the general formula (1) is useful as a base resin of a composition since this polymer can easily dissolve in a widely used safe organic solvent. This polymer is usable in a negative photosensitive resin composition available for the organic solvent development. A pattern obtained by using this negative photosensitive resin composition is fine and has good pattern profile. In addition, as mentioned above, since the polymer having the polyimide precursor structural unit obtained from the tetracarboxylic acid diester compound shown by the general formula (1) can easily dissolve in a widely used safe organic solvent, the widely used safe organic solvent can be advantageously used for the organic solvent development.

Furthermore, a top coat obtained by patterning and baking of a negative photosensitive resin composition containing the polymer having the polyimide precursor structural unit as a base resin has excellent mechanical strength and adhesiveness. In other words, a cured film having a pattern formed by the negative photosensitive resin composition containing the polymer having the polyimide precursor structural unit as a base resin can serve as an excellent top coat for protecting electric and electronic parts or an excellent insulating top coat. The present invention was brought to completion from these findings.

That is, the present invention is a tetracarboxylic acid diester compound shown by the following general formula (1),

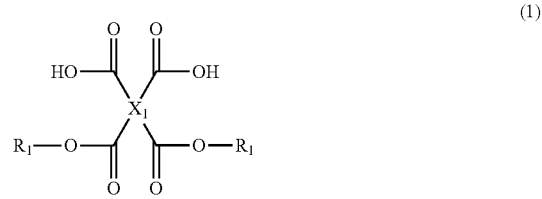

wherein $X_1$ represents a tetravalent organic group; and $R_1$ represents a group shown by the following general formula (2),

wherein the dotted line represents a bond; $Y_1$ represents an organic group with a valency of k+1; Rf represents a linear, branched, or cyclic alkyl group having 1 to 20 carbon atoms or an aromatic group in which a part or all of hydrogen atoms is/are substituted with a fluorine atom(s); "k" represents 1, 2, or 3; and "n" represents 0 or 1.

Hereinafter, the present invention will be described in detail, but the present invention is not limited thereto.

[Tetracarboxylic Acid Diester Compound]

The inventive tetracarboxylic acid diester compound is shown by the following general formula (1),

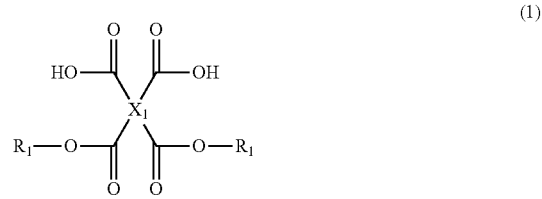

wherein $X_1$ represents a tetravalent organic group; and $R_1$ represents a group shown by the following general formula (2),

wherein the dotted line represents a bond; $Y_1$ represents an organic group with a valency of k+1; Rf represents a linear, branched, or cyclic alkyl group having 1 to 20 carbon atoms or an aromatic group in which a part or all of hydrogen atoms is/are substituted with a fluorine atom(s); "k" represents 1, 2, or 3; and "n" represents 0 or 1.

$X_1$ in the general formula (1) represents a tetravalent organic group and is not limited to particular tetravalent organic groups. $X_1$ is preferably a tetravalent organic group of an alicyclic aliphatic group having 4 to 40 carbon atoms or an aromatic group, more preferably a tetravalent organic group shown by the following formula (12). The structure of $X_1$ may be one kind or a combination of two or more kinds.

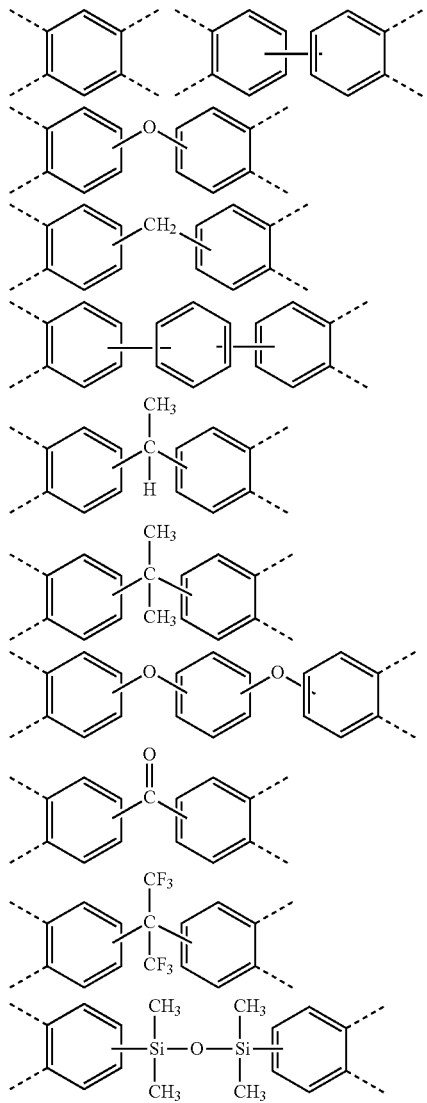

(12)

wherein the dotted line represents a bond.

Additionally, $Y_1$ in the general formula (2) is preferably a linear or branched divalent organic group (for example, an alkylene group) having 1 to 6 carbon atoms.

Additionally, $R_1$ in the general formula (1) is preferably an organic group selected from groups shown by the following general formulae (3), (4), (5), and (6), $$--\!\!\!-\underset{\underset{Rb}{|}}{\overset{\overset{Ra}{|}}{C}}\!\!\!\!\!\!-_{\overline{n1}}Rf \quad (3)$$

$$-\!\!\!-\!(Y_2\!\!-\!\!O\,)_{\overline{n2}}\!(CH_2\,)_{\overline{n3}}\!Rf \quad (4)$$

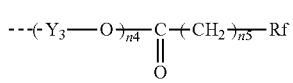

(5)

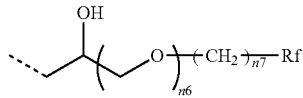

(6)

wherein the dotted line represents a bond; Rf is as defined above; Ra and Rb represent a hydrogen atom or an alkyl group having 1 to 3 carbon atoms; $Y_2$ and $Y_3$ represent a linear or branched alkylene group having 1 to 6 carbon atoms; n1 represents an integer of 0 to 6; n2 represents an integer of 1 to 6; n3 represents an integer of 0 to 6; n4 represents an integer of 1 to 6; n5 represents an integer of 0 to 6; n6 represents 0 or 1; and n7 represents an integer of 0 to 6.

In the case that $R_1$ in the general formula (1) is the organic group shown by the general formula (3), the organic group shown by the general formula (3) is particularly preferably a group shown by the following general formula (3-1). Such a group enables stabilization since the fluorine-substituted alkyl group is separated from the ester portion.

$$-\!\!\!-CH_2\!\!-\!\!CH_2\!\!-\!\!Rf \quad (3\text{-}1)$$

wherein the dotted line represents a bond; and Rf is as defined above.

Illustrative examples of organic groups that can be preferably used as the organic group shown by the general formula (3) include the following groups, although it is not limited thereto.

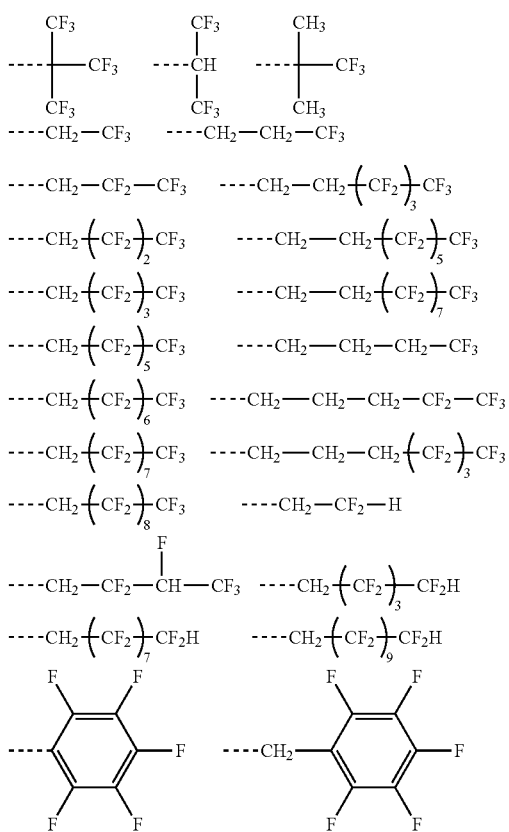

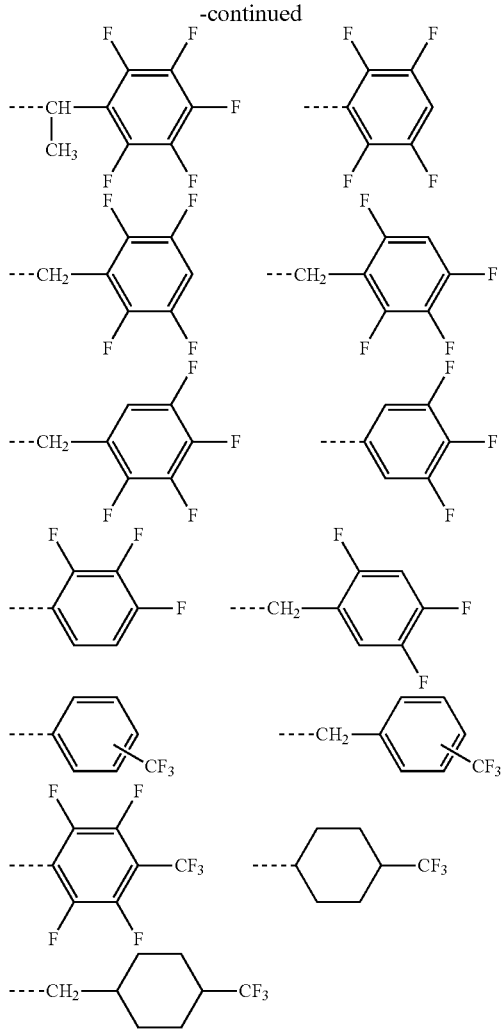
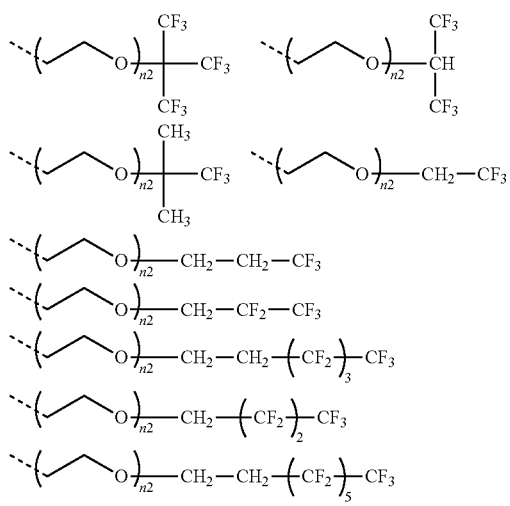
wherein the dotted line represents a bond.
Illustrative examples of organic groups that can be preferably used as the organic group shown by the general formula (4) include the following groups, although it is not limited thereto.
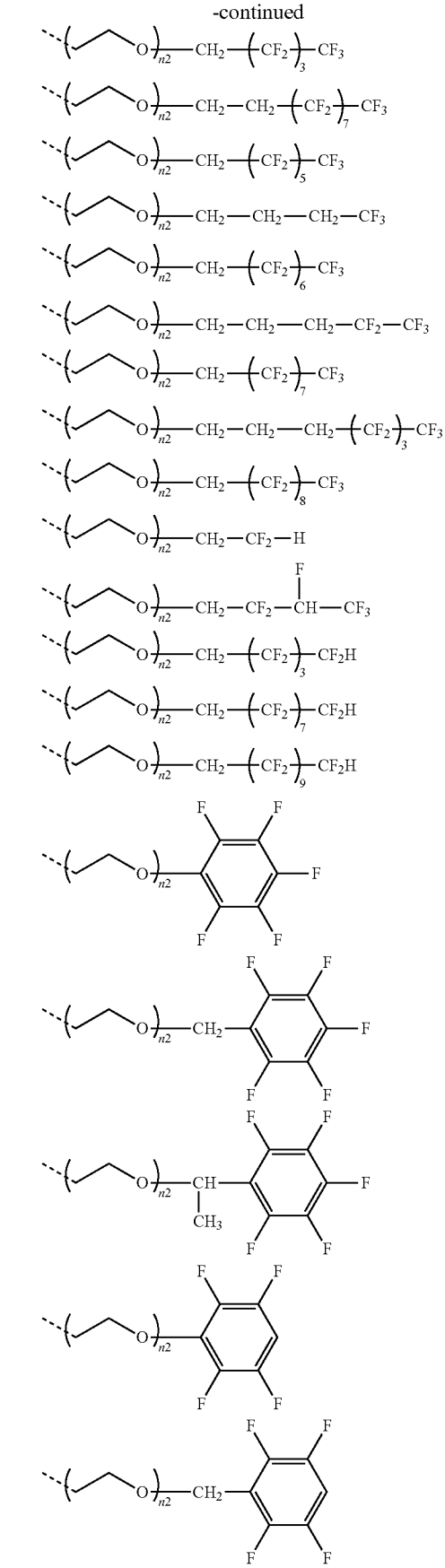

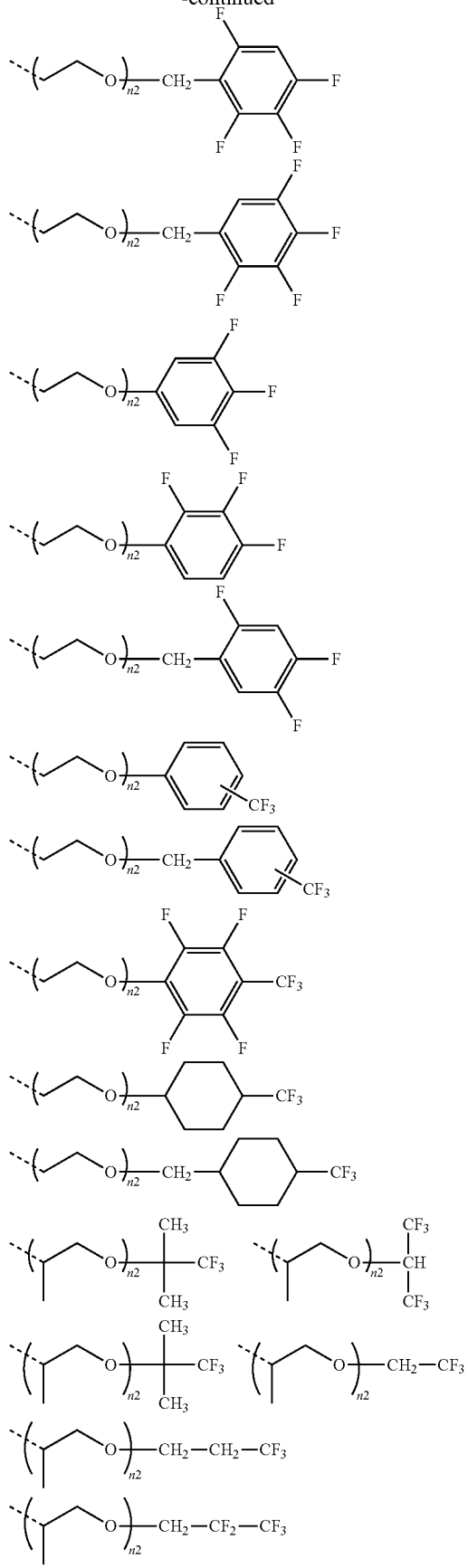
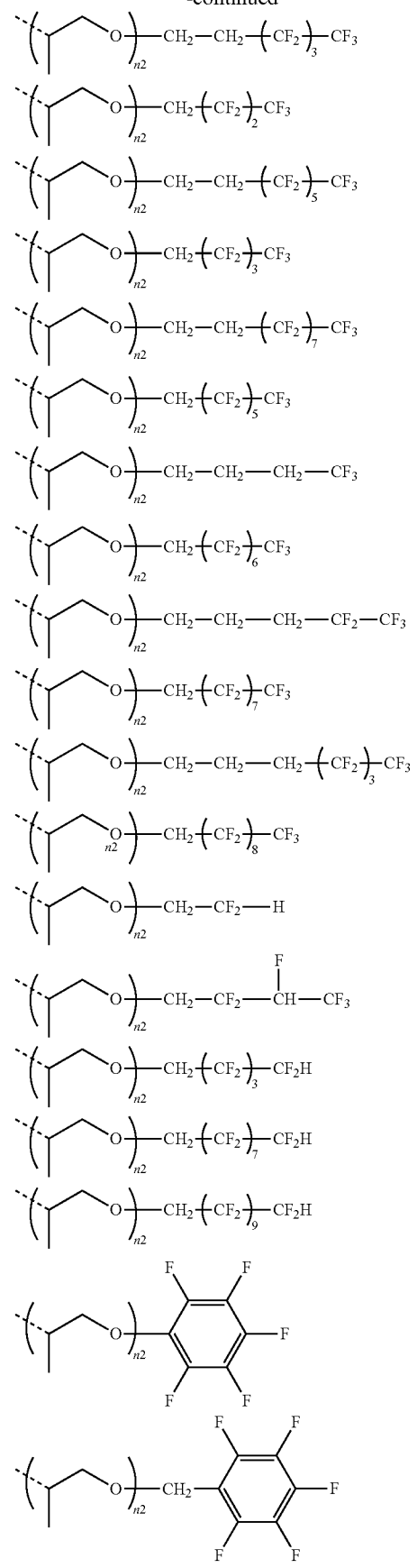

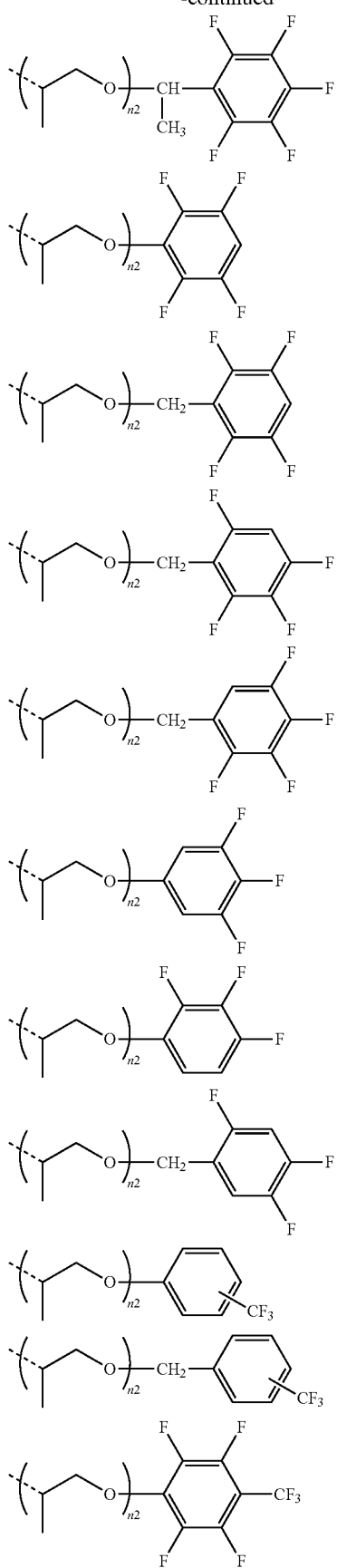
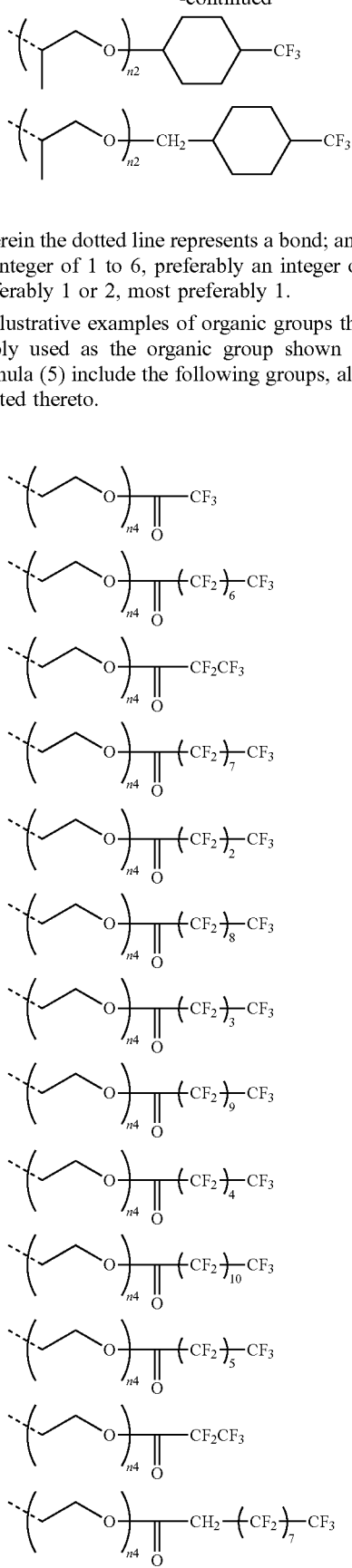
wherein the dotted line represents a bond; and n2 represents an integer of 1 to 6, preferably an integer of 1 to 3, more preferably 1 or 2, most preferably 1.
Illustrative examples of organic groups that can be preferably used as the organic group shown by the general formula (5) include the following groups, although it is not limited thereto.

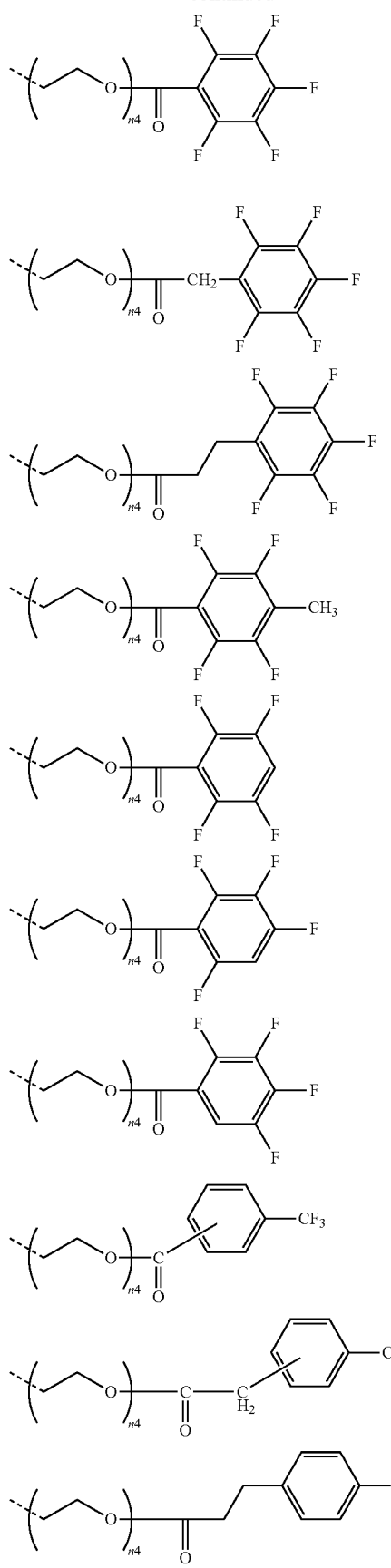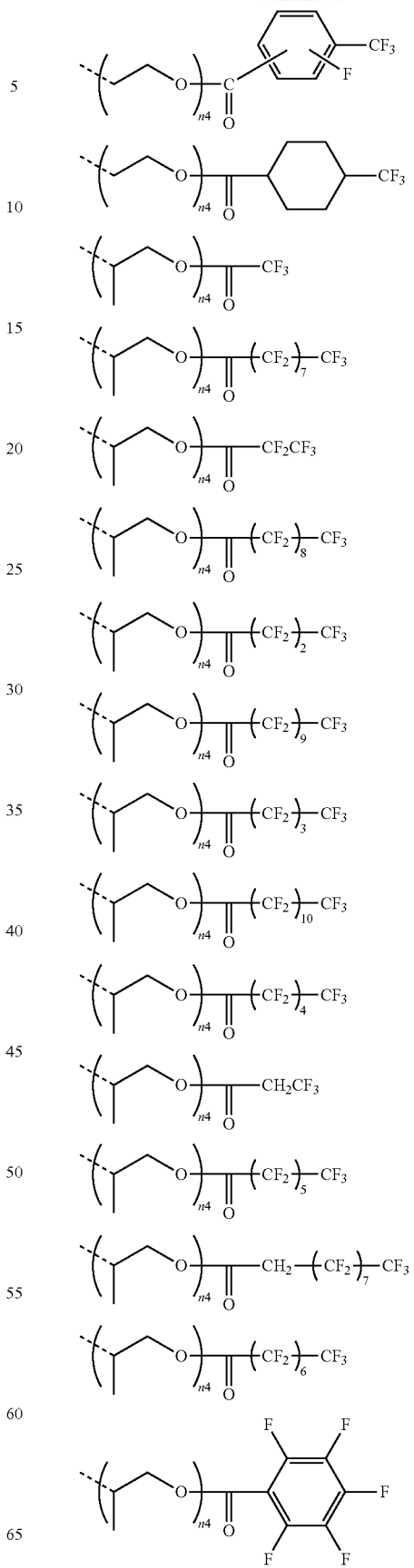

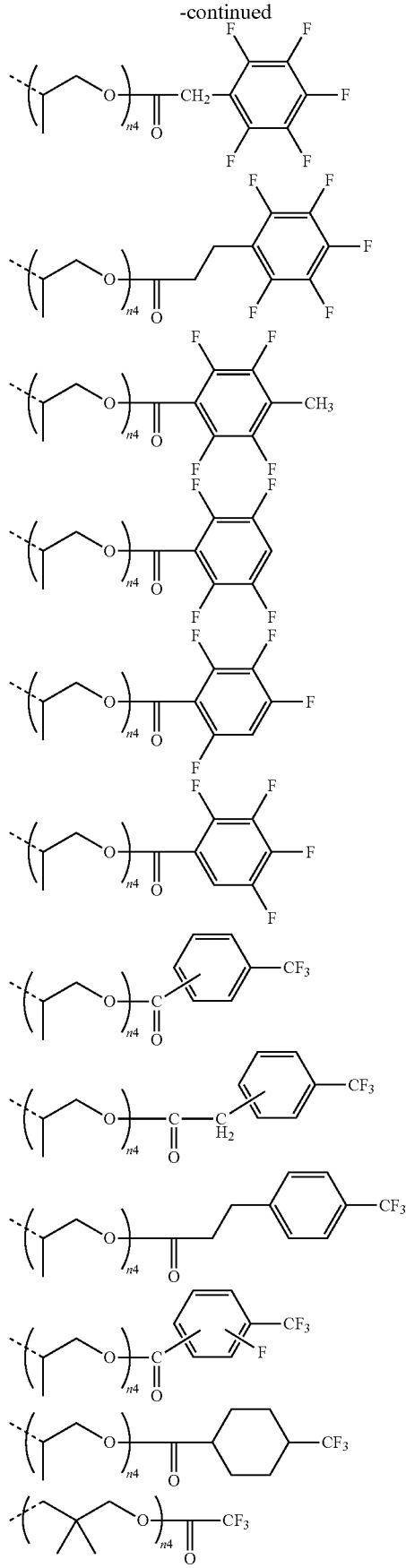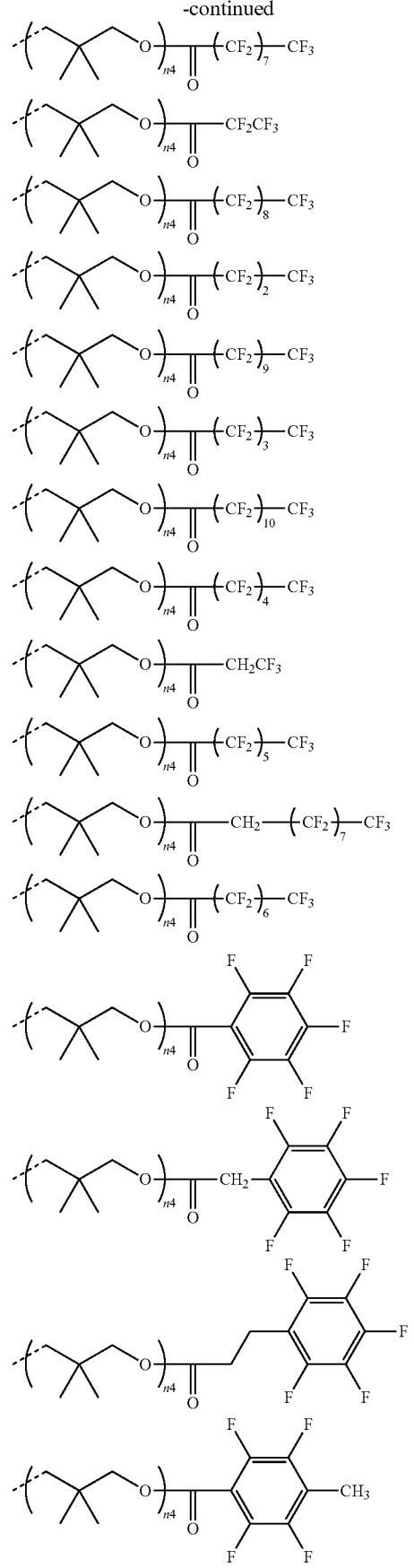

-continued

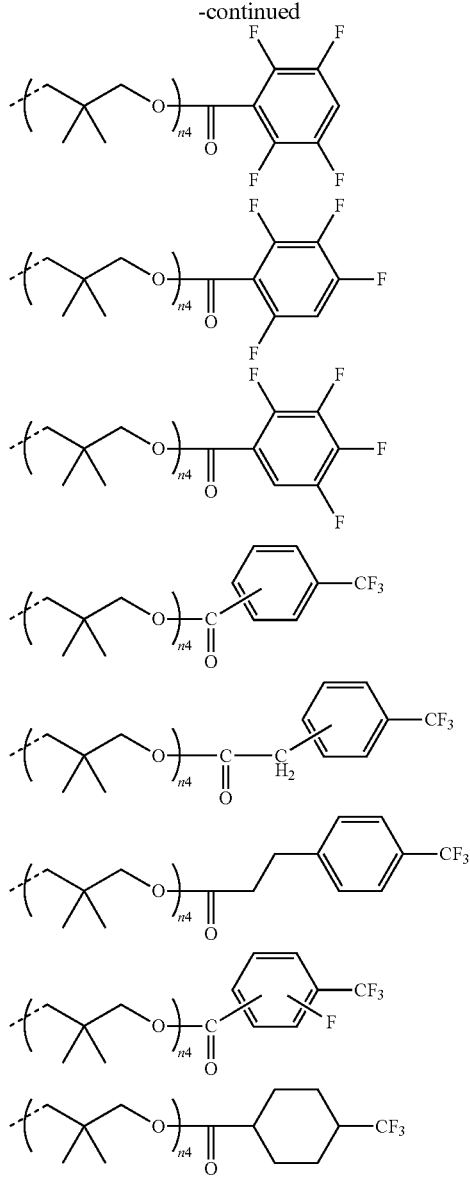

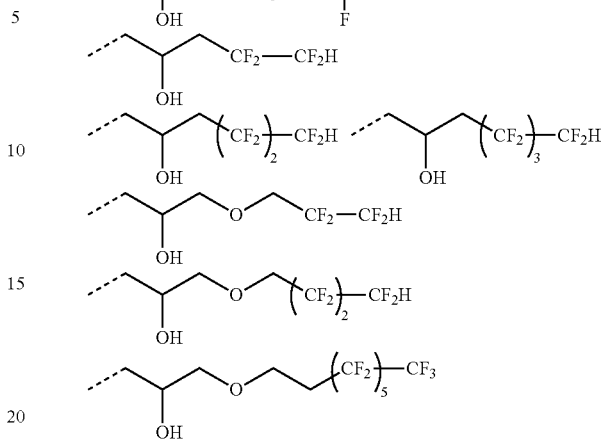

wherein the dotted line represents a bond; n4 represents an integer of 1 to 6, preferably 1 to 3, more preferably 1 or 2, most preferably 1.

Illustrative examples of organic groups that can be preferably used as the organic group shown by the general formula (6) include the following groups, although it is not limited thereto.

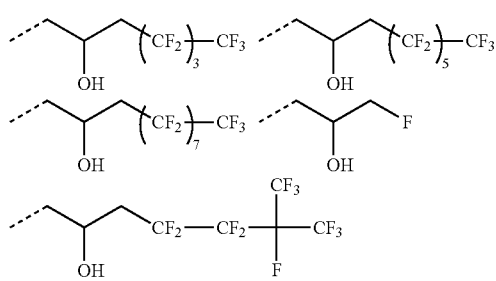

In this regard, after patterning of a negative photosensitive resin composition using the inventive polymer having the polyimide precursor structural unit as a base resin, the polyimide precursor structural unit undergoes imidization ring-closure reaction by heating for post-curing. At this time, the introduced $R_1$ is eliminated and removed from the system, and thus the thickness of the formed film is reduced. Thus, $R_1$ more preferably has low molecular weight to minimize the film loss during post-curing.

(Method for Producing Tetracarboxylic Acid Diester Compound)

The inventive tetracarboxylic acid diester compound can be produced, for example, by reacting a tetracarboxylic dianhydride shown by the following general formula (13) with a compound having a hydroxyl group at its terminal shown by the following general formula (14) in the presence of a basic catalyst such as pyridine to introduce $R_1$. In this method, the tetracarboxylic dianhydride shown by the general formula (13) provides $X_1$ (e.g., a tetravalent organic group shown by the formula (12)) in the general formula (1), and the compound having a hydroxyl group at the terminal shown by the general formula (14) introduces the organic group shown by the general formula (2) thereto.

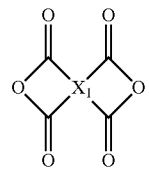

(13)

wherein $X_1$ is as defined above, $$OH\text{-}(\text{-}Y_1\text{-})_n\text{-}(\text{-}Rf)_k \qquad (14)$$

wherein $Y_1$, Rf, "k", and "n" are as defined above.

Preferable examples of the tetracarboxylic dianhydride shown by the general formula (13) include aromatic dianhydrides, alicyclic dianhydrides, and aliphatic dianhydrides. Examples of the aromatic dianhydride include pyromellitic dianhydride, 3,3',4,4'-biphenyltetracarboxylic dianhydride, 2,3,3',4'-biphenyltetracarboxylic dianhydride, 2,3,2',3'-biphenyltetracarboxylic dianhydride, 3,3',4,4'-terphenyltetracarboxylic dianhydride, 3,3',4,4'-oxyphthalic dianhydride, 2,3,3',4'-oxyphthalic dianhydride, 2,3,2',3'-oxyphthalic dianhydride, diphenylsulfone-3,3',4,4'-tetracarboxylic dianhydride, benzophenone-3,3',4,4'-tetracarboxylic dianhydride, 2,2-bis(3,4-dicarboxyphenyl)propane dianhydride, 2,2-bis(2,3-dicarboxyphenyl)propane dianhydride, 1,1-bis(3,4-dicarboxyphenyl)ethane dianhydride, 1,1-bis(2,3-dicarboxyphenyl)ethane dianhydride, bis(3,4-dicarboxyphenyl)methane dianhydride, bis(2,3-dicarboxyphenyl)methane dianhydride, 1,4-(3,4-dicarboxyphenoxy)benzene dianhydride, p-phenylene bis(trimellitic acid monoester anhydride), bis(1,3-dioxo-1,3-dihydroisobenzofuran-5-carboxylic acid)1,4-phenylene, 2,2-bis(4-(4-aminophenoxy)phenyl)propane, 1,2,5,6-naphthalenetetracarboxylic dianhydride, 2,3,6,7-naphthalenetetracarboxylic dianhydride, 9,9-bis(3,4-dicarboxyphenyl)fluorene dianhydride, 2,3,5,6-pyridinetetracarboxylic dianhydride, 3,4,9,10-perylenetetracarboxylic dianhydride, 2,2-bis(3,4-dicarboxyphenyl)hexafluoropropane dianhydride, 2,2-bis(4-(3,4-dicarboxybenzoyloxy)phenyl)hexafluoropropane dianhydride, 1,6-difluoropromellitic dianhydride, 1-trifluoromethylpyromellitic dianhydride, 1,6-ditrifluoromethylpyromellitic dianhydride, 2,2'-bis(trifluoromethyl)-4,4'-bis(3,4-dicarboxyphenoxy)biphenyl dianhydride, 2,2'-bis[(dicarboxyphenoxy)phenyl]propane dianhydride, 2,2'-bis[(dicarboxyphenoxy)phenyl]hexafluoropropane dianhydride, and acid dianhydride compounds obtained by substituting the aromatic ring of the above compounds with a substituent such as an alkyl group, an alkoxy group, or a halogen atom, although not limited thereto.

Examples of the alicyclic dianhydride include 1,2,3,4-cyclobutanetetracarboxylic dianhydride, 1,2,3,4-cyclopentanetetracarboxylic dianhydride, 1,2,4,5-cyclohexanetetracarboxylic dianhydride, 1,2,4,5-cyclopentanetetracarboxylic dianhydride, 1,2,3,4-tetramethyl-1,2,3,4-cyclobutanetetracarboxylic dianhydride, 1,2-dimethyl-1,2,3,4-cyclobutanetetracarboxylic dianhydride, 1,3-dimethyl-1,2,3,4-cyclobutanetetracarboxylic dianhydride, 1,2,3,4-cycloheptanetetracarboxylic dianhydride, 2,3,4,5-tetrahydrofurantetracarboxylic dianhydride, 3,4-dicarboxy-1-cyclohexylsuccinic dianhydride, 2,3,5-tricarboxycyclopentylacetic dianhydride, 3,4-dicarboxy-1,2,3,4-tetrahydro-1-naphthalenesuccinic dianhydride, bicyclo[3.3.0]octane-2,4,6,8-tetracarboxylic dianhydride, bicyclo[4.3.0]nonane-2,4,7,9-tetracarboxylic dianhydride, bicyclo[4.4.0]decane-2,4,7,9-tetracarboxylic dianhydride, bicyclo[4.4.0]decane-2,4,8,10-tetracarboxylic dianhydride, tricyclo[6.3.0.0$^{2,6}$]undecane-3,5,9,11-tetracarboxylic dianhydride, bicyclo[2.2.2]octane-2,3,5,6-tetracarboxylic dianhydride, bicyclo[2.2.2]oct-7-ene-2,3,5,6-tetracarboxylic dianhydride, bicyclo[2.2.1]heptane tetracarboxylic dianhydride, bicyclo[2.2.1]heptane-5-carboxymethyl-2,3,6-tricarboxylic dianhydride, 7-oxabicyclo[2.2.1]heptane-2,4,6,8-tetracarboxylic dianhydride, octahydronaphthalene-1,2,6,7-tetracarboxylic dianhydride, tetradecahydroanthracene-1,2,8,9-tetracarboxylic dianhydride, 3,3',4,4'-dicyclohexanetetracarboxylic dianhydride, 3,3',4,4'-oxydicyclohexanetetracarboxylic dianhydride, 5-(2,5-dioxotetrahydro-3-furanyl)-3-methyl-3-cyclohexene-1,2-dicarboxylic anhydride, and "RIKACID"® BT-100 (manufactured by New Japan Chemical Co., Ltd), derivatives thereof, and acid dianhydride compounds obtained by substituting the alicyclic ring of the above compounds with a substituent such as an alkyl group, an alkoxy group, or a halogen atom, although not limited thereto.

Examples of the aliphatic dianhydride include 1,2,3,4-butanetetracarboxylic dianhydride, 1,2,3,4-pentanetetracarboxylic dianhydride, and derivative thereof, although not limited thereto.

These aromatic dianhydrides, alicyclic dianhydrides, and aliphatic dianhydrides may be used alone or in combination of two or more kinds.

For the reaction of the tetracarboxylic dianhydride shown by the general formula (13) with the compound having a hydroxyl group at the terminal shown by the general formula (14), the tetracarboxylic dianhydride shown by the general formula (13) and the compound having a hydroxyl group at the terminal shown by the general formula (14) may be stirred, dissolved, and mixed in the presence of a basic catalyst such as pyridine in a reaction solvent, at a reaction temperature of 20 to 50° C., over 4 to 10 hours. In this manner, half-esterification reaction of the acid dianhydride progresses, and a solution in which an intended tetracarboxylic acid diester compound shown by the general formula (1) is dissolved in the reaction solvent can be obtained.

The obtained tetracarboxylic acid diester compound may be isolated, or the obtained solution as is may be used for a subsequent reaction with a diamine.

The reaction solvent is preferably a solvent that can favorably dissolve the above tetracarboxylic acid diester compound and a polymer having a polyimide precursor structural unit obtained by the subsequent polycondensation reaction of the tetracarboxylic acid diester compound with a diamine. Examples of the solvent include N-methyl-2-pyrrolidone, N,N-dimethylacetamide, N,N-dimethylformamide, dimethylsulfoxide, tetramethylurea, and γ-butyrolactone. In addition, ketones, esters, lactones, ethers, halogenated hydrocarbons, and hydrocarbons can also be used. Illustrative examples thereof include acetone, methyl ethyl ketone, methyl isobutyl ketone, cyclohexanone, methyl acetate, ethyl acetate, butyl acetate, diethyl oxalate, ethylene glycol dimethyl ether, diethylene glycol dimethyl ether, tetrahydrofuran, dichloromethane, 1,2-dichloroethane, 1,4-dichlorobutane, chlorobenzene, o-dichlorobenzene, hexane, heptane, benzene, toluene, and xylene. These solvents may be used alone or in combination of two or more kinds as needed.

[Polyimide Precursor Polymer]

The inventive polyimide precursor polymer (a polymer having a polyimide precursor structural unit) contains a structural unit shown by the following general formula (7) (hereinafter, also referred to as a polymer having the structural unit (7)),

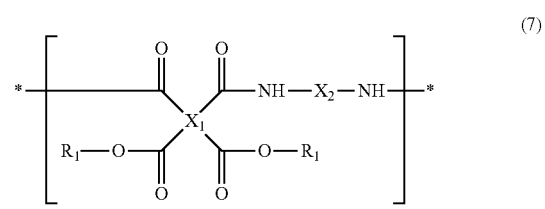

(7)

wherein $X_1$ represents a tetravalent organic group; $X_2$ represents a divalent organic group; and $R_1$ represents a group shown by the following general formula (2),

(2)

wherein the dotted line represents a bond; $Y_1$ represents an organic group with a valency of k+1; Rf represents a linear, branched, or cyclic alkyl group having 1 to 20 carbon atoms or an aromatic group in which a part or all of hydrogen atoms is/are substituted with a fluorine atom(s); "k" represents 1, 2, or 3; and "n" represents 0 or 1.

$X_1$ and $R_1$ in the general formula (7) are the same as in the general formula (1) described above. $X_2$ in the general formula (7), which is any divalent organic group, is preferably a divalent organic group having 6 to 40 carbon atoms, more preferably a cyclic organic group containing 1 to 4 aromatic or alicyclic rings each having a substituent, or an aliphatic group or siloxane group having no cyclic structure. $X_2$ is still more preferably a structure shown by the following formula (15) or (16). The structure of $X_2$ may be one kind or a combination of two or more kinds.

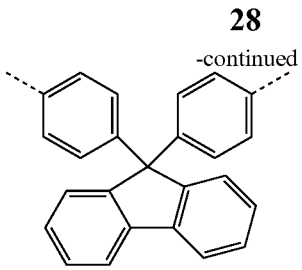

wherein the dotted line represents a bond with an amino group.

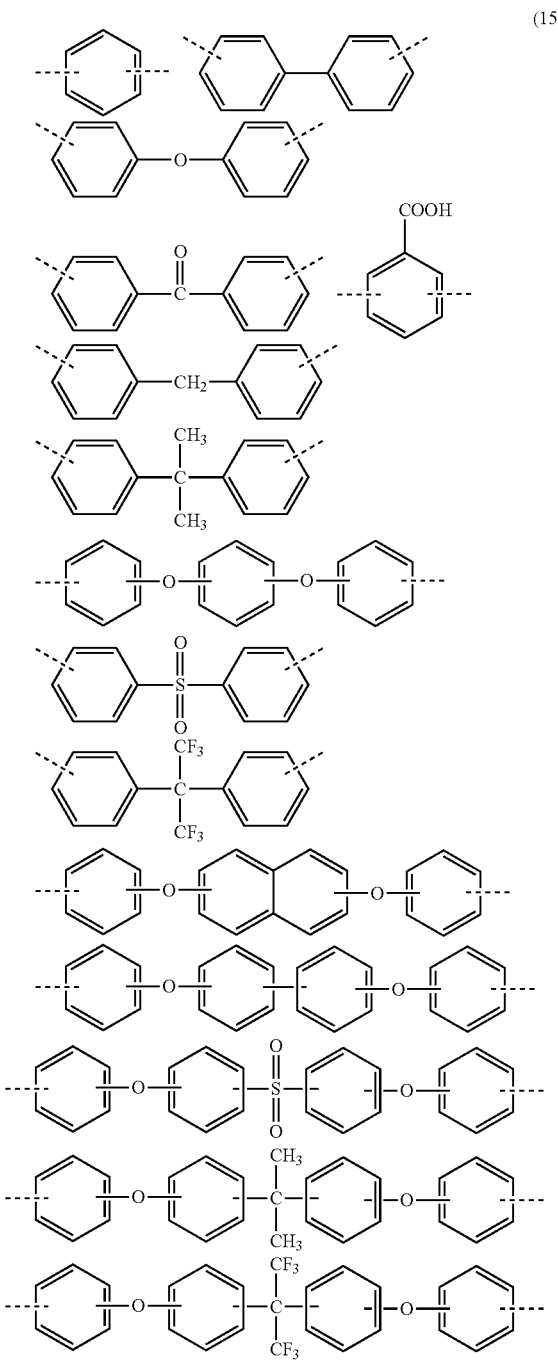

(15)

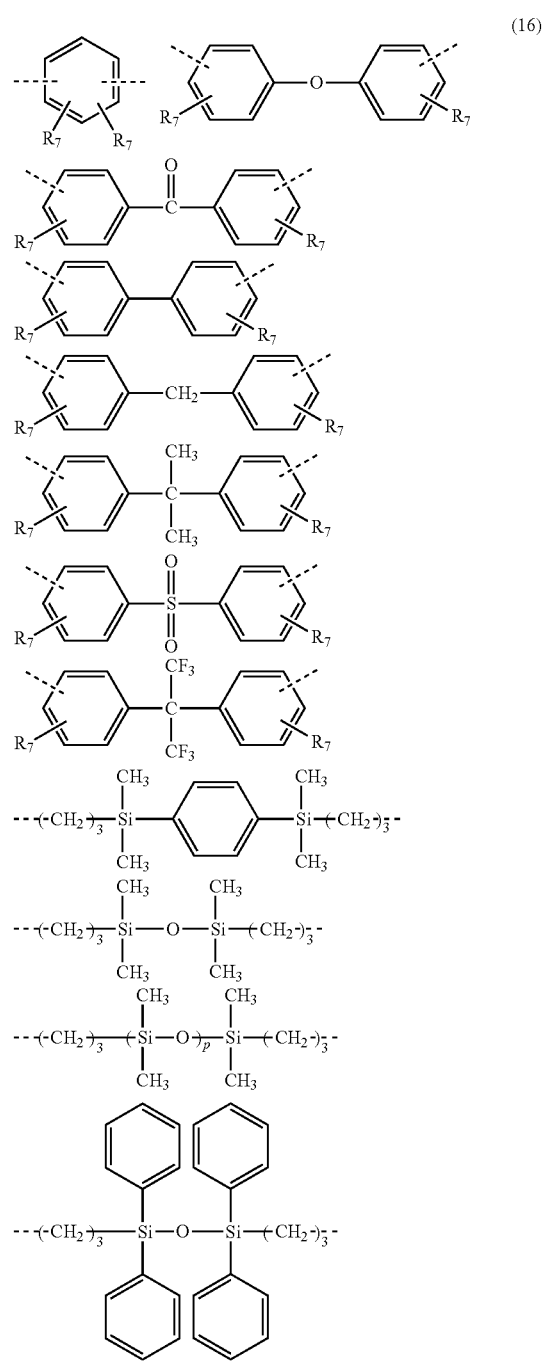

(16)

wherein the dotted line represents a bond with an amino group; $R_7$ independently represents a methyl group, an ethyl group, a propyl group, a n-butyl group, or a trifluoromethyl group; and "p" represents a positive number of 2 to 20.

The inventive polyimide precursor polymer preferably further contains a structural unit shown by the following general formula (8), in addition to the structural unit shown by the general formula (7). The polymer containing the structural unit shown by the general formula (8) is a polymer having the structural unit (8), besides the structural unit (7), and the structural unit (8) contains a polymerizable unsaturated linking group shown by the following general formula (9).

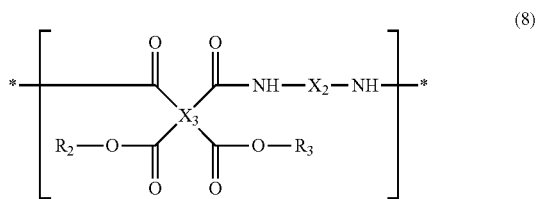

(8)

wherein $X_2$ is as defined above; $X_3$ represents a tetravalent organic group that is the same as or different from $X_1$; and $R_2$ and $R_3$ independently represent a hydrogen atom, a linear, branched, or cyclic alkyl group having 1 to 6 carbon atoms, or an organic group shown by the following general formula (9), provided that at least one of $R_2$ and $R_3$ is an organic group shown by the general formula (9),

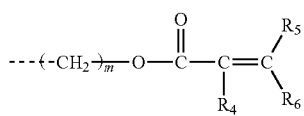

(9)

wherein the dotted line represents a bond; $R_4$ represents a hydrogen atom or an organic group having 1 to 3 carbon atoms; $R_5$ and $R_6$ independently represent a hydrogen atom or an organic group having 1 to 3 carbon atoms; and "m" represents an integer of 2 to 10.

In the general formula (8), $X_3$ represents a tetravalent organic group that is the same as or different from $X_1$ and is not limited to particular tetravalent organic groups. $X_3$ is preferably a tetravalent organic group of an alicyclic aliphatic group having 4 to 40 carbon atoms or an aromatic group, more preferably selected from tetravalent organic groups shown by the formula (12). The structure of $X_3$ may be one kind or a combination of two or more kinds.

$R_4$ in the general formula (9), which is a hydrogen atom or any organic group having 1 to 3 carbon atoms, is preferably a hydrogen atom or a methyl group, in view of photosensitive property of a negative photosensitive resin composition.

$R_5$ and $R_6$ in the general formula (9), which independently represent a hydrogen atom or any organic group having 1 to 3 carbon atoms, are preferably a hydrogen atom, in view of photosensitive property of a negative photosensitive resin composition.

"m" in the general formula (9), which represents an integer of 2 to 10, is preferably an integer of 2 to 4, in view of photosensitive property. "m" is more preferably 2.

$R_2$ and $R_3$ in the general formula (8) independently represent a hydrogen atom, a linear, branched, or cyclic alkyl group having 1 to 6 carbon atoms, or an organic group shown by the general formula (9), provided that at least one of $R_2$ and $R_3$ is an organic group shown by the general formula (9).

(Method for Producing Polyimide Precursor Polymer)

Furthermore, the present invention provides a method for producing the inventive polyimide precursor polymer. The polyimide precursor polymer having the structural unit shown by the general formula (7) can be obtained by reacting a tetracarboxylic acid diester compound shown by the following general formula (1) with a diamine shown by the following general formula (10),

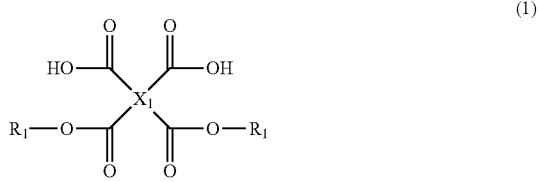

(1)

wherein $X_1$ and $R_1$ are as defined above,

$H_2N-X_2-NH_2$ (10)

wherein $X_2$ is as defined above.

Examples of the diamine shown by the general formula (10) include aromatic diamines, alicyclic diamines, and aliphatic diamines. Preferable examples of the aromatic diamine include 3,4'-diaminodiphenyl ether, 4,4'-diaminodiphenyl ether, 3,4'-diaminodiphenylmethane, 4,4'-diaminodiphenylmethane, 3,3'-diaminodiphenylsulfone, 3,4'-diaminodiphenylsulfone, 4,4'-diaminodiphenylsulfone, 3,4'-diaminodiphenylsulfide, 4,4'-diaminodiphenylsulfide, 1,4-bis(4-aminophenoxy)benzene, benzidine, 2,2'-bis(trifluoromethyl)benzidine, 3,3'-bis(trifluoromethyl)benzidine, 2,2'-dimethylbenzidine, 3,3'-dimethylbenzidine, 2,2'3,3'-tetramethylbenzidine, 2,2'-dichlorobenzidine, 3,3'-dichlorobenzidine, 2,2'3,3'-tetrachlorobenzidine, m-phenylenediamine, p-phenylenediamine, 1,5-naphthalenediamine, 2,6-naphthalenediamine, bis(4-aminophenoxyphenyl)sulfone, bis(3-aminophenoxyphenyl)sulfone, bis[4-(3-aminophenoxy)phenyl]sulfone, bis(4-aminophenoxy)biphenyl, bis{4-(4-aminophenoxy)phenyl}ether, 1,4-bis(4-aminophenoxy)benzene, 9,9-bis(4-aminophenyl)fluorene, 2,2'-bis[3-(3-aminobenzamido)-4-hydroxyphenyl]hexafluoropropane, 4-aminophenyl-4'-aminobenzoate, 4,4'-diaminobenzanilide, and diamine compounds obtained by substituting the aromatic ring of the above compounds with a substituent such as an alkyl group, an alkoxy group, or a halogen atom, although not limited thereto.

Examples of the alicyclic diamine include cyclobutanediamine, isophoronediamine, bicyclo[2.2.1]heptanebismethylamine, tricyclo[3.3.1.1$^{3,7}$]decane-1,3-diamine, 1,2-cyclohexyldiamine, 1,3-cyclohexyldiamine, 1,4-diaminocyclohexane, trans-1,4-diaminocyclohexane, cis-1,4-diaminocyclohexane, 4,4'-diaminodicyclohexylmethane, 3,3'-dimethyl-4,4'-diaminodicyclohexylmethane, 3,3'-diethyl-4,4'-diaminodicyclohexylmethane, 3,3',5,5'-tetramethyl-4,4'-diaminodicyclohexylmethane, 3,3',5,5'-tetraethyl-4,4'-diaminodicyclohexylmethane, 3,5-diethyl-3',5'-dimethyl-4,4'-diaminodicyclohexylmethane, 4,4'-diaminodicyclohexyl ether, 3,3'-dimethyl-4,4'- diaminodicyclohexyl ether, 3,3'-diethyl-4,4'-diaminodicyclohexyl ether, 3,3',5,5'-tetramethyl-4,4'-diaminodicyclohexyl ether, 3,3',5,5'-tetraethyl-4,4'-diaminodicyclohexyl ether, 3,5-diethyl-3',5'-dimethyl-4,4'-diaminodicyclohexyl ether, 2,2-bis(4-aminocyclohexyl)propane, 2,2-bis(3-methyl-4-aminocyclohexyl)propane, 2,2-bis(3-ethyl-4-aminocyclohexyl)propane, 2,2-bis(3,5-dimethyl-4-aminocyclohexyl)propane, 2,2-bis(3,5-diethyl-4-aminocyclohexyl)propane, 2,2-(3,5-diethyl-3',5'-dimethyl-4,4'-diaminodicyclohexyl)propane, and diamine compounds obtained by substituting the alicyclic ring of the above compounds with a substituent such as an alkyl group, an alkoxy group, or a halogen atom, although not limited thereto.

Examples of the aliphatic diamine include alkylene diamines such as ethylenediamine, 1,3-diaminopropane, 1,4-diaminobutane, 1,5-diaminopentane, 1,6-diaminohexane, 1,7-diaminoheptane, 1,8-diaminooctane, 1,9-diaminononane, and 1,10-diaminodecane; ethylene glycol diamines such as bis(aminomethyl)ether, bis(2-aminoethyl)ether, and bis(3-aminopropyl)ether; and siloxane diamines such as 1,3-bis(3-aminopropyl)tetramethyldisiloxane, 1,3-bis(4-aminobutyl)tetramethyldisiloxane, and α,ω-bis(3-aminopropyl)polydimethylsiloxane, although not limited thereto.

These aromatic diamines, alicyclic diamines, or aliphatic diamines may be used alone or in combination of two or more kinds.

In addition, siloxane diamines can also be suitably used.

The polyimide precursor polymer having the structural unit shown by the general formula (7) can be obtained, for example, by reacting the tetracarboxylic acid diester compound shown by the general formula (1) with the diamine shown by the general formula (10) in the presence of a dehydration condensation agent. More specifically, the tetracarboxylic acid diester compound shown by the general formula (1) is used with a reaction solvent dissolving it. To this reaction solvent, a known dehydration condensation agent (for example, dicyclohexylcarbodiimide, 1-ethoxycarbonyl-2-ethoxy-1,2-dihydroquinoline, 1,1-carbonyldioxy-di-1,2,3-benzotriazole, or N,N'-disuccinimidylcarbonate) is added and mixed under ice-cooling to obtain a polyacid anhydride of the tetracarboxylic acid diester compound shown by the general formula (1). Then, the diamine shown by the general formula (10) is separately dissolved or dispersed in a solvent, and this solution or dispersion is added dropwise to the anhydride to perform polycondensation. The polyimide precursor polymer having the structural unit shown by the general formula (7) can be thus obtained.

As an alternative method for reacting the tetracarboxylic acid diester compound shown by the general formula (1) with the diamine (the diamine compound) shown by the general formula (10) to obtain the polyimide precursor polymer having the structural unit shown by the general formula (7), the tetracarboxylic acid diester compound shown by the general formula (1) may be converted to an acid chloride by a chlorinating agent such as thionyl chloride or dichlorooxalic acid and then undergo reaction with the diamine shown by the general formula (10) to synthesize the polymer.

In the reaction for converting the tetracarboxylic acid diester compound into an acid chloride by a chlorinating agent, a basic compound may be used. Examples of the basic compound include pyridine, 4-dimethylaminopyridine, and triethylamine.

Then, the resulting acid chloride of the tetracarboxylic acid diester compound is reacted with the diamine shown by the general formula (10) in the presence of a basic catalyst to obtain an intended polyimide precursor polymer having the structural unit shown by the general formula (7). Examples of the basic catalyst include pyridine, dimethylaminopyridine, 1,8-diazabicyclo[5.4.0]undec-7-ene, and 1,5-diazabicyclo[4.3.0]non-5-ene.

The solvent used in the method for producing the inventive polyimide precursor polymer via an acid chloride is preferably a solvent that can favorably dissolve the tetracarboxylic acid diester compound, the acid chloride thereof, and the polyimide precursor polymer obtained by polycondensation reaction with a diamine, and the same solvent as described above may be used. Illustrative examples thereof include N-methyl-2-pyrrolidone, N,N-dimethylacetamide, N,N-dimethylformamide, dimethylsulfoxide, tetramethylurea, hexamethylphosphoric triamide, and γ-butyrolactone. In addition to polar solvents, ketones, esters, lactones, ethers, halogenated hydrocarbons, and hydrocarbons can also be used. Illustrative examples thereof include acetone, diethyl ketone, methyl ethyl ketone, methyl isobutyl ketone, cyclohexanone, methyl acetate, ethyl acetate, butyl acetate, diethyl oxalate, diethyl malonate, diethyl ether, ethylene glycol dimethyl ether, diethylene glycol dimethyl ether, tetrahydrofuran, dichloromethane, 1,2-dichloroethane, 1,4-dichlorobutane, trichloroethane, chlorobenzene, o-dichlorobenzene, hexane, heptane, octane, benzene, toluene, and xylene. These solvents may be used alone or in combination of two or more kinds.

The molecular weight of the intended polyimide precursor polymer having the structural unit shown by the general formula (7) is preferably 5,000 to 100,000, more preferably 7,000 to 30,000. When the molecular weight is 5,000 or more, a negative photosensitive resin composition using the polyimide precursor polymer as a base resin can be easily applied to form a film with a desired thickness on a substrate. When the molecular weight is 100,000 or less, viscosity of the negative photosensitive resin composition is not so high that a film can be formed.

In addition, the polyimide precursor polymer having the structural unit shown by the general formula (7) and the structural unit shown by the general formula (8) can be produced by reacting a tetracarboxylic acid diester compound shown by the following general formula (1) with a diamine shown by the following general formula (10) and a tetracarboxylic acid diester compound shown by the following general formula (11),

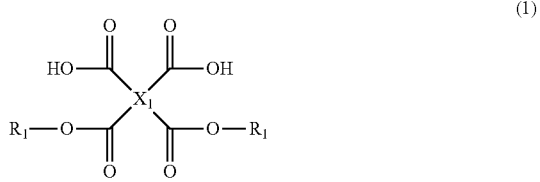

(1)

wherein $X_1$ and $R_1$ are as defined above, $$H_2N-X_2-NH_2 \quad (10)$$

wherein $X_2$ is as defined above,

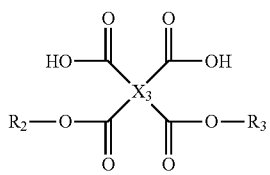
(11)

wherein $X_3$, $R_2$, and $R_3$ are as defined above.

In the general formula (11), $X_3$ represents a tetravalent organic group that is the same as or different from $X_1$ and is not limited to particular tetravalent organic groups. $X_3$ is preferably a tetravalent organic group of an alicyclic aliphatic group having 4 to 40 carbon atoms or an aromatic group, more preferably selected from tetravalent organic groups shown by the formula (12). The structure of $X_3$ may be one kind or a combination of two or more kinds.

$R_2$ and $R_3$ in the general formula (11) independently represent a hydrogen atom, a linear, branched, or cyclic alkyl group having 1 to 6 carbon atoms, or an organic group shown by the general formula (9), provided that at least one of $R_2$ and $R_3$ is an organic group shown by the general formula (9). Here, the tetracarboxylic acid diester compound shown by the general formula (11) can be obtained by reaction of a tetracarboxylic dianhydride that provides $X_3$ (e.g., a tetravalent organic group shown by the formula (12)) with a compound having a hydroxyl group at the terminal shown by the following general formula (17) in the presence of a basic catalyst such as pyridine to introduce the organic group shown by the general formula (9) into at least one of $R_2$ and $R_3$,

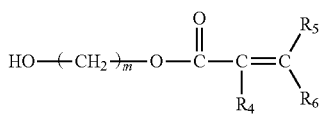
(17)

wherein $R_4$, $R_5$, $R_6$, and "m" are as defined above.

The reaction of the tetracarboxylic dianhydride with the compound having a hydroxyl group at the terminal shown by the general formula (17) can be performed, specifically, in the same manner as the above-described reaction of the tetracarboxylic dianhydride with the compound having a hydroxyl group at the terminal shown by the general formula (14).

$R_4$ in the general formula (17), which is a hydrogen atom or any organic group having 1 to 3 carbon atoms, is preferably a hydrogen atom or a methyl group, in view of photosensitive property of a negative photosensitive resin composition.

$R_5$ and $R_6$ in the general formula (17), which independently represent a hydrogen atom or any organic group having 1 to 3 carbon atoms, are preferably a hydrogen atom, in view of photosensitive property of a negative photosensitive resin composition.

"m" in the general formula (17), which represents an integer of 2 to 10, is preferably an integer of 2 to 4, in view of photosensitive property. "m" is more preferably 2.

Preferable examples of the compound having a hydroxyl group at the terminal shown by the general formula (17) include 2-acryloyloxyethyl alcohol, 1-acryloyloxy-3-propyl alcohol, 2-methacryloyloxyethyl alcohol, and 1-methacryloyloxy-3-propyl alcohol.

In addition, $R_2$ and $R_3$ in the general formula (11) may be a linear, branched, or cyclic alkyl group having 1 to 6 carbon atoms. As a method for introducing a linear, branched, or cyclic alkyl group having 1 to 6 carbon atoms into the compounds of formulae (8) and (11) (i.e., a method for making $R_2$ and $R_3$ a linear, branched, or cyclic alkyl group having 1 to 6 carbon atoms), there may be mentioned a method in which a linear, branched, or cyclic alcohol having 1 to 6 carbon atoms is added simultaneously with the reaction of the compound having a hydroxyl group at the terminal shown by the general formula (17) and the tetracarboxylic dianhydride in the presence of a basic catalyst such as pyridine.

Examples of alcohol suited for the reaction include methanol, ethanol, 1-propanol, 2-propanol, 1-butanol, 2-butanol, 1-pentanol, 2-pentanol, 3-pentanol, neopentyl alcohol, 1-hexanol, 2-hexanol, 3-hexanol, cyclopentanol, and cyclohexanol.

The reaction of the tetracarboxylic acid diester compound shown by the general formula (1), the tetracarboxylic acid diester compound shown by the general formula (11), and the diamine shown by the general formula (10) can be performed in the same manner as the above-described reaction of the tetracarboxylic acid diester compound shown by the general formula (1) with the diamine shown by the general formula (10).

The molecular weight of the polymer having the structural unit (8) is the same as that of the polymer having the structural unit (7), namely, preferably 5,000 to 100,000, more preferably 7,000 to 30,000.

Both terminals of the polymer having the structural unit (7) and the polymer having the structural unit (8) may be sealed with a terminal sealing agent to control the molecular weight at polycondensation reaction and to inhibit time-dependent change of the molecular weight of the obtained polymer, i.e., to inhibit gelation. A terminal sealing agent for the acid dianhydride may be a monoamine or a monohydric alcohol. A terminal sealing agent for the diamine compound may be an acid anhydride, a monocarboxylic acid, a mono-acid chloride compound, a mono-active ester compound, a dicarbonic acid ester, or a vinyl ether. In addition, reaction of the terminal sealing agent allows various organic groups to be introduced into the terminal.

Examples of the monoamine used as the sealing agent for the acid anhydride terminal include aniline, 5-amino-8-hydroxyquinoline, 4-amino-8-hydroxyquinoline, 1-hydroxy-8-aminonaphthalene, 1-hydroxy-7-aminonaphthalene, 1-hydroxy-6-aminonaphthalene, 1-hydroxy-5-aminonaphthalene, 1-hydroxy-4-aminonaphthalene, 1-hydroxy-3-aminonaphthalene, 1-hydroxy-2-aminonaphthalene, 1-amino-7-hydroxynaphthalene, 2-hydroxy-7-aminonaphthalene, 2-hydroxy-6-aminonaphthalene, 2-hydroxy-5-aminonaphthalene, 2-hydroxy-4-aminonaphthalene, 2-hydroxy-3-aminonaphthalene, 1-amino-2-hydroxynaphthalene, 1-carboxy-8-aminonaphthalene, 1-carboxy-7-aminonaphthalene, 1-carboxy-6-aminonaphthalene, 1-carboxy-5-aminonaphthalene, 1-carboxy-4-aminonaphthalene, 1-carboxy-3-aminonaphthalene, 1-carboxy-2-aminonaphthalene, 1-amino-7-carboxynaphthalene, 2-carboxy-7-aminonaphthalene, 2-carboxy-6-aminonaphthalene, 2-carboxy-5-aminonaphthalene, 2-carboxy-4-aminonaphthalene, 2-carboxy-3-aminonaphthalene, 1-amino-2-carboxynaphthalene, 2-aminonicotinic acid, 4-aminonicotinic acid, 5-aminonicotinic acid, 6-aminonicotinic acid, 4-aminosalicylic acid, 5-aminosalicylic acid, 6-aminosalicylic acid, ameride, 2-aminobenzoic acid, 3-aminobenzoic acid, 4-aminobenzoic acid, 2-aminobenzenesulfonic acid, 3-aminobenzenesulfonic acid, 4-aminobenzenesulfonic acid, 3-amino-4,6-dihydroxypyrimidine, 2-aminophenol, 3-aminophenol, 4-aminophenol, 5-amino-8-mercaptoquinoline, 4-amino-8-mercaptoquinoline, 1-mercapto-8-aminonaphthalene, 1-mercapto-7-aminonaphthalene, 1-mercapto-6-aminonaphthalene, 1-mercapto-5-aminonaphthalene, 1-mercapto-4-aminonaphthalene, 1-mercapto-3-aminonaphthalene, 1-mercapto-2-aminonaphthalene, 1-amino-7-mercaptonaphthalene, 2-mercapto-7-aminonaphthalene, 2-mercapto-6-aminonaphthalene, 2-mercapto-5-aminonaphthalene, 2-mercapto-4-aminonaphthalene, 2-mercapto-3-aminonaphthalene, 1-amino-2-mercaptonaphthalene, 3-amino-4,6-dimercaptopyrimidine, 2-aminothiophenol, 3-aminothiophenol, 4-aminothiophenol, 2-ethynylaniline, 3-ethynylaniline, 4-ethynylaniline, 2,4-diethynylaniline, 2,5-diethynylaniline, 2,6-diethynylaniline, 3,4-diethynylaniline, 3,5-diethynylaniline, 1-ethynyl-2-aminonaphthalene, 1-ethynyl-3-aminonaphthalene, 1-ethynyl-4-aminonaphthalene, 1-ethynyl-5-aminonaphthalene, 1-ethynyl-6-aminonaphthalene, 1-ethynyl-7-aminonaphthalene, 1-ethynyl-8-aminonaphthalene, 2-ethynyl-1-aminonaphthalene, 2-ethynyl-3-aminonaphthalene, 2-ethynyl-4-aminonaphthalene, 2-ethynyl-5-aminonaphthalene, 2-ethynyl-6-aminonaphthalene, 2-ethynyl-7-aminonaphthalene, 2-ethynyl-8-aminonaphthalene, 3,5-diethynyl-1-aminonaphthalene, 3,5-diethynyl-2-aminonaphthalene, 3,6-diethynyl-1-aminonaphthalene, 3,6-diethynyl-2-aminonaphthalene, 3,7-diethynyl-1-aminonaphthalene, 3,7-diethynyl-2-aminonaphthalene, 4,8-diethynyl-1-aminonaphthalene, and 4,8-diethynyl-2-aminonaphthalene, although not limited thereto. These compounds may be used alone or in combination or two or more kinds.

Examples of the monohydric alcohol used as the sealing agent for the acid anhydride terminal include methanol, ethanol, 1-propanol, 2-propanol, 1-butanol, 2-butanol, 1-pentanol, 2-pentanol, 3-pentanol, 1-hexanol, 2-hexanol, 3-hexanol, 1-heptanol, 2-heptanol, 3-heptanol, 1-octanol, 2-octanol, 3-octanol, 1-nonanol, 2-nonanol, 1-decanol, 2-decanol, 1-undecanol, 2-undecanol, 1-dodecanol, 2-dodecanol, 1-tridecanol, 2-tridecanol, 1-tetradecanol, 2-tetradecanol, 1-pentadecanol, 2-pentadecanol, 1-hexadecanol, 2-hexadecanol, 1-heptadecanol, 2-heptadecanol, 1-octadecanol, 2-octadecanol, 1-nonadecanol, 2-nonadecanol, 1-icosanol, 2-methyl-1-propanol, 2-methyl-2-propanol, 2-methyl-1-butanol, 3-methyl-1-butanol, 2-methyl-2-butanol, 3-methyl-2-butanol, 2-propyl-1-pentanol, 2-ethyl-l-hexanol, 4-methyl-3-heptanol, 6-methyl-2-heptanol, 2,4,4-trimethyl-1-hexanol, 2,6-dimethyl-4-heptanol, isononyl alcohol, 3,7-dimethyl-3-octanol, 2,4-dimethyl-1-heptanol, 2-heptylundecanol, ethylene glycol monoethyl ether, ethylene glycol monomethyl ether, ethylene glycol monobutyl ether, propylene glycol 1-methyl ether, diethylene glycol monoethyl ether, diethylene glycol monomethyl ether, diethylene glycol monobutyl ether, cyclopentanol, cyclohexanol, cyclopentane monomethylol, dicyclopentane monomethylol, tricyclodecane monomethylol, norborneol, and terpineol, although not limited thereto. These compounds may be used alone or in combination or two or more kinds.

Examples of the acid anhydride, the monocarboxylic acid, the monoacid chloride compound, and the mono-active ester compound used as the sealing agent for terminal amino groups include acid anhydrides such as phthalic anhydride, maleic anhydride, nadic anhydride, cyclohexanedicarboxylic anhydride, and 3-hydroxyphthalic anhydride; monocarboxylic acids such as 2-carboxyphenol, 3-carboxyphenol, 4-carboxyphenol, 2-carboxythiophenol, 3-carboxythiophenol, 4-carboxythiophenol, 1-hydroxy-8-carboxynaphthalene, 1-hydroxy-7-carboxynaphthalene, 1-hydroxy-6-carboxynaphthalene, 1-hydroxy-5-carboxynaphthalene, 1-hydroxy-4-carboxynaphthalene, 1-hydroxy-3-carboxynaphthalene, 1-hydroxy-2-carboxynaphthalene, 1-mercapto-8-carboxynaphthalene, 1-mercapto-7-carboxynaphthalene, 1-mercapto-6-carboxynaphthalene, 1-mercapto-5-carboxynaphthalene, 1-mercapto-4-carboxynaphthalene, 1-mercapto-3-carboxynaphthalene, 1-mercapto-2-carboxynaphthalene, 2-carboxybenzenesulfonic acid, 3-carboxybenzenesulfonic acid, 4-carboxybenzenesulfonic acid, 2-ethynylbenzoic acid, 3-ethynylbenzoic acid, 4-ethynylbenzoic acid, 2,4-diethynylbenzoic acid, 2,5-diethynylbenzoic acid, 2,6-diethynylbenzoic acid, 3,4-diethynylbenzoic acid, 3,5-diethynylbenzoic acid, 2-ethynyl-1-naphthoic acid, 3-ethynyl-1-naphthoic acid, 4-ethynyl-1-naphthoic acid, 5-ethynyl-1-naphthoic acid, 6-ethynyl-1-naphthoic acid, 7-ethynyl-1-naphthoic acid, 8-ethynyl-1-naphthoic acid, 2-ethynyl-2-naphthoic acid, 3-ethynyl-2-naphthoic acid, 4-ethynyl-2-naphthoic acid, 5-ethynyl-2-naphthoic acid, 6-ethynyl-2-naphthoic acid, 7-ethynyl-2-naphthoic acid, and 8-ethynyl-2-naphthoic acid and monoacid chloride compounds obtained by acid-chloridizing carboxyl groups of the above monocarboxylic acids; monoacid chloride compounds obtained by acid-chloridizing only a monocarboxyl group of dicarboxylic acids such as terephthalic acid, phthalic acid, maleic acid, cyclohexanedicarboxylic acid, 3-hydroxyphthalic acid, 5-norbornene-2,3-dicarboxylic acid, 1,2-dicarboxynaphthalene, 1,3-dicarboxynaphthalene, 1,4-dicarboxynaphthalene, 1,5-dicarboxynaphthalene, 1,6-dicarboxynaphthalene, 1,7-dicarboxynaphthalene, 1,8-dicarboxynaphthalene, 2,3-dicarboxynaphthalene, 2,6-dicarboxynaphthalene, and 2,7-dicarboxynaphthalene; and active ester compounds obtained by reaction of a monoacid chloride compound with N-hydroxybenzotriazole or N-hydroxy-5-norbornene-2,3-dicarboxyimide.

Examples of the dicarbonic acid ester used as the sealing agent for terminal amino groups include di-tert-butyl dicarbonate, dibenzyl dicarbonate, dimethyl dicarbonate, and diethyl dicarbonate.

Examples of the vinyl ether compound used as the sealing agent for terminal amino groups include chloroformic acid esters such as tert-butyl chloroformate, n-butyl chloroformate, isobutyl chloroformate, benzyl chloroformate, allyl chloroformate, ethyl chloroformate, and isopropyl chloroformate; isocyanate compounds such as butyl isocyanate, 1-naphthyl isocyanate, octadecyl isocyanate, and phenyl isocyanate; butyl vinyl ether, cyclohexyl vinyl ether, ethyl vinyl ether, 2-ethylhexyl vinyl ether, isobutyl vinyl ether, isopropyl vinyl ether, n-propyl vinyl ether, tert-butyl vinyl ether, and benzyl vinyl ether.

Examples of other compounds used as the sealing agent for terminal amino groups include benzoyl chloride, fluorenylmethyl chloroformate, 2,2,2-trichloroethyl chloroformate, methanesulfonyl chloride, p-toluenesulfonyl chloride, and phenyl isocyanate.

The introduction rate of the sealing agent for acid anhydride terminal is preferably 0.1 to 60 mol %, more preferably 5 to 50 mol %, much more preferably 5 to 20 mol %, with respect to tetracarboxylic dianhydride components corresponding to the general formula (13), which are a raw material of the inventive polyimide precursor polymer. Additionally, the introduction rate of the sealing agent for terminal amino groups is preferably 0.1 to 100 mol %, particularly preferably 5 to 90 mol %, with respect to diamine components. Moreover, multiple different terminal groups may be introduced by reaction with multiple terminal sealing agents.

The inventive polyimide precursor polymer may contain, in addition to the structural unit shown by the general formula (7) and the structural unit shown by the general formula (8), other polyimide precursor structural units, polyimide structural units, polybenzoxazole structural units, and polybenzoxazole precursor structural units.

[Negative Photosensitive Resin Composition]

Then, a photosensitive resin composition using the inventive polyimide precursor polymer as a base resin will be described. In the present invention, a negative photosensitive resin composition can be obtained by using the inventive polyimide precursor polymer as a base resin. In the following, a photosensitive resin composition using the inventive polyimide precursor polymer as a base resin, more specifically, a negative photosensitive resin composition that is capable of forming a negative pattern and available for the organic solvent development, will be described. The negative photosensitive resin composition of the present invention can have the following three embodiments, although the composition is not limited thereto.

A negative photosensitive resin composition according to a first embodiment of the present invention contains:

(A) the polyimide precursor polymer having the structural unit shown by the general formula (8);

(B) a photo-radical initiator; and (D) a solvent.

Component (A) in the negative photosensitive resin composition according to the first embodiment is the polyimide precursor polymer having the structural unit shown by the general formula (8) (i.e., the polymer having the structural unit (8)). This polymer has a polymerizable unsaturated linking group in its molecule. Thus, the negative photosensitive resin composition can be obtained by combining this polymer with a photo-radical initiator.

Component (A), the polymer having the structural unit (8), contains $R_1$ as described above. $R_1$ contains a linear, branched, or cyclic alkyl group having 1 to 20 carbon atoms (for example, a perfluoroalkyl group) or an aromatic group in which a part or all of hydrogen atoms is/are substituted with a fluorine atom(s). Generally, most polymers having a polyimide precursor structural unit are soluble only in a polar solvent such as N-methyl-2-pyrrolidone. However, the polyimide precursor structural unit shown by the general formula (7) derived from the tetracarboxylic acid diester compound shown by the general formula (1), which incorporates an Rf group such as a perfluoroalkyl group into a substituent terminal of the polymer, allows the polymer to easily dissolve in a widely used organic solvent, to significantly increase the solubility in the widely used organic solvent, and to form a negative photosensitive resin composition with improved resolution. Furthermore, in the organic solvent development, concerns of swelling can be prevented.

Preferable rate of $R_1$ introduced into component (A) can be expressed by mole number of $R_1$ contained in 100 g of component (A). Specifically, preferable introduction rate of $R_1$, which allows the polymer to easily dissolve in a widely used organic solvent, is 0.02 mol or more and 0.15 mol or less, more preferably 0.02 mol or more and 0.10 mol or less, with respect to 100 g of component (A). The introduction rate of $R_1$ is much more preferably 0.02 mol or more and 0.05 mol or less, with respect to 100 g of component (A). When the introduction rate of $R_1$ is 0.02 mol or more with respect to 100 g of component (A), the solubility in a widely used organic solvent used in the organic solvent development can be improved, and swelling can be easily prevented. On the other hand, the polyimide precursor structural unit undergoes imidization ring-closure reaction by heating for post-curing after patterning. At this time, the introduced $R_1$ is eliminated and removed from the system. Thus, the introduction amount of $R_1$ is preferably 0.15 mol or less since this range prevents significant reduction of the thickness of the formed film.

Component (B) in the negative photosensitive resin composition according to the first embodiment is a photo-radical initiator. The photo-radical initiator may be appropriately selected from compounds conventionally used as a photopolymerization initiator for UV curing. Examples of the photo-radical initiator include benzophenone derivatives such as benzophenone, methyl o-benzoylbenzoate, 4-benzoyl-4'-methyl diphenyl ketone, dibenzyl ketone, and fluorenone; acetophenone derivatives such as 2,2'-diethoxyacetophenone, 2-hydroxy-2-methylpropiophenone, 1-hydroxycyclohexyl phenyl ketone; thioxanthone derivatives such as thioxanthone, 2-methylthioxanthone, 2-isopropylthioxanthone, and diethylthioxanthone; benzyl derivatives such as benzyl, benzyl dimethyl ketal and benzyl-β-methoxyethyl acetal; benzoin derivatives such as benzoin and benzoin methyl ether; oximes such as 1-phenyl-1,2-butanedione-2-(O-methoxycarbonyl) oxime, 1-phenyl-1,2-propanedione-2-(O-methoxycarbonyl) oxime, 1-phenyl-1,2-propanedione-2-(O-ethoxycarbonyl) oxime, 1-phenyl-1,2-propanedione-2-(O-benzoyl) oxime, 1,3-diphenylpropanetrione-2-(O-ethoxycarbonyl) oxime, and 1-phenyl-3-ethoxypropanetrione-2-(O-benzoyl) oxime; N-arylglycines such as N-phenylglycine; peroxides such as benzoyl perchloride; and aromatic biimidazoles, although not limited thereto. These compounds may be used alone or in combination or two or more kinds. Among the above photo-radical initiators, oximes are particularly preferable in view of photosensitivity.

The formulation amount of component (B) is preferably 0.1 part by mass to 20 parts by mass, more preferably 2 parts by mass to 15 parts by mass, with respect to 100 parts by mass of component (A), the inventive polyimide precursor polymer, in view of photosensitivity. A negative photosensitive resin composition obtained by blending 0.1 part by mass or more of component (B) to 100 parts by mass of component (A) has excellent photosensitivity; a negative photosensitive resin composition obtained by blending 20 parts by mass or less of component (B) to 100 parts by mass of component (A) has excellent thick film curability.

Component (D) in the negative photosensitive resin composition according to the first embodiment is a solvent. The solvent of component (D) is not limited as long as it can dissolve component (A) and component (B). Examples of the solvent include ketones such as cyclohexanone, cyclopentanone, and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, and γ-butyrolactone; and amide solvents such as N-methyl-2-pyrrolidone, N,N-dimethylacetamide, and N,N-dimethylformamide; and these may be used one or more kinds. Among them, ethyl lactate, cyclohexanone, cyclopentanone, propylene glycol monomethyl ether acetate, and γ-butyrolactone, N-methyl-2-pyrrolidone, or a mixture thereof are particularly preferable.

The formulation amount of component (D) is preferably 50 to 2,000 parts by mass, more preferably 100 to 1,000 parts by mass, with respect to 100 parts by mass of the total amount of component (A) and component (B).

The negative photosensitive resin composition according to the first embodiment may further contain other components besides components (A), (B), and (D). Examples of the other components include (F) a sensitizer, an adhesion assistant, a polymerization inhibitor for enhancing storage stability, and (G) a surfactant conventionally used for improving coating property.

Examples of (F) the sensitizer include 7-N,N-diethylaminocoumarin, 7-diethylamino-3-thenonylcoumarin, 3,3'-carbonylbis(7-N,N-diethylamino)coumarin, 3,3'-carbonylbis(7-N,N-dimethoxy)coumarin, 3-thienylcarbonyl-7-N,N-diethylaminocoumarin, 3-benzoylcoumarin, 3-benzoyl-7-N,N-methoxycoumarin, 3-(4'-methoxybenzoyl)coumarin, 3,3'-carbonylbis-5,7-(dimethoxy)coumarin, benzalacetophenone, 4'-N,N-dimethylaminobenzalacetophenone, 4'-acetaminobenzal-4-methoxyacetophenone, dimethylaminobenzophenone, diethylaminobenzophenone, and 4,4'-bis(N-ethyl,N-methyl)benzophenone. The amount thereof is preferably 0.05 to 20 parts by mass, more preferably 0.1 to 10 parts by mass, with respect to 100 parts by mass of the inventive polyimide precursor polymer.

(G) the surfactant is preferably a nonionic surfactant such as a fluorinated surfactant. Illustrative examples thereof include perfluoroalkyl polyoxyethylene ethanol, fluorinated alkyl ester, perfluoroalkylamine oxide, and a fluorine-containing organosiloxane compound.

The surfactant may be commercially available products, and illustrative examples thereof include Flolade "FC-4430" (available from Sumitomo 3M Ltd.), Surflon "S-141" and "S-145" (both are available from Asahi Glass Co., Ltd.), Unidyne "DS-401", "DS-4031", and "DS-451" (all are available from Daikin Industries, Ltd.), Megafac "F-8151" (available from DIC Co.), and "X-70-093" (available from Shin-Etsu Chemical Co., Ltd.). Among them, Flolade "FC-4430" (available from Sumitomo 3M Ltd.) and "X-70-093" (available from Shin-Etsu Chemical Co., Ltd.) are preferable.

A negative photosensitive resin composition according to a second embodiment of the present invention contains:

(A') the polymer having the structural unit (7) or the polymer having the structural unit (8);

(B) a photo-radical initiator;

(C) a crosslinking agent having two or more photo-polymerizable unsaturated linking groups per molecule; and (D) a solvent.

Component (A') in the negative photosensitive resin composition according to the second embodiment is the polymer having the structural unit (7) or the polymer having the structural unit (8). The polymer having the structural unit (7) can have no polymerizable or crosslinkable structure in its polymer molecule. Thus, the negative photosensitive resin composition according to the second embodiment can be formed by adding a crosslinking agent having polymerizable unsaturated linking groups of component (C). On the other hand, the polymer having the structural unit (8) already has a polymerizable unsaturated linking group in its polymer molecule, but an additional crosslinking agent may be added.

The polymer of component (A') contains $R_1$ as described above. $R_1$ contains a linear, branched, or cyclic alkyl group having 1 to 20 carbon atoms (for example, a perfluoroalkyl group) or an aromatic group in which a part or all of hydrogen atoms is/are substituted with a fluorine atom(s). Generally, most polymers having a polyimide precursor structural unit are soluble only in a polar solvent such as N-methyl-2-pyrrolidone. However, the polyimide precursor structural unit shown by the general formula (7) derived from the tetracarboxylic acid diester compound shown by the general formula (1), which incorporates an Rf group such as a perfluoroalkyl group into a substituent terminal of the polymer, allows the polymer to easily dissolve in a widely used organic solvent, to significantly increase the solubility in the widely used organic solvent used in the organic solvent development, and to form a negative photosensitive resin composition with improved resolution. Furthermore, in the organic solvent development, concerns of swelling can be prevented.

Preferable rate of $R_1$ introduced into component (A') can be expressed by mole number of $R_1$ contained in 100 g of component (A'). Specifically, preferable introduction rate of $R_1$, which allows the polymer to easily dissolve in a widely used organic solvent, is 0.02 mol or more and 0.15 mol or less, more preferably 0.02 mol or more and 0.10 mol or less, with respect to 100 g of component (A'). The introduction rate of $R_1$ is much more preferably 0.02 mol or more and 0.05 mol or less, with respect to 100 g of component (A'). When the introduction rate of $R_1$ is 0.02 mol or more with respect to 100 g of component (A'), the solubility in a widely used organic solvent used in the organic solvent development can be improved, and swelling can be easily prevented. On the other hand, the polyimide precursor structural unit undergoes imidization ring-closure reaction by heating for post-curing after patterning. At this time, the introduced $R_1$ is eliminated and removed from the system. Thus, the introduction amount of $R_1$ is preferably 0.15 mol or less since this range prevents significant reduction of the thickness of the formed film.

Component (B) in the negative photosensitive resin composition according to the second embodiment is a photo-radical initiator. As the photo-radical initiator of component (B), the same compounds as described in the first embodiment can be used.

The formulation amount of component (B) is preferably 0.1 part by mass to 20 parts by mass, more preferably 2 parts by mass to 15 parts by mass, with respect to 100 parts by mass of component (A'), the inventive polyimide precursor polymer, in view of photosensitivity. A negative photosensitive resin composition obtained by blending 0.1 part by mass or more of component (B) to 100 parts by mass of component (A') has excellent photosensitivity; a negative photosensitive resin composition obtained by blending 20 parts by mass or less of component (B) to 100 parts by mass of component (A') has excellent thick film curability.

Component (C) in the negative photosensitive resin composition according to the second embodiment is a crosslinking agent having two or more photo-polymerizable unsaturated linking groups per molecule. The crosslinking agent having two or more photo-polymerizable unsaturated linking groups per molecule is preferably a (meth)acrylic compound. Examples thereof include ethylene glycol diacrylate, ethylene glycol dimethacrylate, polyethylene glycol diacrylate (the number of ethylene glycol units is 2 to 20), polyethylene glycol dimethacrylate (the number of ethylene glycol units is 2 to 20), poly(1,2-propylene glycol) diacrylate, poly(1,2-propylene glycol) dimethacrylate, 1,6-hexanediol diacrylate, neopentyl glycol diacrylate, pentaerythritol diacrylate, trimethylolpropane triacrylate, pentaerythritol triacrylate, dipentaerythritol hexaacrylate, tetramethylolpropane tetraacrylate, tetraethylene glycol diacrylate, 1,6-hexanediol dimethacrylate, neopentyl glycol dimethacrylate, pentaerythritol dimethacrylate, trimethylolpropane trimethacrylate, pentaerythritol trimethacrylate, dipentaerythritol hexamethacrylate, tetramethylolpropane tetramethacrylate, glycerol diacrylate, glycerol dimethacrylate, methylene bisacrylamide, N-methylol acrylamide, a methacrylic acid adduct of ethylene glycol diglycidyl ether, an acrylic acid adduct of glycerol diglycidyl ether, an acrylic acid adduct of bisphenol A diglycidyl ether, a methacrylic acid adduct of bisphenol A diglycidyl ether, and N,N'-bis (2-methacryloyloxyethyl) urea, although not limited thereto.

The formulation amount of component (C) is preferably 1 to 100 parts by mass, more preferably 3 to 50 parts by mass, with respect to 100 parts by mass of component (A'). When the amount is in the range of 1 to 100 parts by mass, an intended effect can be sufficiently obtained, and the development ability is not adversely affected. In addition, as a copolymerization monomer, one compound may be used, or a mixture of several compounds may be used.

Component (D) in the negative photosensitive resin composition according to the second embodiment is a solvent. The solvent of component (D) is not limited as long as it can dissolve components (A'), (B), and (C). As the solvent of component (D), the same solvent as described in the first embodiment can be used.

The formulation amount of component (D) is preferably 50 to 2,000 parts by mass, particularly preferably 100 to 1,000 parts by mass, with respect to 100 parts by mass of the total amount of components (A'), (B), and (C).

The negative photosensitive resin composition according to the second embodiment may further contain other components besides components (A'), (B), (C), and (D). Examples of the other components include the same materials as described in the first embodiment.

A negative photosensitive resin composition 000according to a third embodiment of the present invention contains:

(A') the polymer having the structural unit (7) or the polymer having the structural unit (8);

(B') a photo acid generator;

(C') one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms having a glycidyl group as shown by the following formula (C-2),

(C-1)

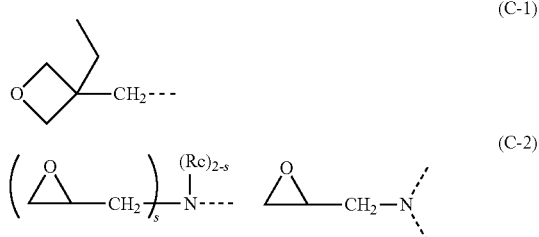

(C-2)

wherein the dotted line represents a bond, Rc represents a linear, branched, or cyclic alkyl group having 1 to 6 carbon atoms, and "s" represents 1 or 2; and (D) a solvent.

The component (A') in the negative photosensitive resin composition according to the third embodiment is the polymer having the structural unit (7) or the structural unit (8), and the same polymer as described in the negative photosensitive resin composition according to the second embodiment can be suitably used.

Component (B') in the negative photosensitive resin composition according to the third embodiment is a photo acid generator. The photo acid generator may be a compound capable of generating an acid by exposure to light having a wavelength of 190 to 500 nm for serving as a curing catalyst. Examples thereof include onium salts, diazomethane derivatives, glyoxime derivatives, β-ketosulfone derivatives, disulfone derivatives, nitrobenzylsulfonate derivatives, sulfonate ester derivatives, imide-yl-sulfonate derivatives, oximesulfonate derivatives, iminosulfonate derivatives, and triazine derivatives.

Examples of the onium salt include a compound shown by the following general formula (20), $$(R_8)_j M^+ K^- \qquad (20)$$

wherein $R_8$ represents an optionally substituted linear, branched, or cyclic alkyl group having 1 to 12 carbon atoms, aryl group having 6 to 12 carbon atoms, or aralkyl group having 7 to 12 carbon atoms; $M^+$ represents an iodonium ion or a sulfonium ion; $K^-$ represents a non-nucleophilic counter ion; and "j" represents 2 or 3.

As to $R_8$, examples of the alkyl group include a methyl group, an ethyl group, a propyl group, a butyl group, a cyclohexyl group, a 2-oxocyclohexyl group, a norbornyl group, and an adamantyl group. Examples of the aryl group include a phenyl group; alkoxyphenyl groups such as an o-, m-, or p-methoxyphenyl group, an o-, m-, or p-ethoxyphenyl group, and a m- or p-tert-butoxyphenyl group; and alkylphenyl groups such as a 2-, 3-, or 4-methylphenyl group, a 2-, 3-, or 4-ethylphenyl group, a 4-tert-butylphenyl group, a 4-butylphenyl group, and a dimethylphenyl group. Examples of the aralkyl group include a benzyl group and a phenethyl group.

Examples of the non-nucleophilic counter ion $K^-$ include halide ions such as a chloride ion and a bromide ion; fluoroalkyl sulfonates such as triflate, 1,1,1-trifluoroethane sulfonate, and nonafluorobutanesulfonate; aryl sulfonates such as tosylate, benzenesulfonate, 4-fluorobenzenesulfonate, and 1,2,3,4,5-pentafluorobenzenesulfonate; and alkyl sulfonates such as mesylate and butanesulfonate.

Examples of the diazomethane derivative include a compound shown by the general formula (21),

wherein $R_9$ is the same or different and represents a linear, branched, or cyclic alkyl group or halogenated alkyl group having 1 to 12 carbon atoms, an aryl group or halogenated aryl group having 6 to 12 carbon atoms, or an aralkyl group having 7 to 12 carbon atoms.

As to $R_9$, examples of the alkyl group include a methyl group, an ethyl group, a propyl group, a butyl group, an amyl group, a cyclopentyl group, a cyclohexyl group, a norbornyl group, and an adamantyl group. Examples of the halogenated alkyl group include a trifluoromethyl group, a 1,1,1-trifluoroethyl group, a 1,1,1-trichloroethyl group, and a nonafluorobutyl group. Examples of the aryl group include a phenyl group; alkoxyphenyl groups such as an o-, m-, or p-methoxyphenyl group, an o-, m-, or p-ethoxyphenyl group, and a m- or p-tert-butoxyphenyl group; and alkylphenyl groups such as a 2-, 3-, or 4-methylphenyl group, a 2-, 3-, or 4-ethylphenyl group, a 4-tert-butylphenyl group, a 4-butylphenyl group, and a dimethylphenyl group. Examples of the halogenated aryl group include a fluorophenyl group, a chlorophenyl group, and a 1,2,3,4,5-pentafluorophenyl group. Examples of the aralkyl group include a benzyl group and a phenethyl group.

Illustrative examples of the photo acid generator include onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl) diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, and diphenyl(4-thiophenoxyphenyl)sulfonium hexafluoroantimonate; diazomethane derivatives such as bis(benzenesulfonyl) diazomethane, bis(p-toluenesulfonyl) diazomethane, bis(xylenesulfonyl) diazomethane, bis(cyclohexylsulfonyl) diazomethane, bis(cyclopentylsulfonyl) diazomethane, bis(n-butylsulfonyl) diazomethane, bis(isobutylsulfonyl) diazomethane, bis(sec-butylsulfonyl) diazomethane, bis(n-propylsulfonyl) diazomethane, bis(isopropylsulfonyl) diazomethane, bis(tert-butylsulfonyl) diazomethane, bis(n-amylsulfonyl) diazomethane, bis(isoamylsulfonyl) diazomethane, bis(sec-amylsulfonyl) diazomethane, bis (tert-amylsulfonyl) diazomethane, 1-cyclohexylsulfonyl-1-(tert-butylsulfonyl) diazomethane, 1-cyclohexylsulfonyl-1-(tert-amylsulfonyl) diazomethane, and 1-tert-amylsulfonyl-1-(tert-butylsulfonyl) diazomethane; glyoxime derivatives such as bis-o-(p-toluenesulfonyl)-α-dimethyl glyoxime, bis-o-(p-toluenesulfonyl)-α-diphenyl glyoxime, bis-o-(p-toluenesulfonyl)-α-dicyclohexyl glyoxime, bis-o-(p-toluenesulfonyl)-2,3-pentanedione glyoxime, bis-(p-toluenesulfonyl)-2-methyl-3,4-pentanedione glyoxime, bis-o-(n-butanesulfonyl)-α-dimethyl glyoxime, bis-o-(n-butanesulfonyl)-α-diphenyl glyoxime, bis-o-(n-butanesulfonyl)-α-dicyclohexyl glyoxime, bis-o-(n-butanesulfonyl)-2,3-pentanedione glyoxime, bis-o-(n-butanesulfonyl)-2-methyl-3,4-pentanedione glyoxime, bis-o-(methanesulfonyl)-α-dimethyl glyoxime, bis-o-(trifluoromethanesulfonyl)-α-dimethyl glyoxime, bis-o-(1,1,1-trifluoroethanesulfonyl)-α-dimethyl glyoxime, bis-o-(tert-butanesulfonyl)-α-dimethyl glyoxime, bis-o-(perfluorooctanesulfonyl)-α-dimethyl glyoxime, bis-o-(cyclohexanesulfonyl)-α-dimethyl glyoxime, bis-o-(benzenesulfonyl)-α-dimethyl glyoxime, bis-o-(p-fluorobenzenesulfonyl)-α-dimethyl glyoxime, bis-o-(p-tert-butylbenzenesulfonyl)-α-dimethyl glyoxime, bis-o-(xylenesulfonyl)-α-dimethyl glyoxime, and bis-o-(camphersulfonyl)-α-dimethyl glyoxime; oxime sulfonate derivatives such as α-(benzenesulfoniumoxyimino)-4-methylphenylacetonitrile; β-keto sulfone derivatives such as 2-cyclohexylcarbonyl-2-(p-toluenesulfonyl) propane and 2-isopropylcarbonyl-2-(p-toluenesulfonyl) propane; disulfone derivatives such as diphenyl disulfone and dicyclohexyl disulfone; nitrobenzyl sulfonate derivatives such as 2,6-dinitrobenzyl p-toluenesulfonate and 2,4-dinitrobenzyl p-toluenesulfonate; sulfonate ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; imide-yl-sulfonate derivatives such as phthalimide-yl-triflate, phthalimide-yl-tosylate, 5-norbornene 2,3-dicarboxyimide-yl-triflate, 5-norbornene 2,3-dicarboxyimide-yl-tosylate, 5-norbornene 2,3-dicarboxyimide-yl-n-butylsulfonate, and n-trifluoromethylsulfonyloxy naphthylimide; iminosulfonates such as (5-(4-methylphenyl)sulfonyloxyimino-5H-thiophene-2-ylidene)-(2-methylphenyl)acetonitrile and (5-(4-(4-methylphenylsulfonyloxy)phenylsulfonyloxyimino)-5H-thiophene-2-ylidene)-(2-methylphenyl)acetonitrile; and 2-methyl-2[(4-methylphenyl)sulfonyl]-1-[(4-methylthio)phenyl]-1-propane. Among them, imide-yl-sulfonates, iminosulfonates, and oxime sulfonates are preferably used. These photo acid generators may be used alone or in combination of two or more kinds.

The formulation amount of the photo acid generator is preferably 0.05 to 20 parts by mass, particularly preferably 0.2 to 5 parts by mass, with respect to 100 parts by mass of component (A') in the negative photosensitive resin composition according to the third embodiment of the present invention in view of light absorption of the photo acid generator itself and photo-curability of a thick film.

Component (C') in the negative photosensitive resin composition according to the third embodiment is one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms having a glycidyl group as shown by the following formula (C-2),

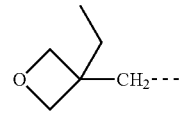
(C-1)

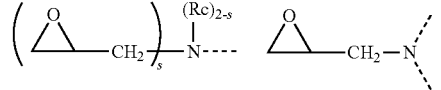
(C-2)

wherein the dotted line represents a bond, Rc represents a linear, branched, or cyclic alkyl group having 1 to 6 carbon atoms, and "s" represents 1 or 2.

Examples of the amino condensate modified with formaldehyde or formaldehyde-alcohol include melamine condensates modified with formaldehyde or formaldehyde-alcohol and urea condensates modified with formaldehyde or formaldehyde-alcohol.

The melamine condensate modified with formaldehyde or formaldehyde-alcohol can be prepared by the following procedure, for example. First, a melamine monomer is modified with formalin into a methylol form, and optionally, the resultant compound is further modified with alcohol into an alkoxy form, according to a known method, to obtain a modified melamine shown by the following general formula (22). The alcohol is preferably a lower alcohol, for example, an alcohol having 1 to 4 carbon atoms.

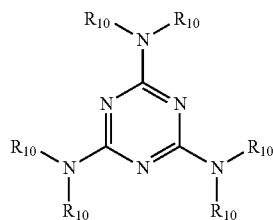
(22)

wherein $R_{10}$ is the same or different and represents a methylol group, an alkoxymethyl group containing an alkoxy group having 1 to 4 carbon atoms, or a hydrogen atom, provided that one or more of $R_{10}$ is a methylol group or an alkoxymethyl group.

Examples of $R_{10}$ include a methylol group, and alkoxymethyl groups such as a methoxymethyl group and an ethoxymethyl group, and a hydrogen atom.

Illustrative examples of the modified melamine shown by the general formula (22) include trimethoxymethyl monomethylol melamine, dimethoxymethyl monomethylol melamine, trimethylol melamine, hexamethylol melamine, and hexamethoxymethylol melamine.

Then, the modified melamine shown by the formula (22) or a multimeric compound thereof (e.g. an oligomer such as a dimer and a trimer) is polymerized by addition condensation with formaldehyde until a desired molecular weight is achieved according to a known method, to obtain the melamine condensate modified with formaldehyde or formaldehyde-alcohol.

The urea condensate modified with formaldehyde or formaldehyde-alcohol can be prepared by modifying a urea condensate having a desired molecular weight with formaldehyde into a methylol form, and optionally, further modifying the resultant compound with alcohol into an alkoxy form, according to a known method.

Illustrative examples of the urea condensate modified with formaldehyde or formaldehyde-alcohol include a methoxymethylated urea condensate, an ethoxymethylated urea condensate, and a propoxymethylated urea condensate.

These modified melamine condensates and modified urea condensates may be used alone or in combination of two or more kinds.

Examples of the phenol compound having on average two or more methylol groups or alkoxymethylol groups per molecule include (2-hydroxy-5-methyl)-1,3-benzenedimethanol, 2,2',6,6'-tetramethoxymethyl bisphenol A, and compounds shown by the formulae (C-3) to (C-7).

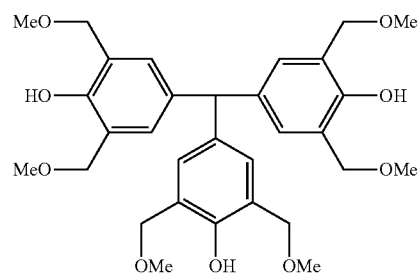
C-3

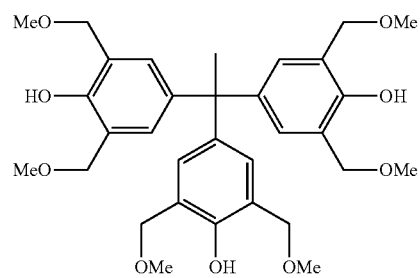
C-4

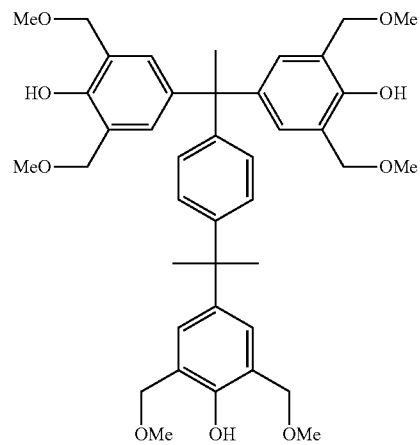
C-5

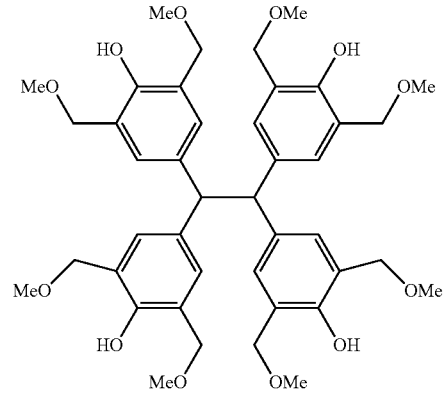
C-6

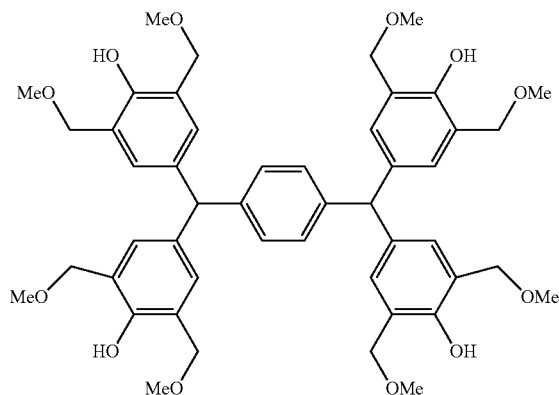

C-7

The above crosslinking agents may be used alone or in combination of two or more kinds.

Examples of the polyhydric phenol compound in which a hydrogen atom of a phenolic hydroxyl group is substituted with a glycidyl group include compounds obtained by reacting a hydroxyl group of bisphenol A, tris(4-hydroxyphenyl)methane, or 1,1,1-tris(4-hydroxyphenyl)ethane with epichlorohydrin in the presence of a base catalyst. More specifically, the polyhydric phenol compound in which a hydrogen atom of a phenolic hydroxyl group is substituted with a glycidyl group is preferably, for example, a compounds shown by the formulae (C-8) to (C-14).

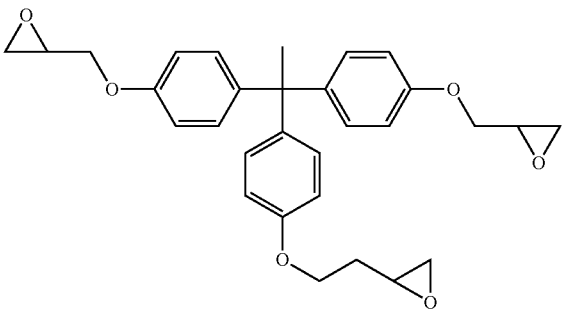

C-11

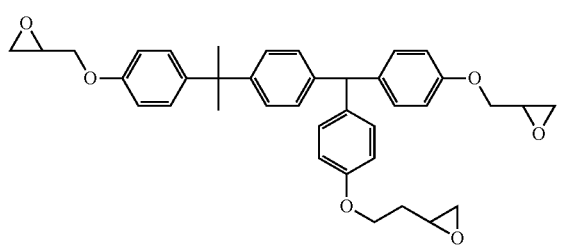

C-12

C-8

C-9

C-10

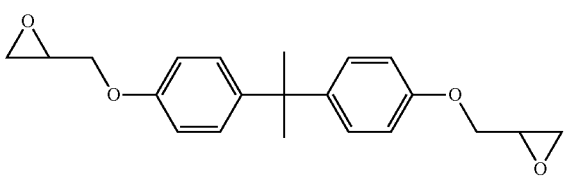

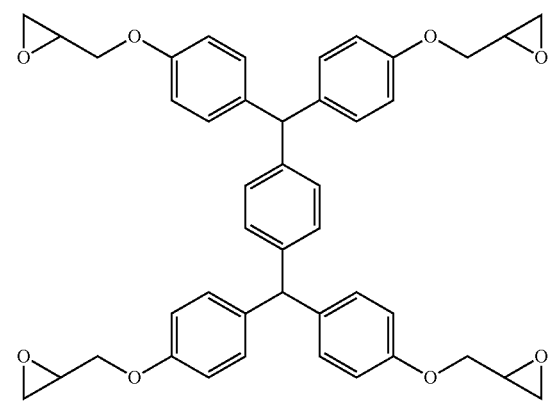

C-13

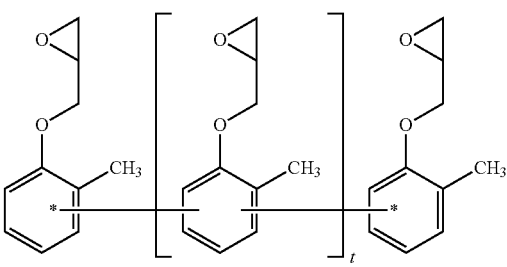

C-14 wherein 2≤t≤3.

The polyhydric phenol compound in which a hydrogen atom of a phenolic hydroxyl group is substituted with a glycidyl group to be used as the crosslinking agent may be one kind or two kinds.

Examples of the polyhydric phenol compound in which a hydrogen atom of a phenolic hydroxyl group is substituted with a substituent shown by the formula (C-1) include a compound having two substituents as shown by the formula (C-15),

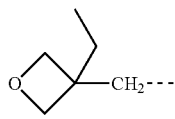
(C-1)

wherein the dotted line represents a bond,

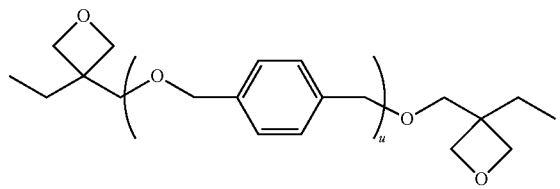
(C-15)

wherein 1≤u≤3.

Examples of the compound containing two or more nitrogen atoms having a glycidyl group as shown by the formula (C-2) include compounds shown by the following formula (C-16),

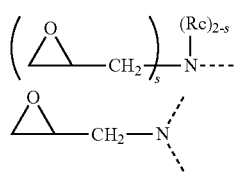
(C-2)

wherein the dotted line represents a bond, Rc represents a linear, branched, or cyclic alkyl group having 1 to 6 carbon atoms, and "s" represents 1 or 2,

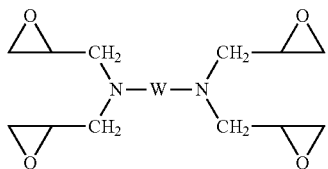
(C-16)

wherein W represents a linear, branched, or cyclic alkylene group having 2 to 12 carbon atoms or a divalent aromatic group.

Examples of the compound shown by the formula (C-16) include compounds shown by the formulae (C-17) to (C-20).

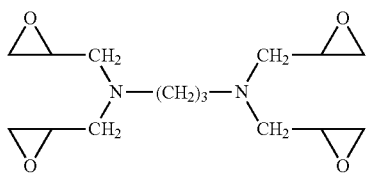
C-17

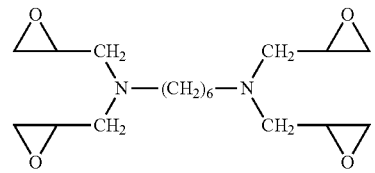
C-18

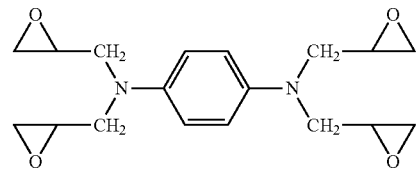
C-19

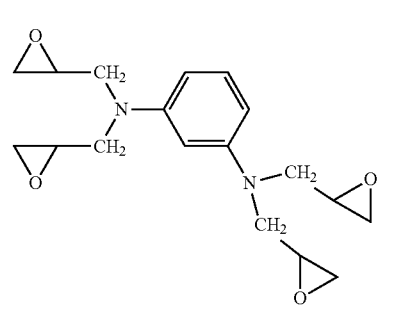
C-20

Alternatively, a compound shown by the following formula (C-21) may be suitably used as the compound containing two or more nitrogen atoms having a glycidyl group as shown by the formula (C-2).

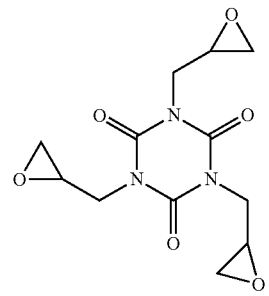
C-21

The compound containing two or more nitrogen atoms having a glycidyl group as shown by the formula (C-2) to be used as the crosslinking agent may be one kind or two kinds.

Component (C'), which serves to initiate curing reaction with the inventive polyimide precursor polymer, not only facilitates pattern formation but also improves the strength of a cured product. The weight average molecular weight of component (C') is preferably 150 to 10,000, particularly preferably 200 to 3,000, in view of photo-curability and heat resistance.

The formulation amount of component (C') is preferably 0.5 to 50 parts by mass, particularly preferably 1 to 30 parts by mass, with respect to 100 parts by mass of component (A') in the negative photosensitive resin composition according to the third embodiment of the present invention.

Preferable examples of the solvent of component (D) in the negative photosensitive resin composition according to the third embodiment are the same as in the negative photosensitive resin composition according to the first and second embodiments.

The negative photosensitive resin composition according to the third embodiment also may further contain other components besides components (A'), (B'), (C'), and (D). Examples of the other components include (F) a sensitizer, an adhesion assistant, a polymerization inhibitor for enhancing storage stability, and (G) a surfactant for improving coating property. As (F) the sensitizer and (G) the surfactant, the above-described compounds can be suitably used.

Moreover, the negative photosensitive resin composition according to the third embodiment also may further contain (H) a basic compound, if necessary. For the basic compound is suited a compound that can reduce diffusion rate at which acids generated from the photo acid generator are diffused into a resist film. Blending the basic compound enhances resolution, reduces the change of sensitivity after exposure, decreases dependence on a substrate and an environment, and thus improves exposure margin, pattern profile, and the like.

Examples of the basic compound include primary, secondary, and tertiary aliphatic amines, mixed amines, aromatic amines, heterocyclic amines, nitrogen-containing compounds having a carboxyl group, nitrogen-containing compounds having a sulfonyl group, nitrogen-containing compounds having a hydroxyl group, nitrogen-containing compounds having a hydroxyphenyl group, nitrogen-containing alcoholic compounds, amide derivatives, imide derivatives, and compounds shown by the following general formula (23).

$$N(\alpha)_q(\beta)_{3-q} \quad (23)$$

In the formula, "q" represents 1, 2, or 3; the side chain α is the same or different and represents any of substituents shown by the following general formulae (24) to (26); and the side chain β is the same or different and represents a hydrogen atom or a linear, branched, or cyclic alkyl group having 1 to 20 carbon atoms and optionally containing an ether bond or a hydroxyl group. The side chains α may be bonded with each other to form a ring.

(24)

(25)

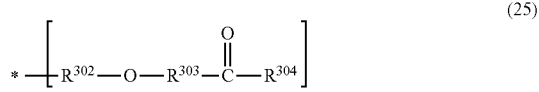
(26)

wherein $R^{300}$, $R^{302}$, and $R^{305}$ represent a linear or branched alkylene group having 1 to 4 carbon atoms; $R^{301}$ and $R^{304}$ represent a hydrogen atom, or a linear, branched, or cyclic alkyl group having 1 to 20 carbon atoms and optionally containing one or more groups selected from a hydroxyl group, an ether bond, an ester bond, and a lactone ring; $R^{303}$ represents a single bond or a linear or branched alkylene group having 1 to 4 carbon atoms; and R306 represents a linear, branched, or cyclic alkyl group having 1 to 20 carbon atoms and optionally containing one or more groups selected from a hydroxyl group, an ether bond, an ester bond, and a lactone ring. * represents a bond terminal.

Examples of the primary aliphatic amine include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine.

Examples of the secondary aliphatic amine include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylene diamine, N,N-dimethylethylene diamine, and N,N-dimethyltetraethylene pentamine.

Examples of the tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylene diamine, N,N,N',N'-tetramethylethylene diamine, and N,N,N',N'-tetramethyltetraethylene pentamine.

Examples of the mixed amines include dimethylethylamine, methylethylpropylamine, benzylamine, phenethylamine, and benzyldimethylamine.

Examples of the aromatic amines and the heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of the nitrogen-containing compound having a carboxyl group include amino benzoic acid, indole carboxylic acid, and amino acid derivatives (e.g., nicotinic acid, alanine, arginine, aspartic acid, glutamic acid, glycine, histidine, isoleucine, glycyl leucine, leucine, methionine, phenylalanine, threonine, lysine, 3-aminopyrazine-2-carboxylic acid, and methoxy alanine).

Examples of the nitrogen-containing compound having a sulfonyl group include 3-pyridinesulfonic acid and pyridinium p-toluenesulfonate.

Examples of the nitrogen-containing compound having a hydroxyl group, the nitrogen-containing compound having a hydroxyphenyl group, and the nitrogen-containing alcoholic compound include 2-hydroxy pyridine, amino cresol, 2,4-quinoline diol, 3-indole methanol hydrate, monoethanol amine, diethanol amine, triethanol amine, N-ethyl diethanol amine, N,N-diethyl ethanol amine, triisopropanol amine, 2,2'-imino diethanol, 2-amino ethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propane diol, 3-pyrrolidino-1,2-propane diol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotine amide.

Examples of the amide derivative include formamide, N-methyl formamide, N,N-dimethyl formamide, acetamide, N-methyl acetamide, N,N-dimethyl acetamide, propione amide, and benzamide.

Examples of the imide derivative include phthalimide, succinimide, and maleimide.

Examples of the compound shown by the general formula (23) include tris[2-(methoxymethoxy)ethyl] amine, tris[2-(2-methoxyethoxy)ethyl] amine, tris[2-(2-methoxyethoxymethoxy)ethyl] amine, tris[2-(1-methoxyethoxy)ethyl] amine, tris[2-(1-ethoxyethoxy)ethyl] amine, tris[2-(1-ethoxypropoxy)ethyl] amine, tris[2-{2-(2-hydroxyethoxy)ethoxy}ethyl] amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl) amine, tris(2-acetoxyethyl) amine, tris(2-propionyloxyethyl) amine, tris(2-butyryloxyethyl) amine, tris(2-isobutyryloxyethyl) amine, tris(2-valeryloxyethyl) amine, tris(2-pivaloyloxyethyl) amine, N,N-bis(2-acetoxyethyl) 2-(acetoxyacetoxy)ethyl amine, tris(2-methoxycarbonyloxyethyl) amine, tris(2-tert-butoxycarbonyloxyethyl) amine, tris[2-(2-oxopropoxy)ethyl] amine, tris[2-(methoxycarbonylmethyl)oxyethyl] amine, tris[2-(tert-butoxycarbonylmethyloxy)ethyl] amine, tris[2-(cyclohexyloxycarbonylmethyloxy)ethyl] amine, tris(2-methoxycarbonylethyl) amine, tris(2-ethoxycarbonylethyl) amine, N,N-bis(2-hydroxyethyl) 2-(methoxycarbonyl)ethyl amine, N,N-bis(2-acetoxyethyl) 2-(methoxycarbonyl)ethyl amine, N,N-bis(2-hydroxyethyl) 2-(ethoxycarbonyl)ethyl amine, N,N-bis(2-acetoxyethyl) 2-(ethoxycarbonyl)ethyl amine, N,N-bis(2-hydroxyethyl) 2-(2-methoxyethoxycarbonyl)ethyl amine, N,N-bis(2-acetoxyethyl) 2-(2-methoxyethoxycarbonyl)ethyl amine, N,N-bis(2-hydroxyethyl) 2-(2-hydroxyethoxycarbonyl)ethyl amine, N,N-bis(2-acetoxyethyl) 2-(2-acetoxyethoxycarbonyl)ethyl amine, N,N-bis(2-hydroxyethyl) 2-[(methoxycarbonyl)methoxycarbonyl]ethyl amine, N,N-bis(2-acetoxyethyl) 2-[(methoxycarbonyl)methoxycarbonyl]ethyl amine, N,N-bis(2-hydroxyethyl) 2-(2-oxopropoxycarbonyl)ethyl amine, N,N-bis(2-acetoxyethyl) 2-(2-oxopropoxycarbonyl)ethyl amine, N,N-bis(2-hydroxyethyl) 2-(tetrahydrofurfuryloxycarbonyl)ethyl amine, N,N-bis(2-acetoxyethyl) 2-(tetrahydrofurfuryloxycarbonyl)ethyl amine, N,N-bis(2-hydroxyethyl) 2-[(2-oxotetrahydrofuran-3-yl)oxycarbonyl]ethyl amine, N,N-bis(2-acetoxyethyl) 2-[(2-oxotetrahydrofuran-3-yl)oxycarbonyl]ethyl amine, N,N-bis(2-hydroxyethyl) 2-(4-hydroxybutoxycarbonyl)ethyl amine, N,N-bis(2-formyloxyethyl) 2-(4-formyloxybutoxycarbonyl)ethyl amine, N,N-bis(2-formyloxyethyl) 2-(2-formyloxyethoxycarbonyl)ethyl amine, N,N-bis(2-methoxyethyl) 2-(methoxycarbonyl)ethyl amine, N-(2-hydroxyethyl) bis[2-(methoxycarbonyl)ethyl] amine, N-(2-acetoxyethyl) bis[2-(methoxycarbonyl)ethyl] amine, N-(2-hydroxyethyl) bis[2-(ethoxycarbonyl)ethyl] amine, N-(2-acetoxyethyl) bis[2-(ethoxycarbonyl)ethyl] amine, N-(3-hydroxy-1-propyl) bis[2-(methoxycarbonyl)ethyl] amine, N-(3-acetoxy-1-propyl) bis[2-(methoxycarbonyl)ethyl] amine, N-(2-methoxyethyl) bis[2-(methoxycarbonyl)ethyl] amine, N-butyl bis[2-(methoxycarbonyl)ethyl] amine, N-butyl bis[2-(2-methoxyethoxycarbonyl)ethyl] amine, N-methyl bis(2-acetoxyethyl) amine, N-ethyl bis(2-acetoxyethyl) amine, N-methyl bis(2-pivaloyloxyethyl) amine, N-ethyl bis[2-(methoxycarbonyloxy)ethyl] amine, N-ethyl bis[2-(tert-butoxycarbonyloxy)ethyl] amine, tris(methoxycarbonylmethyl) amine, tris(ethoxycarbonylmethyl) amine, N-butyl bis(methoxycarbonylmethyl) amine, N-hexyl bis(methoxycarbonylmethyl) amine, and β-(diethylamino)-δ-valerolactone; however, the compound is not limited thereto. These basic compounds may be used alone or in combination of two or more kinds.

The formulation amount of the basic compound is preferably 0 to 3 parts by mass, particularly preferably 0.01 to 1 part by mass, with respect to 100 parts by mass of component (A') in the negative photosensitive resin composition according to the third embodiment of the present invention, in view of sensitivity.

The negative photosensitive resin composition of the present invention can be prepared by a usual method. The negative photosensitive resin composition can be prepared by stirring and mixing the above-described components and then filtering the mixture through a filter.

(Patterning Process)

Then, the patterning processes using the negative photosensitive resin composition of the present invention will be described.

A well-known lithography technology can be employed to form a pattern of the negative photosensitive resin composition of the present invention. For example, the negative photosensitive resin composition may be applied by a spin coating method on a silicon wafer, a $SiO_2$ substrate, a SiN substrate, or a substrate having a formed pattern such as copper wiring, and pre-baked at about 80 to 130° C. for 50 to 600 seconds to form a photosensitive material film with a thickness of 1 to 50 μm, preferably 1 to 30 μm, more preferably 5 to 20 μm.

The spin coating method may be to dispense about 5 mL of the negative photosensitive resin composition on a silicon substrate and then rotate the substrate, thereby applying the negative photosensitive resin composition on the substrate. By adjusting the rotational speed during this operation, the thickness of the photosensitive material film on the substrate can be easily controlled.

Then, a mask for forming an intended pattern is put over the photosensitive material film, and the film is irradiated with a high energy beam having a wavelength of 190 to 500 nm such as i-line beam and g-line beam or an electron beam with an exposure dose of about 1 to 5,000 mJ/cm², preferably about 100 to 2,000 mJ/cm².

Then, if necessary, post exposure bake (PEB) may be carried out on a hot plate at 60 to 150° C. for 1 to 10 minutes, preferably at 80 to 120° C. for 1 to 5 minutes.

Then, development is performed. All of the negative photosensitive resin compositions according to the first, second, and third embodiments of the present invention are available for the organic solvent development.

Examples of the organic solvent usable for the organic solvent development include the above-described solvents used for preparing the negative photosensitive resin composition of the present invention. For example, ketones such as cyclohexanone and cyclopentanone, and glycols such as propylene glycol monomethyl ether are preferable. The development can be performed by a usual method such as spraying, puddling, or soaking in a developer. Then, if necessary, washing, rinsing, drying, and so forth may be performed to obtain a resist film having an intended pattern.

Moreover, the film having a pattern obtained by the patterning process may be baked and post-cured with an oven or a hot plate at 100 to 300° C., preferably 150 to 300° C., more preferably 180 to 250° C. to form a cured film. In this post-curing step, the polyimide precursor structural unit in the inventive polyimide precursor polymer undergoes imidization ring-closure reaction, and the Rf group such as a perfluoroalkyl group is eliminated and removed from the system. When the post-curing temperature is 100 to 300° C., the crosslinking density of the film of the negative photosensitive resin composition can be increased, and remaining volatile components can be removed. Thus, this temperature range is preferable in view of adhesiveness to a substrate, heat resistance, strength, and electronic characteristics. The time for the post-curing can be 10 minutes to 10 hours.

The formed pattern can be used for a top coat coating a wiring, a circuit, and a substrate, etc. Such formed pattern and top coat have excellent insulating property and excellent adhesiveness to a metal layer of, for example, Cu of a wiring and a circuit to be coated, a metal electrode on a substrate, and an insulating substrate such as SiN substrate with a wiring and a circuit to be coated, and can significantly improve resolution capacity for forming a fine pattern with an appropriate mechanical strength as a top coat.

The cured film thus obtained has excellent adhesiveness to a substrate, heat resistance, electric characteristics, mechanical strength, and chemical resistance to an alkaline removing liquid. A semiconductor device using this cured film as a top coat has excellent reliability, and especially, generation of cracks during a thermal cycle test can be prevented. Therefore, this cured film is useful for a top coat to protect electric and electronic parts, semiconductor devices, etc.

The above top coat is useful for an insulator film for a semiconductor device including rewiring use, an insulator film for a multilayer printed substrate, a solder mask, and a cover lay film, because of its heat resistance, chemical resistance, and insulating property.

EXAMPLES

Hereinafter, the present invention will be specifically described with reference to synthesis examples, comparative synthesis examples, examples, and comparative examples, but the present invention is not limited to the following examples.

I. Synthesis of Polyimide Precursor Polymer

Chemical structural formulae of compounds used in the following synthesis examples are shown below.

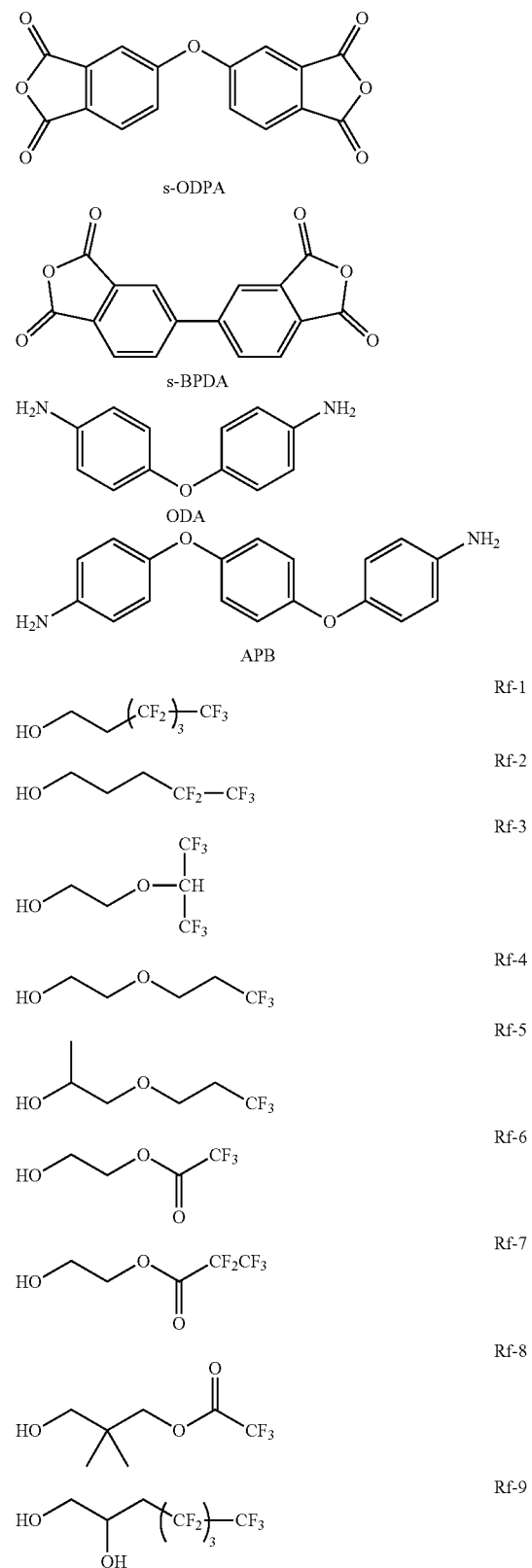

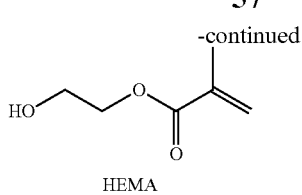

HEMA

[Synthesis Example 1] Synthesis of Tetracarboxylic Acid Diester Compound (X-1)

A 3 L flask equipped with a stirrer and a thermometer was charged with 100 g (340 mmol) of 3,3',4,4'-biphenyltetracarboxylic dianhydride (s-BPDA), 68.8 g (680 mmol) of triethylamine, 41.5 g (340 mmol) of N,N-dimethyl-4-aminopyridine, and 400 g of γ-butyrolactone. To this solution was added dropwise 179.6 g (680 mmol) of 1H,1H,2H,2H-nonafluoro-1-hexanol (Rf-1) under stirring at room temperature, and the solution was further stirred at room temperature for 24 hours. Then, 408 g of 10% hydrochloric acid aqueous solution was added dropwise under ice-cooling to terminate the reaction. To the reaction solution, 800 g of 4-methyl-2-pentanone was added, and the organic layer was collected and washed with 600 g of water 6 times. The solvent of the obtained organic layer was distilled off to obtain 273 g of a tetracarboxylic acid diester compound having the following structure.

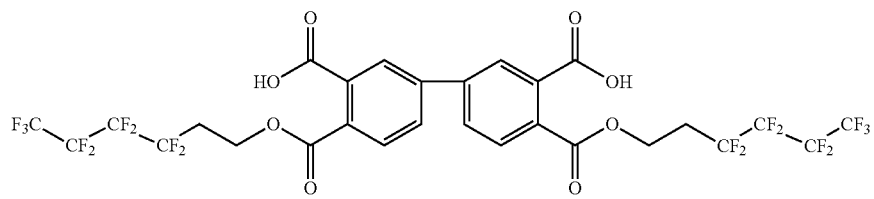 [SMILES: O=C(O)c1cc(-c2ccc(C(=O)OCCC(F)(F)C(F)(F)C(F)(F)C(F)(F)F)c(C(=O)O)c2)ccc1C(=O)OCCC(F)(F)C(F)(F)C(F)(F)C(F)(F)F]

$^1$H-NMR analysis showed the following result and confirmed that the product was a tetracarboxylic acid diester compound (X-1) having the above structure. 13.48 ppm (2H), 7.77-8.09 ppm (6H), 4.55 ppm (4H), 2.77 ppm (4H)

[Synthesis Example 2] Synthesis of Tetracarboxylic Acid Diester Compound (X-2)

218 g of a tetracarboxylic acid diester compound having the following structure was obtained in the same manner as in Synthesis Example 1 except that 1H,1H,2H,2H-nonafluoro-1-hexanol (Rf-1) was changed to 121.1 g (680 mmol) of 4,4,5,5,5-pentafluoropentanol (Rf-2).

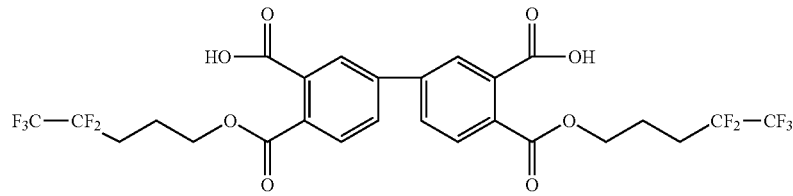 [SMILES: O=C(O)c1cc(-c2ccc(C(=O)OCCCC(F)(F)C(F)(F)F)c(C(=O)O)c2)ccc1C(=O)OCCCC(F)(F)C(F)(F)F]

$^1$H-NMR analysis showed the following result and confirmed that the product was a tetracarboxylic acid diester compound (X-2) having the above structure. 13.40 ppm (2H), 7.77-8.10 ppm (6H), 4.53 ppm (4H), 2.75 ppm (4H), 1.63 ppm (4H)

[Synthesis Example 3] Synthesis of Tetracarboxylic Acid Diester Compound (X-3)

256 g of a tetracarboxylic acid diester compound having the following structure was obtained in the same manner as in Synthesis Example 1 except that 1H,1H,2H,2H-nonafluoro-1-hexanol (Rf-1) was changed to 144.2 g (680 mmol) of 1-trifluoromethyl-2,2,2-trifluoroethyl-2'-hydroxyethylether (Rf-3).

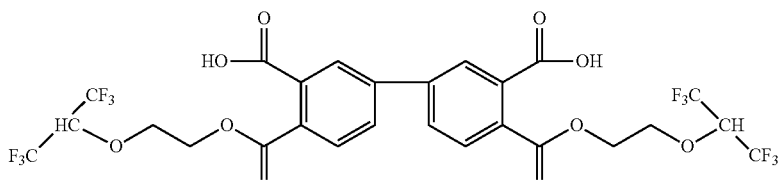

¹H-NMR analysis showed the following result and confirmed that the product was a tetracarboxylic acid diester compound (X-3) having the above structure. 13.40 ppm (2H), 7.93-8.46 ppm (6H), 4.60 ppm (2H), 4.53 ppm (4H), 3.43 ppm (4H)

[Synthesis Example 4] Synthesis of Tetracarboxylic Acid Diester Compound (X-4)

200 g of a tetracarboxylic acid diester compound having the following structure was obtained in the same manner as in Synthesis Example 1 except that 1H,1H,2H,2H-nonafluoro-1-hexanol (Rf-1) was changed to 98.0 g (680 mmol) of 3,3,3-trifluoropropyl-2'-hydroxyethylether (Rf-4).

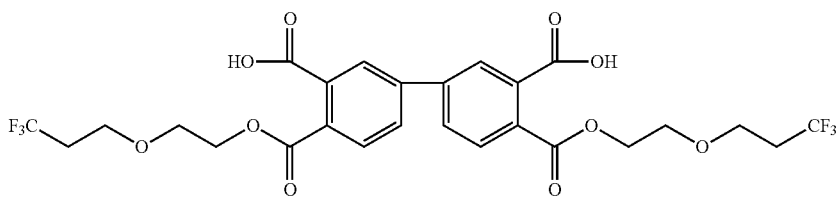 [SMILES: O=C(O)c1cc(-c2ccc(C(=O)OCCOCCC(F)(F)F)c(C(=O)O)c2)ccc1C(=O)OCCOCCC(F)(F)F]

¹H-NMR analysis showed the following result and confirmed that the product was a tetracarboxylic acid diester compound (X-4) having the above structure. 13.40 ppm (2H), 7.80-8.12 ppm (6H), 4.50 ppm (4H), 3.52 ppm (4H), 3.42 ppm (4H), 2.73 ppm (4H)

[Synthesis Example 5] Synthesis of Tetracarboxylic Acid Diester Compound (X-5)

212 g of a tetracarboxylic acid diester compound having the following structure was obtained in the same manner as in Synthesis Example 1 except that 1H,1H,2H,2H-nonafluoro-1-hexanol (Rf-1) was changed to 107.5 g (680 mmol) of 3,3,3-trifluoropropyl-2'-hydroxypropylether (Rf-5).

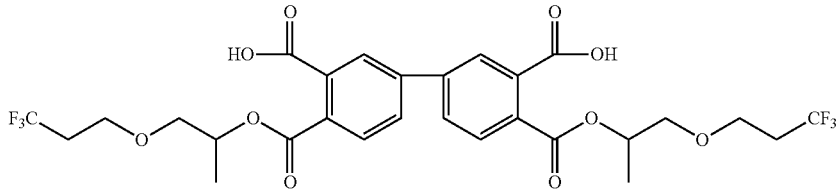 [SMILES: CC(COCCC(F)(F)F)OC(=O)c1ccc(-c2ccc(C(=O)OC(C)COCCC(F)(F)F)c(C(=O)O)c2)cc1C(=O)O]

$^1$H-NMR analysis showed the following result and confirmed that the product was a tetracarboxylic acid diester compound (X-5) having the above structure. 13.38 ppm (2H), 7.77-8.10 ppm (6H), 4.54 ppm (2H), 3.53 ppm (4H), 3.42 ppm (4H), 2.72 ppm (4H), 1.40 ppm (6H)

[Synthesis Example 6] Synthesis of Tetracarboxylic Acid Diester Compound (X-6)

205 g of a tetracarboxylic acid diester compound having the following structure was obtained in the same manner as in Synthesis Example 1 except that 1H,1H,2H,2H-nonafluoro-1-hexanol (Rf-1) was changed to 107.5 g (680 mmol) of 2-hydroxyethyltrifluoroacetate (Rf-6).

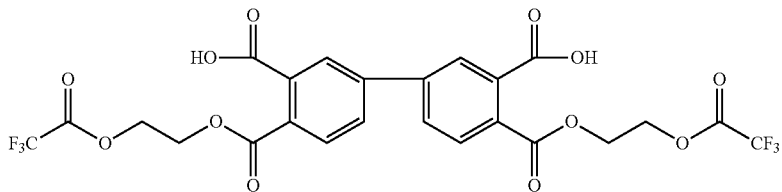 [SMILES: O=C(O)c1cc(-c2ccc(C(=O)OCCOC(=O)C(F)(F)F)c(C(=O)O)c2)ccc1C(=O)OCCOC(=O)C(F)(F)F]

$^1$H-NMR analysis showed the following result and confirmed that the product was a tetracarboxylic acid diester compound (X-6) having the above structure. 13.41 ppm (2H), 7.80-8.20 ppm (6H), 4.55 ppm (4H), 4.53 ppm (4H)

[Synthesis Example 7] Synthesis of Tetracarboxylic Acid Diester Compound (X-7)

228 g of a tetracarboxylic acid diester compound having the following structure was obtained in the same manner as in Synthesis Example 1 except that 1H,1H,2H,2H-nonafluoro-1-hexanol (Rf-1) was changed to 141.5 g (680 mmol) of 2-hydroxyethylpentafluoropropionate (Rf-7).

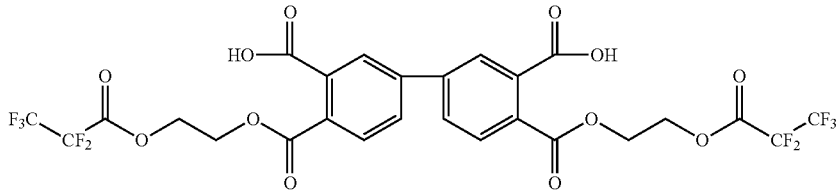 [SMILES: O=C(O)c1cc(-c2ccc(C(=O)OCCOC(=O)C(F)(F)C(F)(F)F)c(C(=O)O)c2)ccc1C(=O)OCCOC(=O)C(F)(F)C(F)(F)F]

$^1$H-NMR analysis showed the following result and confirmed that the product was a tetracarboxylic acid diester compound (X-7) having the above structure. 13.42 ppm (2H), 7.80-8.20 ppm (6H), 4.56 ppm (4H), 4.55 ppm (4H)

[Synthesis Example 8] Synthesis of Tetracarboxylic Acid Diester Compound (X-8)

200 g of a tetracarboxylic acid diester compound having the following structure was obtained in the same manner as in Synthesis Example 1 except that 1H,1H,2H,2H-nonafluoro-1-hexanol (Rf-1) was changed to 200.2 g (680 mmol) of 3-hydroxy-2,2-dimethylpropyltrifluoroacetate (Rf-8).

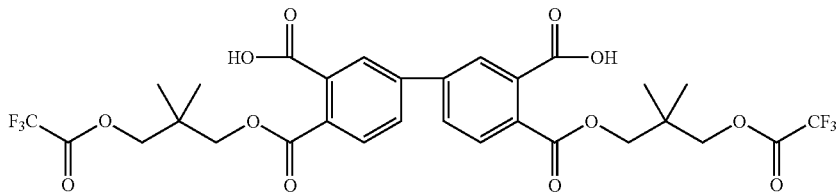 [SMILES: CC(C)(COC(=O)c1ccc(-c2ccc(C(=O)OCC(C)(C)COC(=O)C(F)(F)F)c(C(=O)O)c2)cc1C(=O)O)COC(=O)C(F)(F)F]

¹H-NMR analysis showed the following result and confirmed that the product was a tetracarboxylic acid diester compound (X-8) having the above structure. 13.41 ppm (2H), 7.78-8.12 ppm (6H), 4.53 ppm (4H), 4.50 ppm (4H), 1.11 ppm (12H)

[Synthesis Example 9] Synthesis of Tetracarboxylic Acid Diester Compound (X-9)

200 g of a tetracarboxylic acid diester compound having the following structure was obtained in the same manner as in Synthesis Example 1 except that 1H,1H,2H,2H-nonafluoro-1-hexanol (Rf-1) was changed to 200.0 g (680 mmol) of 4,4,5,5,6,6,7,7,7-nonafluoro-1,2-heptanediol (Rf-9).

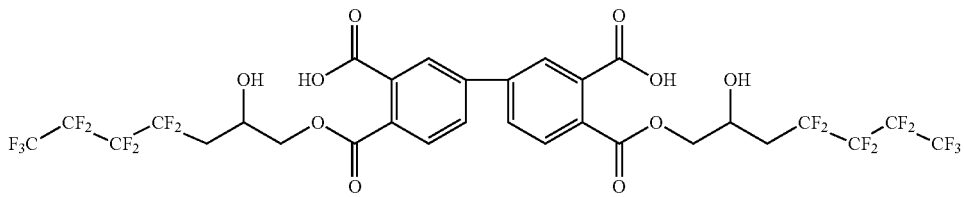 [SMILES: O=C(O)c1cc(-c2ccc(C(=O)OCC(O)CC(F)(F)C(F)(F)C(F)(F)C(F)(F)F)c(C(=O)O)c2)ccc1C(=O)OCC(O)CC(F)(F)C(F)(F)C(F)(F)C(F)(F)F]

¹H-NMR analysis showed the following result and confirmed that the product was a tetracarboxylic acid diester compound (X-9) having the above structure. 13.48 ppm (2H), 7.77-8.09 ppm (6H), 4.57 ppm (4H), 3.81 ppm (2H), 2.78 ppm (4H), 2.10 ppm (2H)

[Synthesis Example 10] Synthesis of Tetracarboxylic Acid Diester Compound (X-10)

A 3 L flask equipped with a stirrer and a thermometer was charged with 100 g (322 mmol) of 3,3',4,4'-oxydiphthalic dianhydride (s-ODPA), 65.2 g (644 mmol) of triethylamine, 39.3 g (322 mmol) of N,N-dimethyl-4-aminopyridine, and 400 g of γ-butyrolactone. To this solution was added dropwise 83.8 g (644 mmol) of hydroxyethyl methacrylate (HEMA) under stirring at room temperature, and the solution was further stirred at room temperature for 24 hours. Then, 370 g of 10% hydrochloric acid aqueous solution was added dropwise under ice-cooling to terminate the reaction. To the reaction solution, 800 g of 4-methyl-2-pentanone was added, and the organic layer was collected and washed with 600 g of water 6 times. The solvent of the obtained organic layer was distilled off to obtain 180 g of a tetracarboxylic acid diester compound (X-10) having the following structure.

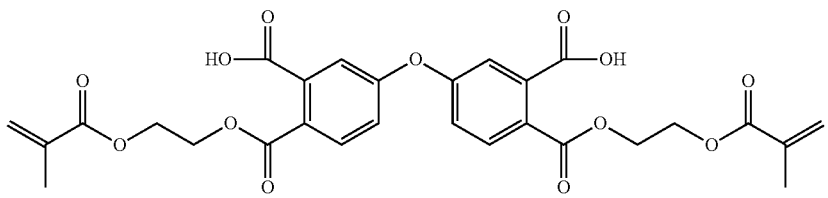 [SMILES: C=C(C)C(=O)OCCOC(=O)c1ccc(Oc2ccc(C(=O)OCCOC(=O)C(=C)C)c(C(=O)O)c2)cc1C(=O)O]

¹H-NMR analysis showed the following result and confirmed that the product was a tetracarboxylic acid diester compound (X-10) having the above structure. 13.34 ppm (2H), 7.25-7.90 ppm (6H), 5.99-6.04 ppm (2H), 5.62 ppm (2H), 4.35-4.51 ppm (8H), 1.80-1.89 ppm (6H)

[Synthesis Example 11] Synthesis of Tetracarboxylic Acid Diester Compound (X-11)

172 g of a tetracarboxylic acid diester compound having the following structure was obtained in the same manner as in Synthesis Example 10 except that 3,3',4,4'-oxydiphthalic dianhydride (s-ODPA) was changed to 94.8 g (322 mmol) of 3,3',4,4'-bisphthalic dianhydride (s-BPDA).

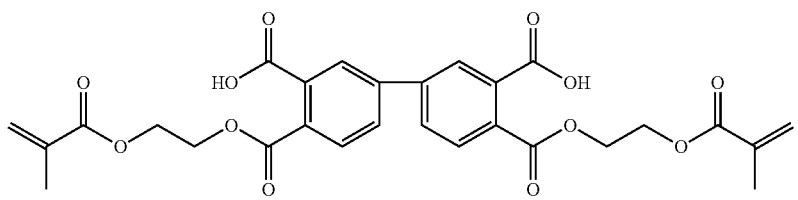 [SMILES: C=C(C)C(=O)OCCOC(=O)c1ccc(-c2ccc(C(=O)OCCOC(=O)C(=C)C)c(C(=O)O)c2)cc1C(=O)O]

¹H-NMR analysis showed the following result and confirmed that the product was a tetracarboxylic acid diester compound (X-11) having the above structure. 13.45 ppm (2H), 7.77-8.09 ppm (6H), 6.05 ppm (2H), 5.66-5.68 ppm (2H), 4.40-4.53 ppm (8H), 1.84-1.87 ppm (6H)

[Synthesis Example 12] Synthesis of Polyimide Precursor Polymer (A-1)

A 1 L flask equipped with a stirrer and a thermometer was charged with 41.1 g (50 mmol) of (X-1), 28.5 g (50 mmol) of (X-10), and 278 g of N-methyl-2-pyrrolidone, and the mixture was stirred and dissolved at room temperature. Then, 24.4 g (205 mmol) of thionyl chloride was added dropwise to the resulting solution under ice-cooling while maintaining the reaction solution temperature at 10° C. or lower. After dropwise addition, the solution was stirred for 2 hours under ice-cooling. Then, a solution in which 19 g (95 mmol) of 4,4'-diaminodiphenyl ether (ODA) and 32.4 g (410 mmol) of pyridine have been dissolved in 76 g of N-methyl-2-pyrrolidone was added dropwise thereto under ice-cooling while maintaining the reaction solution temperature at 10° C. or lower. After dropwise addition, this reaction solution was added dropwise to 3 L of water under stirring at room temperature. The precipitate was then collected by filtration, washed with water as needed, and dried under reduced pressure at 40° C. for 48 hours to obtain the following polyimide precursor polymer (A-1). When the molecular weight of this polymer was measured by GPC, the weight average molecular weight was 15,000 in terms of polystyrene.

In the obtained polymer (A-1), the introduction amount of the fluorine-substituted alkyl group at the substituent terminal was 0.12 mol with respect to 100 g of the polymer.

[Synthesis Example 13] Synthesis of Polyimide Precursor Polymer (A-2)

A polyimide precursor polymer (A-2) was obtained in the same manner as in Synthesis Example 12 except that (X-1) was 24.7 g (30 mmol), and (X-10) was 39.9 g (70 mmol). When the molecular weight of this polymer was measured by GPC, the weight average molecular weight was 17,200 in terms of polystyrene.

In the obtained polymer (A-2), the introduction amount of the alkyl group in which a part or all of hydrogen atoms is/are substituted with a fluorine atom(s) at the substituent terminal was 0.074 mol with respect to 100 g of the polymer.

[Synthesis Example 14] Synthesis of Polyimide Precursor Polymer (A-3)

A polyimide precursor polymer (A-3) was obtained in the same manner as in Synthesis Example 12 except that (X-1) was 16.4 g (20 mmol), and (X-10) was 45.6 g (80 mmol). When the molecular weight of this polymer was measured by GPC, the weight average molecular weight was 16,800 in terms of polystyrene.

In the obtained polymer (A-3), the introduction amount of the alkyl group in which a part or all of hydrogen atoms is/are substituted with a fluorine atom(s) at the substituent terminal was 0.051 mol with respect to 100 g of the polymer.

[Synthesis Example 15] Synthesis of Polyimide Precursor Polymer (A-4)

A polyimide precursor polymer (A-4) was obtained in the same manner as in Synthesis Example 12 except that (X-1)

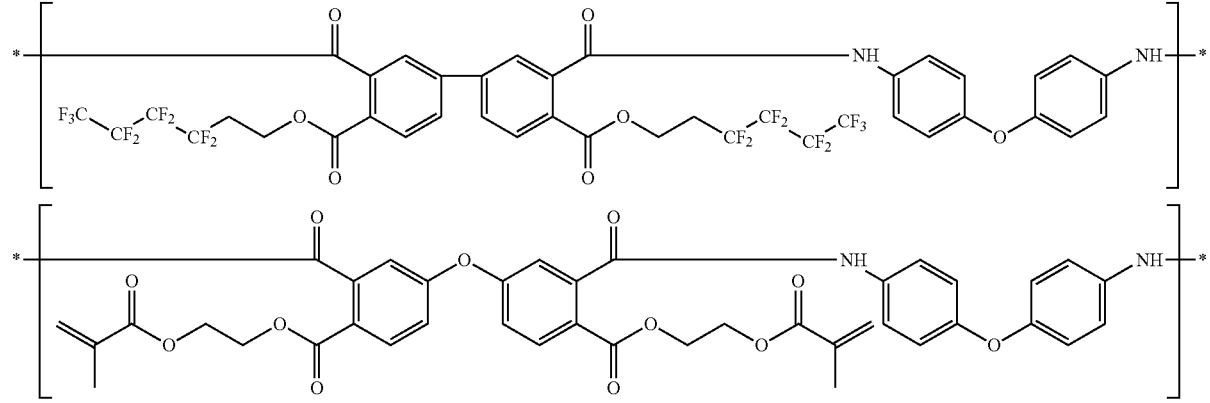

was 8.2 g (10 mmol), and (X-10) was 51.3 g (90 mmol). When the molecular weight of this polymer was measured by GPC, the weight average molecular weight was 16,800 in terms of polystyrene.

In the obtained polymer (A-4), the introduction amount of the alkyl group in which a part or all of hydrogen atoms is/are substituted with a fluorine atom(s) at the substituent terminal was 0.026 mol with respect to 100 g of the polymer.

[Synthesis Example 16] Synthesis of Polyimide Precursor Polymer (A-5)

The following polyimide precursor polymer (A-5) was obtained in the same manner as in Synthesis Example 12 except that 41.1 g of (X-1) and 28.5 g of (X-10) were changed to 33.3 g (50 mmol) of (X-2) and 28.5 g (50 mmol) of (X-10). When the molecular weight of this polymer was measured by GPC, the weight average molecular weight was 14,400 in terms of polystyrene.

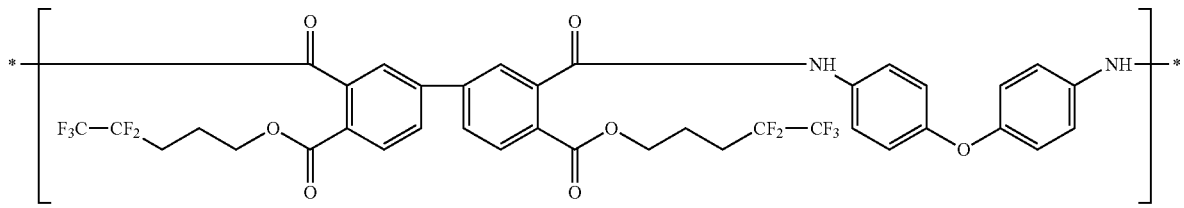

In the obtained polymer (A-5), the introduction amount of the alkyl group in which a part or all of hydrogen atoms is/are substituted with a fluorine atom(s) at the substituent terminal was 0.13 mol with respect to 100 g of the polymer.

[Synthesis Example 17] Synthesis of Polyimide Precursor Polymer (A-6)

A polyimide precursor polymer (A-6) was obtained in the same manner as in Synthesis Example 16 except that (X-2) was 20.0 g (30 mmol), and (X-10) was 39.9 g (70 mmol). When the molecular weight of this polymer was measured by GPC, the weight average molecular weight was 15,300 in terms of polystyrene.

In the obtained polymer (A-6), the introduction amount of the alkyl group in which a part or all of hydrogen atoms is/are substituted with a fluorine atom(s) at the substituent terminal was 0.079 mol with respect to 100 g of the polymer.

[Synthesis Example 18] Synthesis of Polyimide Precursor Polymer (A-7)

A polyimide precursor polymer (A-7) was obtained in the same manner as in Synthesis Example 16 except that (X-2) was 13.3 g (20 mmol), and (X-10) was 45.6 g (80 mmol). When the molecular weight of this polymer was measured by GPC, the weight average molecular weight was 14,900 in terms of polystyrene.

In the obtained polymer (A-7), the introduction amount of the alkyl group in which a part or all of hydrogen atoms is/are substituted with a fluorine atom(s) at the substituent terminal was 0.053 mol with respect to 100 g of the polymer.

[Synthesis Example 19] Synthesis of Polyimide Precursor Polymer (A-8)

A polyimide precursor polymer (A-8) was obtained in the same manner as in Synthesis Example 16 except that (X-2)

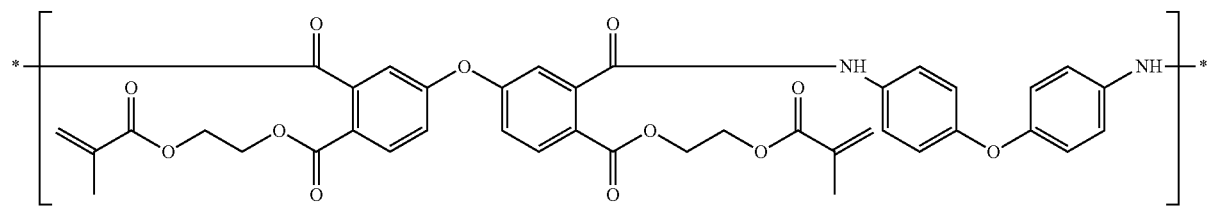

was 6.7 g (10 mmol), and (X-10) was 51.3 g (90 mmol). When the molecular weight of this polymer was measured by GPC, the weight average molecular weight was 15,500 in terms of polystyrene.

In the obtained polymer (A-8), the introduction amount of the alkyl group in which a part or all of hydrogen atoms is/are substituted with a fluorine atom(s) at the substituent terminal was 0.027 mol with respect to 100 g of the polymer.

[Synthesis Example 20] Synthesis of Polyimide Precursor Polymer (A-9)

The following polyimide precursor polymer (A-9) was obtained in the same manner as in Synthesis Example 16 except that 33.3 g of (X-2) and 28.5 g of (X-10) were changed to 23.0 g (30 mmol) of (X-3) and 39.9 g (70 mmol) of (X-10). When the molecular weight of this polymer was measured by GPC, the weight average molecular weight was 14,700 in terms of polystyrene.

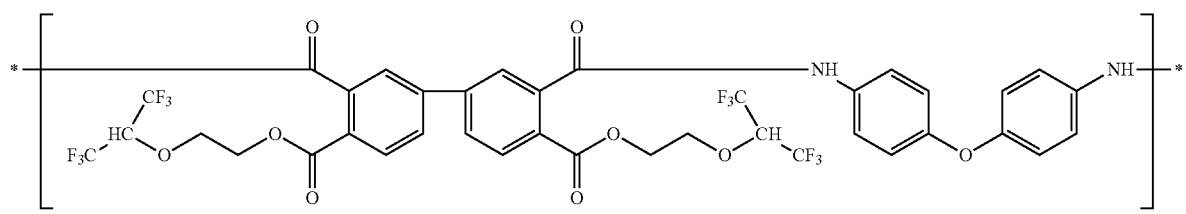

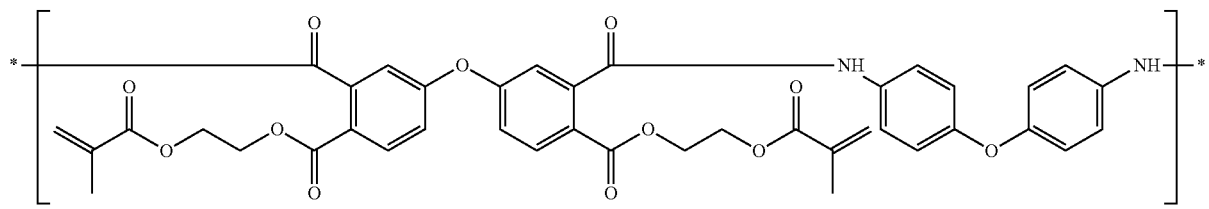

In the obtained polymer (A-9), the introduction amount of the alkyl group in which a part or all of hydrogen atoms is/are substituted with a fluorine atom(s) at the substituent terminal was 0.076 mol with respect to 100 g of the polymer.

[Synthesis Example 21] Synthesis of Polyimide Precursor Polymer (A-10)

The following polyimide precursor polymer (A-10) was obtained in the same manner as in Synthesis Example 16 except that 33.3 g of (X-2) and 28.5 g of (X-10) were changed to 18.3 g (30 mmol) of (X-4) and 39.9 g (70 mmol) of (X-10). When the molecular weight of this polymer was measured by GPC, the weight average molecular weight was 14,000 in terms of polystyrene.

In the obtained polymer (A-10), the introduction amount of the alkyl group in which a part or all of hydrogen atoms is/are substituted with a fluorine atom(s) at the substituent terminal was 0.080 mol with respect to 100 g of the polymer.

[Synthesis Example 22] Synthesis of Polyimide Precursor Polymer (A-11)

The following polyimide precursor polymer (A-11) was obtained in the same manner as in Synthesis Example 16 except that 33.3 g of (X-2) and 28.5 g of (X-10) were changed to 19.2 g (30 mmol) of (X-5) and 39.9 g (70 mmol) of (X-10). When the molecular weight of this polymer was measured by GPC, the weight average molecular weight was 14,400 in terms of polystyrene.

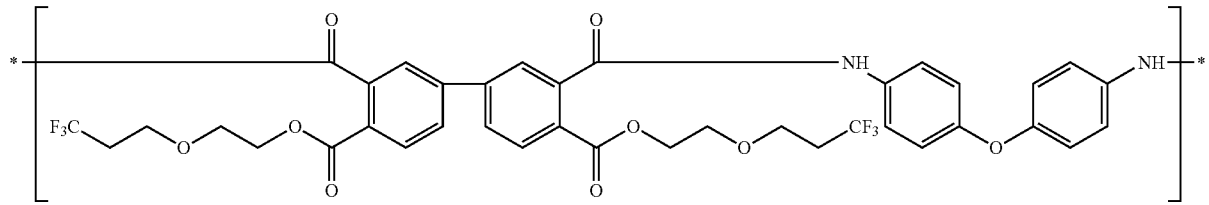

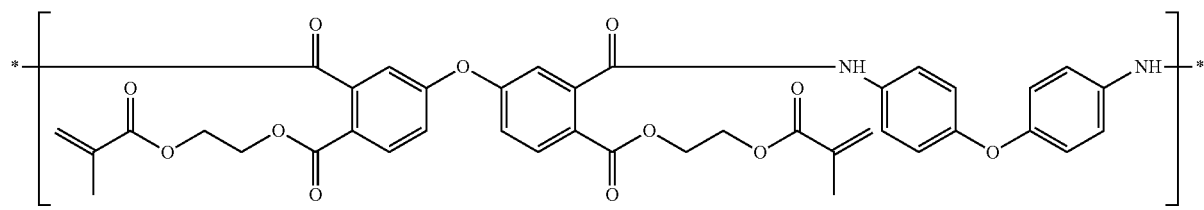

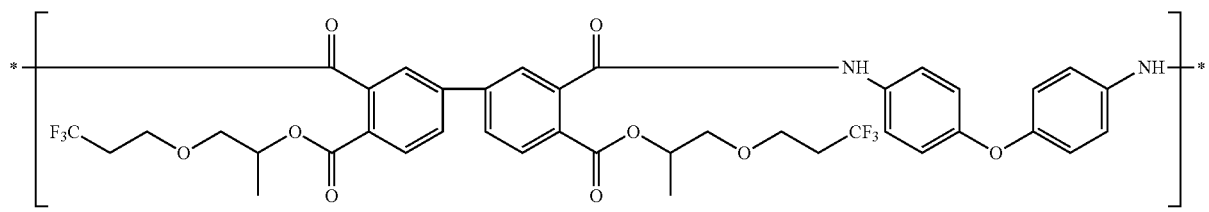

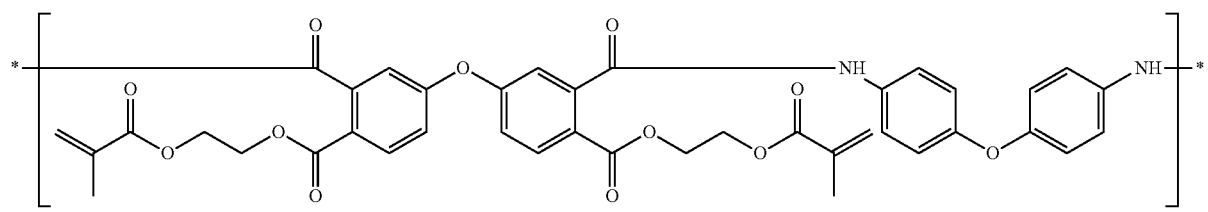

In the obtained polymer (A-11), the introduction amount of the alkyl group in which a part or all of hydrogen atoms is/are substituted with a fluorine atom(s) at the substituent terminal was 0.080 mol with respect to 100 g of the polymer.

[Synthesis Example 23] Synthesis of Polyimide Precursor Polymer (A-12)

The following polyimide precursor polymer (A-12) was obtained in the same manner as in Synthesis Example 16 except that 33.3 g of (X-2) and 28.5 g of (X-10) were changed to 18.3 g (30 mmol) of (X-6) and 39.9 g (70 mmol) of (X-10). When the molecular weight of this polymer was measured by GPC, the weight average molecular weight was 16,400 in terms of polystyrene.

In the obtained polymer (A-12), the introduction amount of the alkyl group in which a part or all of hydrogen atoms is/are substituted with a fluorine atom(s) at the substituent terminal was 0.080 mol with respect to 100 g of the polymer.

[Synthesis Example 24] Synthesis of Polyimide Precursor Polymer (A-13)

The following polyimide precursor polymer (A-13) was obtained in the same manner as in Synthesis Example 16 except that 33.3 g of (X-2) and 28.5 g of (X-10) were changed to 21.3 g (30 mmol) of (X-7) and 39.9 g (70 mmol) of (X-10). When the molecular weight of this polymer was measured by GPC, the weight average molecular weight was 17,300 in terms of polystyrene.

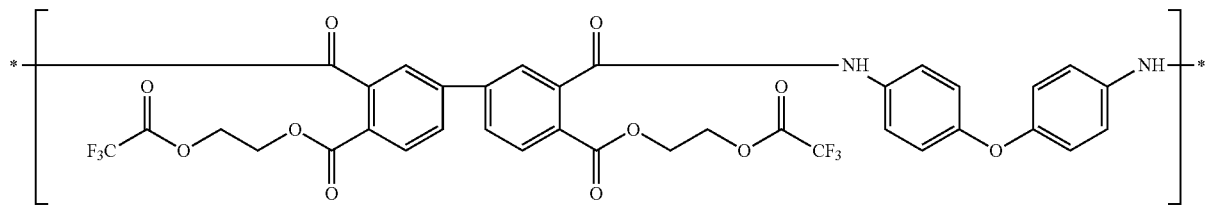

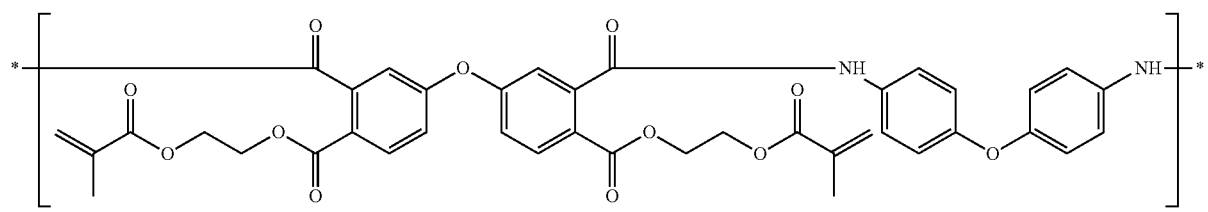

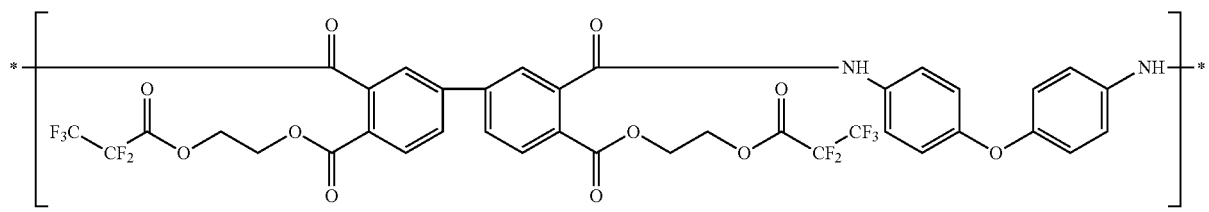

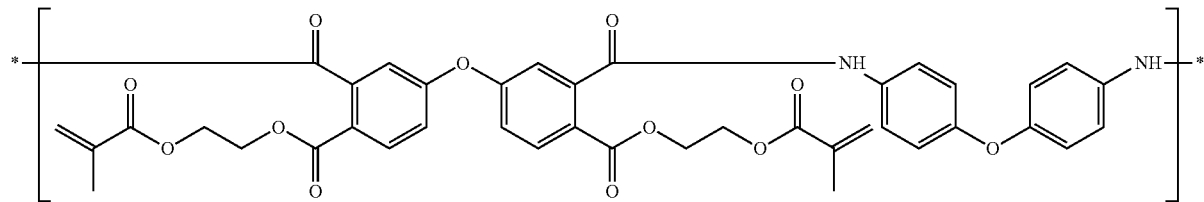

In the obtained polymer (A-13), the introduction amount of the alkyl group in which a part or all of hydrogen atoms is/are substituted with a fluorine atom(s) at the substituent terminal was 0.077 mol with respect to 100 g of the polymer.

[Synthesis Example 25] Synthesis of Polyimide Precursor Polymer (A-14)

The following polyimide precursor polymer (A-14) was obtained in the same manner as in Synthesis Example 16 except that 33.3 g of (X-2) and 28.5 g of (X-10) were changed to 20.8 g (30 mmol) of (X-8) and 39.9 g (70 mmol) of (X-10). When the molecular weight of this polymer was measured by GPC, the weight average molecular weight was 17,600 in terms of polystyrene.

In the obtained polymer (A-14), the introduction amount of the alkyl group in which a part or all of hydrogen atoms is/are substituted with a fluorine atom(s) at the substituent terminal was 0.078 mol with respect to 100 g of the polymer.

[Synthesis Example 26] Synthesis of Polyimide Precursor Polymer (A-15)

The following polyimide precursor polymer (A-15) was obtained in the same manner as in Synthesis Example 16 except that 33.3 g of (X-2) and 28.5 g of (X-10) were changed to 26.5 g (30 mmol) of (X-9) and 39.9 g (70 mmol) of (X-10). When the molecular weight of this polymer was measured by GPC, the weight average molecular weight was 18,600 in terms of polystyrene.

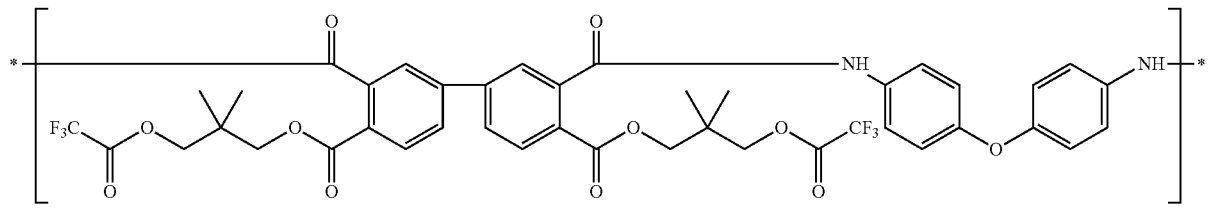

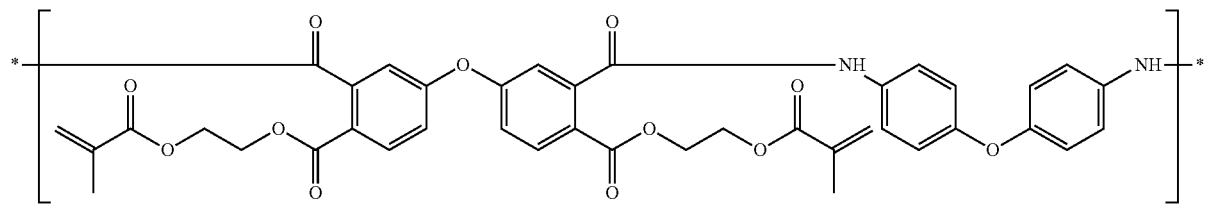

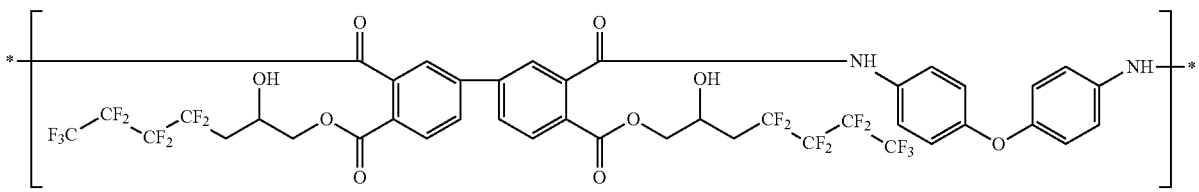

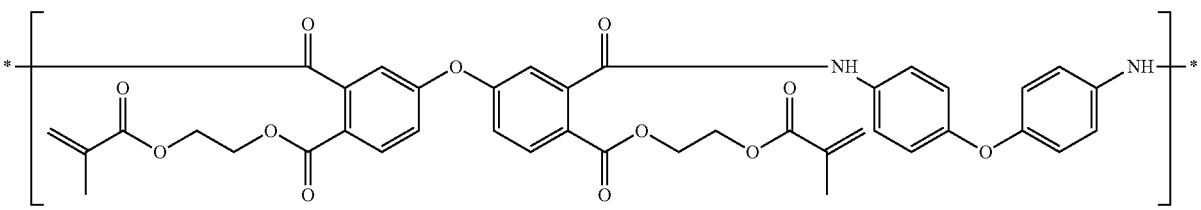

In the obtained polymer (A-15), the introduction amount of the alkyl group in which a part or all of hydrogen atoms is/are substituted with a fluorine atom(s) at the substituent terminal was 0.072 mol with respect to 100 g of the polymer.

[Synthesis Example 27] Synthesis of Polyimide Precursor Polymer (A-16)

The following polyimide precursor polymer (A-16) was obtained in the same manner as in Synthesis Example 12 except that ODA was changed to 27.7 g (95 mmol) of APB. When the molecular weight of this polymer was measured by GPC, the weight average molecular weight was 16,100 in terms of polystyrene.

In the obtained polymer (A-16), the introduction amount of the alkyl group in which a part or all of hydrogen atoms is/are substituted with a fluorine atom(s) at the substituent terminal was 0.067 mol with respect to 100 g of the polymer.

[Synthesis Example 28] Synthesis of Polyimide Precursor Polymer (A-17)

The following polyimide precursor polymer (A-17) was obtained in the same manner as in Synthesis Example 16 except that ODA was changed to 27.7 g (95 mmol) of APB. When the molecular weight of this polymer was measured by GPC, the weight average molecular weight was 16,500 in terms of polystyrene.

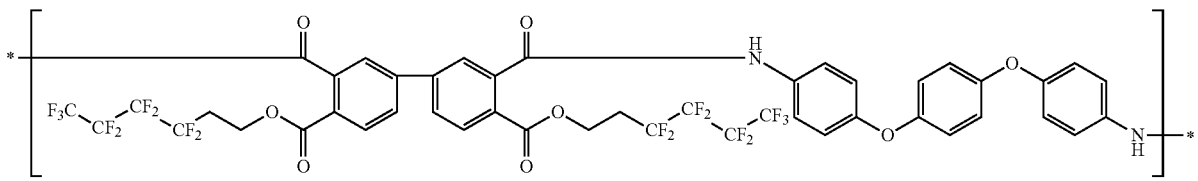

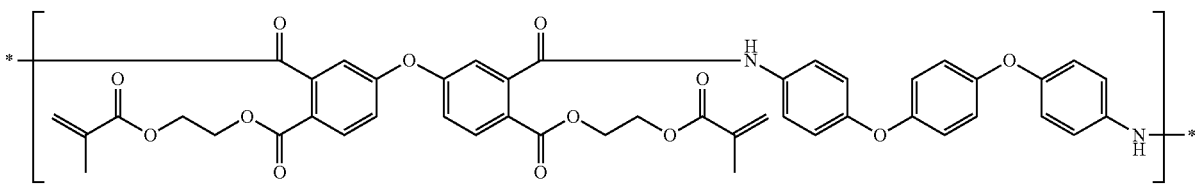

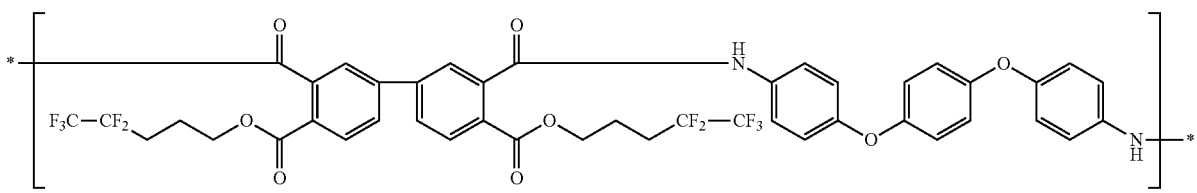

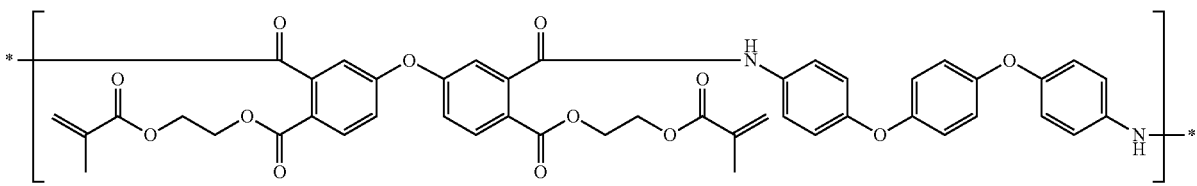

In the obtained polymer (A-17), the introduction amount of the alkyl group in which a part or all of hydrogen atoms is/are substituted with a fluorine atom(s) at the substituent terminal was 0.070 mol with respect to 100 g of the polymer.

[Synthesis Example 29] Synthesis of Polyimide Precursor Polymer (A-18)

The following polyimide precursor polymer (A-18) was obtained in the same manner as in Synthesis Example 21 except that ODA was changed to 27.7 g (95 mmol) of APB. When the molecular weight of this polymer was measured by GPC, the weight average molecular weight was 16,700 in terms of polystyrene.

[Comparative Synthesis Example 1] Synthesis of Polyimide Precursor Polymer (A-19)

The following polyimide precursor polymer (A-19) having neither an alkyl group nor an aromatic group in which a part or all of hydrogen atoms is/are substituted with a fluorine atom(s) at a substituent terminal was obtained in the same manner as in Synthesis Example 12 except that no (X-1), which is a tetracarboxylic acid diester compound having a substituent terminal incorporated with an alkyl group in which a part or all of hydrogen atoms is/are

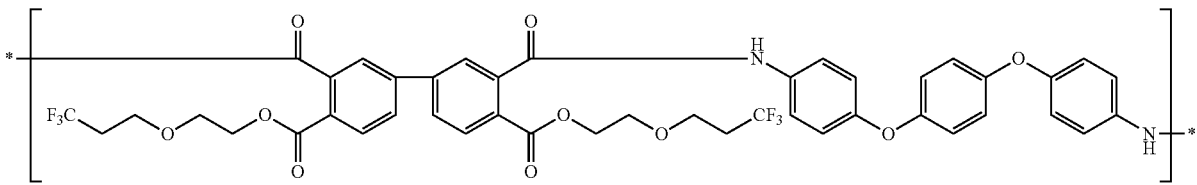

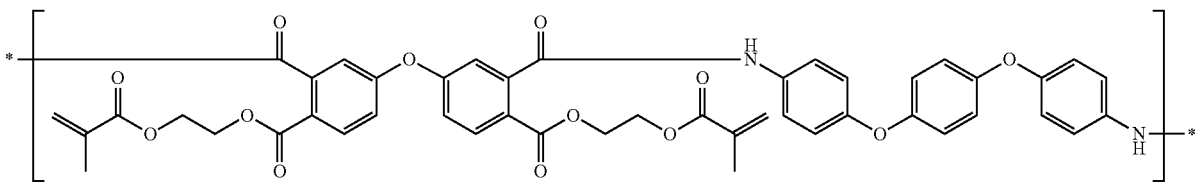

In the obtained polymer (A-18), the introduction amount of the alkyl group in which a part or all of hydrogen atoms is/are substituted with a fluorine atom(s) at the substituent terminal was 0.072 mol with respect to 100 g of the polymer.

substituted with a fluorine atom(s), was used, and (X-10) was 57.1 g (100 mmol). When the molecular weight of this polymer was measured by GPC, the weight average molecular weight was 15,400 in terms of polystyrene.

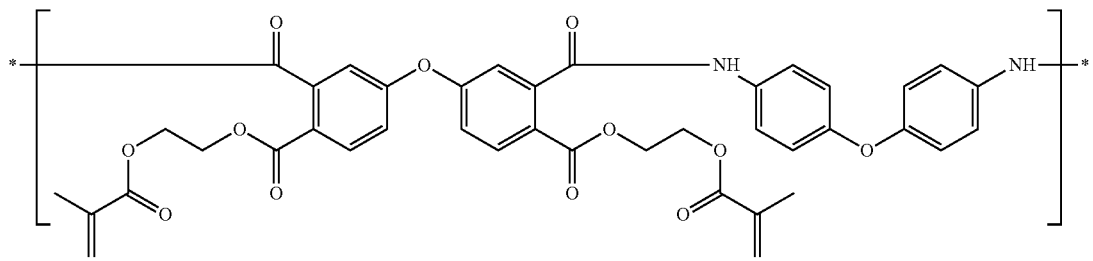

[Comparative Synthesis Example 2] Synthesis of Polyimide Precursor Polymer (A-20)

The following polyimide precursor polymer (A-20) having neither an alkyl group nor an aromatic group in which a part or all of hydrogen atoms is/are substituted with a fluorine atom(s) at a substituent terminal was obtained in the same manner as in Synthesis Example 12 except that no (X-1), which is a tetracarboxylic acid diester compound having a substituent terminal incorporated with an alkyl group in which a part or all of hydrogen atoms is/are substituted with a fluorine atom(s), was used, and 55.5 g (100 mmol) of (X-11) was used instead of (X-10). When the molecular weight of this polymer was measured by GPC, the weight average molecular weight was 13,800 in terms of polystyrene.

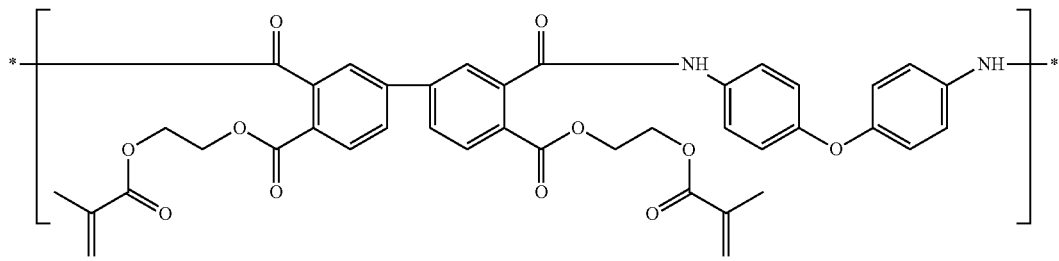

[Comparative Synthesis Example 3] Synthesis of Polyimide Precursor Polymer (A-21)

The following polyimide precursor polymer (A-21) was obtained in the same manner as in Comparative Synthesis Example 1 except that ODA was changed to 27.7 g (95 mmol) of APB. When the molecular weight of this polymer was measured by GPC, the weight average molecular weight was 15,500 in terms of polystyrene.

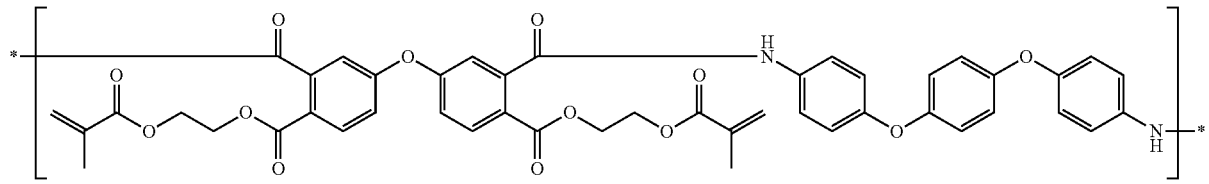

[Comparative Synthesis Example 4] Synthesis of Polyimide Precursor Polymer (A-22)

The following polyimide precursor polymer (A-22) was obtained in the same manner as in Comparative Synthesis Example 2 except that ODA was changed to 27.7 g (95 mmol) of APB. When the molecular weight of this polymer was measured by GPC, the weight average molecular weight was 14,700 in terms of polystyrene.

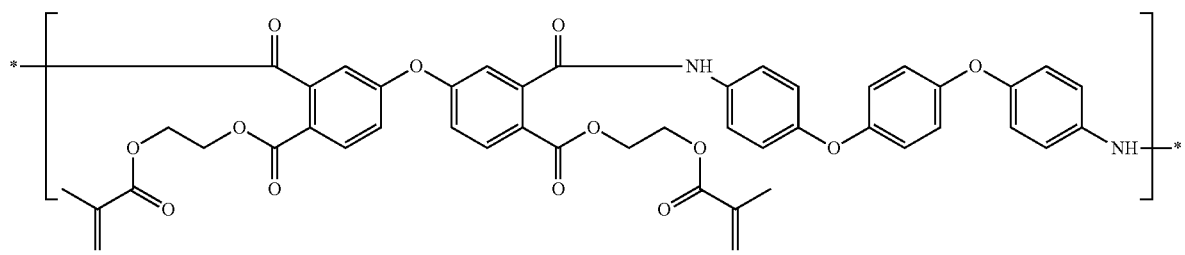

II. Preparation of Negative Photosensitive Resin Composition

The polymers synthesized in Synthesis Examples 12 to 29 and Comparative Synthesis Examples 1 to 4 were used to prepare resin compositions each containing 40 mass % of the resin, with the composition and the formulation amount shown in Tables 1 to 10. Then, the resin compositions were each stirred, mixed, dissolved, and filtered through a 1.0-μm filter made of Teflon® for microfiltration to obtain negative photosensitive resin compositions.

TABLE 1

|  | Negative photosensitive resin composition 1 | Negative photosensitive resin composition 2 | Negative photosensitive resin composition 3 | Negative photosensitive resin composition 4 |
| --- | --- | --- | --- | --- |
| Base resin | A-3 100 parts by mass | A-4 100 parts by mass | A-7 100 parts by mass | A-8 100 parts by mass |
| Photo-radical initiator | Photo-radical initiator 1 2 parts by mass | Photo-radical initiator 1 2 parts by mass | Photo-radical initiator 1 2 parts by mass | Photo-radical initiator 1 2 parts by mass |
| Crosslinking agent | — | — | — | — |
| Solvent | NMP 150 parts by mass | NMP 150 parts by mass | NMP 150 parts by mass | NMP 150 parts by mass |

Photosensitive resin compositions 1 to 4 shown in Table 1 relate to the negative photosensitive resin composition according to the first embodiment of the present invention.

TABLE 2

|  | Comparative negative photosensitive resin composition 1 | Comparative negative photosensitive resin composition 2 | Comparative negative photosensitive resin composition 3 | Comparative negative photosensitive resin composition 4 |
| --- | --- | --- | --- | --- |
| Base resin | A-19 100 parts by mass | A-20 100 parts by mass | A-21 100 parts by mass | A-22 100 parts by mass |
| Photo-radical initiator | Photo-radical initiator 1 2 parts by mass | Photo-radical initiator 1 2 parts by mass | Photo-radical initiator 1 2 parts by mass | Photo-radical initiator 1 2 parts by mass |
| Crosslinking agent | — | — | — | — |
| Solvent | NMP 150 parts by mass | NMP 150 parts by mass | NMP 150 parts by mass | NMP 150 parts by mass |

Comparative negative photosensitive resin compositions 1 to 4 shown in Table 2 use the polyimide precursor polymers synthesized in Comparative Synthesis Examples 1 to 4 as the base resin, in place of the inventive polyimide precursor polymer in the negative photosensitive resin compositions according to the first embodiment of the present invention.

TABLE 3

|  | Negative photosensitive resin composition 5 | Negative photosensitive resin composition 6 | Negative photosensitive resin composition 7 | Negative photosensitive resin composition 8 |
|---|---|---|---|---|
| Base resin | A-1 100 parts by mass | A-2 100 parts by mass | A-5 100 parts by mass | A-6 100 parts by mass |
| Photo-radical initiator | Photo-radical initiator 1 2 parts by mass | Photo-radical initiator 1 2 parts by mass | Photo-radical initiator 1 2 parts by mass | Photo-radical initiator 1 2 parts by mass |
| Crosslinking agent | CL-1 15 parts by mass | CL-1 15 parts by mass | CL-1 15 parts by mass | CL-1 15 parts by mass |
| Solvent | NMP 150 parts by mass | NMP 150 parts by mass | NMP 150 parts by mass | NMP 150 parts by mass |

TABLE 4

|  | Negative photosensitive resin composition 9 | Negative photosensitive resin composition 10 | Negative photosensitive resin composition 11 | Negative photosensitive resin composition 12 |
|---|---|---|---|---|
| Base resin | A-9 100 parts by mass | A-10 100 parts by mass | A-11 100 parts by mass | A-12 100 parts by mass |
| Photo-radical initiator | Photo-radical initiator 1 2 parts by mass | Photo-radical initiator 1 2 parts by mass | Photo-radical initiator 1 2 parts by mass | Photo-radical initiator 1 2 parts by mass |
| Crosslinking agent | CL-1 15 parts by mass | CL-1 15 parts by mass | CL-1 15 parts by mass | CL-1 15 parts by mass |
| Solvent | NMP 150 parts by mass | NMP 150 parts by mass | NMP 150 parts by mass | NMP 150 parts by mass |

TABLE 5

|  | Negative photosensitive resin composition 13 | Negative photosensitive resin composition 14 | Negative photosensitive resin composition 15 | Negative photosensitive resin composition 16 |
|---|---|---|---|---|
| Base resin | A-13 100 parts by mass | A-14 100 parts by mass | A-15 100 parts by mass | A-16 100 parts by mass |
| Photo-radical initiator | Photo-radical initiator 1 2 parts by mass | Photo-radical initiator 1 2 parts by mass | Photo-radical initiator 1 2 parts by mass | Photo-radical initiator 1 2 parts by mass |
| Crosslinking agent | CL-1 15 parts by mass | CL-1 15 parts by mass | CL-1 15 parts by mass | CL-1 15 parts by mass |
| Solvent | NMP 150 parts by mass | NMP 150 parts by mass | NMP 150 parts by mass | NMP 150 parts by mass |

TABLE 6

|  | Negative photosensitive resin composition 17 | Negative photosensitive resin composition 18 |
|---|---|---|
| Base resin | A-17 100 parts by mass | A-18 100 parts by mass |
| Photo-radical initiator | Photo-radical initiator 1 2 parts by mass | Photo-radical initiator 1 2 parts by mass |
| Crosslinking agent | CL-1 15 parts by mass | CL-1 15 parts by mass |
| Solvent | NMP 150 parts by mass | NMP 150 parts by mass |

Photosensitive resin compositions 5 to 18 shown in Tables 3 to 6 relate to the negative photosensitive resin composition according to the second embodiment of the present invention.

TABLE 7

|  | Comparative negative photosensitive resin composition 5 | Comparative negative photosensitive resin composition 6 | Comparative negative photosensitive resin composition 7 | Comparative negative photosensitive resin composition 8 |
| --- | --- | --- | --- | --- |
| Base resin | A-19 100 parts by mass | A-20 100 parts by mass | A-21 100 parts by mass | A-22 100 parts by mass |
| Photo-radical initiator | Photo-radical initiator 1 2 parts by mass | Photo-radical initiator 1 2 parts by mass | Photo-radical initiator 1 2 parts by mass | Photo-radical initiator 1 2 parts by mass |
| Crosslinking agent | CL-1 15 parts by mass | CL-1 15 parts by mass | CL-1 15 parts by mass | CL-1 15 parts by mass |
| Solvent | NMP 150 parts by mass | NMP 150 parts by mass | NMP 150 parts by mass | NMP 150 parts by mass |

Comparative negative photosensitive resin compositions 5 to 8 shown in Table 7 use the polyimide precursor polymers synthesized in Comparative Synthesis Examples 1 to 4 as the base resin, in place of the inventive polyimide precursor polymer in the negative photosensitive resin compositions according to the second embodiment of the present invention.

TABLE 8

|  | Negative photosensitive resin composition 19 | Negative photosensitive resin composition 20 | Negative photosensitive resin composition 21 | Negative photosensitive resin composition 22 |
| --- | --- | --- | --- | --- |
| Base resin | A-1 100 parts by mass | A-2 100 parts by mass | A-5 100 parts by mass | A-6 100 parts by mass |
| Photo acid generator | Photo acid generator 1 2 parts by mass | Photo acid generator 1 2 parts by mass | Photo acid generator 1 2 parts by mass | Photo acid generator 1 2 parts by mass |
| Crosslinking agent | CL-2 15 parts by mass | CL-2 15 parts by mass | CL-2 15 parts by mass | CL-2 15 parts by mass |
| Crosslinking agent | CL-3 15 parts by mass | CL-3 15 parts by mass | CL-3 15 parts by mass | CL-3 15 parts by mass |
| Solvent | NMP 150 parts by mass | NMP 150 parts by mass | NMP 150 parts by mass | NMP 150 parts by mass |

TABLE 9

|  | Negative photosensitive resin composition 23 | Negative photosensitive resin composition 24 | Negative photosensitive resin composition 25 |
| --- | --- | --- | --- |
| Base resin | A-16 100 parts by mass | A-17 100 parts by mass | A-18 100 parts by mass |
| Photo acid generator | Photo acid generator 1 2 parts by mass | Photo acid generator 1 2 parts by mass | Photo acid generator 1 2 parts by mass |
| Crosslinking agent | CL-2 15 parts by mass | CL-2 15 parts by mass | CL-2 15 parts by mass |
| Crosslinking agent | CL-3 15 parts by mass | CL-3 15 parts by mass | CL-3 15 parts by mass |
| Solvent | NMP 150 parts by mass | NMP 150 parts by mass | NMP 150 parts by mass |

Photosensitive resin compositions 19 to 25 shown in Tables 8 and 9 relate to the negative photosensitive resin composition according to the third embodiment of the present invention.

TABLE 10

|  | Comparative negative photosensitive resin composition 9 | Comparative negative photosensitive resin composition 10 | Comparative negative photosensitive resin composition 11 | Comparative negative photosensitive resin composition 12 |
| --- | --- | --- | --- | --- |
| Base resin | A-19 100 parts by mass | A-20 100 parts by mass | A-21 100 parts by mass | A-22 100 parts by mass |
| Photo acid generator | Photo acid generator 1 2 parts by mass | Photo acid generator 1 2 parts by mass | Photo acid generator 1 2 parts by mass | Photo acid generator 1 2 parts by mass |
| Crosslinking agent | CL-2 15 parts by mass | CL-2 15 parts by mass | CL-2 15 parts by mass | CL-2 15 parts by mass |
| Crosslinking agent | CL-3 15 parts by mass | CL-3 15 parts by mass | CL-3 15 parts by mass | CL-3 15 parts by mass |
| Solvent | NMP 150 parts by mass | NMP 150 parts by mass | NMP 150 parts by mass | NMP 150 parts by mass |

Comparative negative photosensitive resin compositions 9 to 12 shown in Table 10 use the polyimide precursor polymers synthesized in Comparative Synthesis Examples 1 to 4 as the base resin, in place of the inventive polyimide precursor polymer in the negative photosensitive resin compositions according to the third embodiment of the present invention.

In Tables 1 to 10, the photo-radical initiator (Photo-radical initiator 1), the photo acid generator (Photo acid generator 1), and the crosslinking agents (CL-1) to (CL-3) are as follows.

Photo-radical initiator (Photo-radical initiator 1): NP-1919 manufactured by ADEKA Corp.

Photo acid generator (Photo acid generator 1)

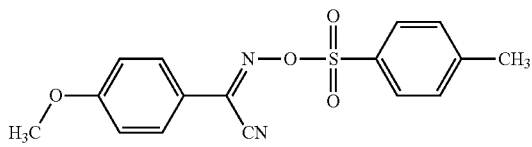

Crosslinking agent (CL-1): ethylene glycol diacrylate
Crosslinking agent (CL-2):

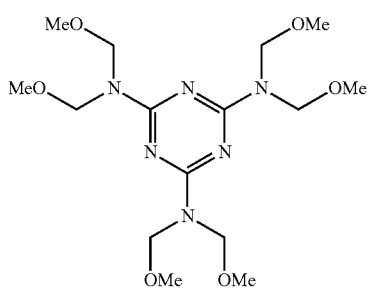 [SMILES: COCN(COC)c1nc(N(COC)COC)nc(N(COC)COC)n1]

Crosslinking agent (CL-3):

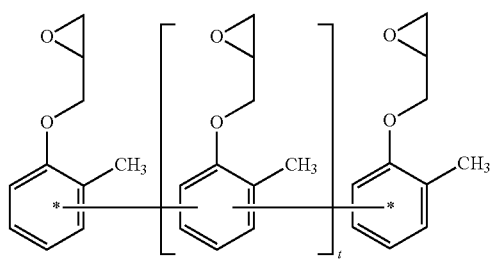

wherein $2 \leq t \leq 3$.

III. Patterning Process 5 mL of Negative photosensitive resin compositions 1 to 25 and Comparative negative photosensitive resin compositions 1 to 12 were each dispensed and applied onto a silicon substrate by rotating the substrate, i.e., by the spin coating method so as to give a film thickness of 10 μm after patterning and baking for post-curing. That is, the rotational speed during applying was adjusted such that a post-cured film had a thickness of 10 μm, in consideration of an expected reduction in film thickness after the post-curing step.

Then, pre-baking was performed on a hot plate at 100° C. for 2 minutes. The film was then exposed to an i-line beam with an i-line stepper, NSR-2205i11, manufactured by Nikon Corporation, to form a pattern. In the pattern formation, a mask for negative pattern was appropriately used according to the used negative photosensitive resin compositions. The mask had a pattern capable of forming 20 μm holes arranged with a 1:1 ratio lengthwise and breadthwise, and permitted to form a hole pattern of 50 μm to 20 μm holes with 10-μm pitch, 20 μm to 10 μm holes with 5-μm pitch, and 10 μm to 1 μm holes with 1-μm pitch.

The post-exposure bake step was not performed in all of the examples, as shown in Tables 11 to 16.

In the development step, cyclopentanone was used as the developer in Examples 1 to 25. On the other hand, NMP was used as the developer for Comparative negative photosensitive resin compositions 1 to 12 prepared for Comparative examples. The organic solvent development was to perform puddling development with the respective organic solvents for 1 minute corresponding times shown in Tables 11 to 16, followed by rinsing with isopropyl alcohol.

The obtained pattern on the substrate was then post-cured with an oven at 250° C. for 2 hours while purging with nitrogen.

Then, each substrate was cut to observe the shape of the obtained hole pattern, and the hole pattern profile was observed with a scanning electron microscope (SEM). A minimum diameter of the opening holes was measured on the post-cured film having a thickness of 10 μm, and the pattern profile was evaluated. Tables 11 to 16 show these results and sensitivity at which a minimum pattern could be formed.

The hole pattern profile was evaluated based on the following criterion. The evaluation results are shown in Tables 11 to 16.

Good: The holes were rectangular or forward tapered (the upper part of the hole is larger than the bottom).

Poor: The holes were reverse tapered (the upper part of the hole is smaller than the bottom), overhanging (the upper part of the hole is protruded), or residues were observed in the hole bottom.

First, Tables 11 and 12 show results of the organic solvent development and patterning using Negative photosensitive resin compositions 1 to 4 (the negative photosensitive resin compositions according to the first embodiment of the present invention) and Comparative negative photosensitive resin compositions 1 to 4.

TABLE 11

|  | Negative photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Example 1 | Negative photosensitive resin composition 1 | Negative | None | (Organic solvent development) cyclopentanone | Puddling 60 sec twice | Good | 8 | 330 |
| Example 2 | Negative photosensitive resin composition 2 | Negative | None | (Organic solvent development) cyclopentanone | Puddling 60 sec twice | Good | 8 | 330 |
| Example 3 | Negative photosensitive resin composition 3 | Negative | None | (Organic solvent development) cyclopentanone | Puddling 60 sec twice | Good | 8 | 340 |
| Example 4 | Negative photosensitive resin composition 4 | Negative | None | (Organic solvent development) cyclopentanone | Puddling 60 sec twice | Good | 8 | 360 |

TABLE 12

|  | Negative photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Comparative Example 1 | Comparative negative photosensitive resin composition 1 | Negative | None | (Organic solvent development) NMP | Puddling 60 sec twice | Poor | 20 | 400 |
| Comparative Example 2 | Comparative negative photosensitive resin composition 2 | Negative | None | (Organic solvent development) NMP | Puddling 60 sec twice | Poor | 20 | 420 |
| Comparative Example 3 | Comparative negative photosensitive resin composition 3 | Negative | None | (Organic solvent development) NMP | Puddling 60 sec twice | Poor | 20 | 400 |
| Comparative Example 4 | Comparative negative photosensitive resin composition 4 | Negative | None | (Organic solvent development) NMP | Puddling 60 sec twice | Poor | 20 | 440 |

Next, Tables 13 and 14 show results of the organic solvent development and patterning using Negative photosensitive resin compositions 5 to 18 (the negative photosensitive resin compositions according to the second embodiment of the present invention) and Comparative negative photosensitive resin compositions 5 to 8.

TABLE 13

| | Negative photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Example 5 | Negative photosensitive resin composition 5 | Negative | None | (Organic solvent development) cyclopentanone | Puddling 60 sec one time | Good | 6 | 330 |
| Example 6 | Negative photosensitive resin composition 6 | Negative | None | (Organic solvent development) cyclopentanone | Puddling 60 sec one time | Good | 7 | 330 |
| Example 7 | Negative photosensitive resin composition 7 | Negative | None | (Organic solvent development) cyclopentanone | Puddling 60 sec one time | Good | 6 | 340 |
| Example 8 | Negative photosensitive resin composition 8 | Negative | None | (Organic solvent development) cyclopentanone | Puddling 60 sec one time | Good | 7 | 360 |
| Example 9 | Negative photosensitive resin composition 9 | Negative | None | (Organic solvent development) cyclopentanone | Puddling 60 sec one time | Good | 8 | 330 |
| Example 10 | Negative photosensitive resin composition 10 | Negative | None | (Organic solvent development) cyclopentanone | Puddling 60 sec one time | Good | 8 | 340 |
| Example 11 | Negative photosensitive resin composition 11 | Negative | None | (Organic solvent development) cyclopentanone | Puddling 60 sec one time | Good | 8 | 360 |
| Example 12 | Negative photosensitive resin composition 12 | Negative | None | (Organic solvent development) cyclopentanone | Puddling 60 sec one time | Good | 8 | 330 |
| Example 13 | Negative photosensitive resin composition 13 | Negative | None | (Organic solvent development) cyclopentanone | Puddling 60 sec one time | Good | 8 | 340 |
| Example 14 | Negative photosensitive resin composition 14 | Negative | None | (Organic solvent development) cyclopentanone | Puddling 60 sec one time | Good | 8 | 360 |
| Example 15 | Negative photosensitive resin composition 15 | Negative | None | (Organic solvent development) cyclopentanone | Puddling 60 sec one time | Good | 8 | 330 |
| Example 16 | Negative photosensitive resin composition 16 | Negative | None | (Organic solvent development) cyclopentanone | Puddling 60 sec one time | Good | 7 | 340 |
| Example 17 | Negative photosensitive resin composition 17 | Negative | None | (Organic solvent development) cyclopentanone | Puddling 60 sec one time | Good | 8 | 360 |
| Example 18 | Negative photosensitive resin composition 18 | Negative | None | (Organic solvent development) cyclopentanone | Puddling 60 sec one time | Good | 7 | 360 |

TABLE 14

| | Negative photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Comparative Example 5 | Comparative negative photosensitive resin composition 5 | Negative | None | (Organic solvent development) NMP | Puddling 60 sec twice | Poor | 20 | 360 |
| Comparative Example 6 | Comparative negative photosensitive resin composition 6 | Negative | None | (Organic solvent development) NMP | Puddling 60 sec twice | Poor | 20 | 380 |
| Comparative Example 7 | Comparative negative photosensitive resin composition 7 | Negative | None | (Organic solvent development) NMP | Puddling 60 sec twice | Poor | 20 | 400 |
| Comparative Example 8 | Comparative negative photosensitive resin composition 8 | Negative | None | (Organic solvent development) NMP | Puddling 60 sec twice | Poor | 20 | 400 |

Further, Tables 15 and 16 show results of the organic solvent development and patterning using Negative photosensitive resin compositions 19 to 25 (the negative photosensitive resin compositions according to the third embodiment of the present invention) and Comparative negative photosensitive resin compositions 9 to 12.

TABLE 15

| | Negative photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Example 19 | Negative photosensitive resin composition 19 | Negative | None | (Organic solvent development) cyclopentanone | Puddling 60 sec one time | Good | 7 | 380 |
| Example 20 | Negative photosensitive resin composition 20 | Negative | None | (Organic solvent development) cyclopentanone | Puddling 60 sec one time | Good | 8 | 380 |
| Example 21 | Negative photosensitive resin composition 21 | Negative | None | (Organic solvent development) cyclopentanone | Puddling 60 sec one time | Good | 7 | 400 |
| Example 22 | Negative photosensitive resin composition 22 | Negative | None | (Organic solvent development) cyclopentanone | Puddling 60 sec one time | Good | 7 | 420 |
| Example 23 | Negative photosensitive resin composition 23 | Negative | None | (Organic solvent development) cyclopentanone | Puddling 60 sec one time | Good | 8 | 380 |
| Example 24 | Negative photosensitive resin composition 24 | Negative | None | (Organic solvent development) cyclopentanone | Puddling 60 sec one time | Good | 7 | 380 |
| Example 25 | Negative photosensitive resin composition 25 | Negative | None | (Organic solvent development) cyclopentanone | Puddling 60 sec one time | Good | 7 | 420 |

TABLE 16

| | Negative photosensitive resin composition | Pattern | Post exposure bake | Developer | Development condition | Hole shape | Minimum hole diameter (μm) | Sensitivity (mJ/cm2) |
|---|---|---|---|---|---|---|---|---|
| Comparative Example 9 | Comparative negative photosensitive resin composition 9 | Negative | None | (Organic solvent development) NMP | Puddling 60 sec twice | Poor | 20 | 480 |
| Comparative Example 10 | Comparative negative photosensitive resin composition 10 | Negative | None | (Organic solvent development) NMP | Puddling 60 sec twice | Poor | 20 | 520 |
| Comparative Example 11 | Comparative negative photosensitive resin composition 11 | Negative | None | (Organic solvent development) NMP | Puddling 60 sec twice | Poor | 20 | 540 |
| Comparative Example 12 | Comparative negative photosensitive resin composition 12 | Negative | None | (Organic solvent development) NMP | Puddling 60 sec twice | Poor | 20 | 500 |

As shown in Tables 11, 13, and 15, the inventive negative photosensitive resin composition could give a good pattern profile and a small minimum hole dimension, compared to a final film thickness of 10 μm, in the organic solvent development. It was thus revealed that an aspect ratio of 1 or more could be achieved.

By contrast, in Comparative examples, Comparative negative photosensitive resin compositions 1 to 12, which used the polyimide precursor polymers having neither an alkyl group nor an aromatic group in which a part or all of hydrogen atoms is/are substituted with a fluorine atom(s) at a substituent terminal, could not be used for the organic solvent development with cyclopentanone in patterning because these comparative negative photosensitive resin compositions had base resins that were difficultly soluble or insoluble in cyclopentanone, thus NMP was used for patterning instead.

As shown in Tables 12, 14, and 16, in Comparative examples, Comparative negative photosensitive resin compositions 1 to 12, which used the polyimide precursor polymers having neither an alkyl group nor an aromatic group in which a part or all of hydrogen atoms is/are substituted with a fluorine atom(s) at a substituent terminal, could form a pattern by using NMP. However, the pattern dimension was large, and an aspect ratio of 1 or more could not be achieved. In addition, overhanging profile was observed on many patterns, and thus the pattern profile was poor. The overhanging profile is supposed to be caused by swelling of the pattern during development.

It should be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. A polyimide precursor polymer comprising a structural unit shown by the following general formula (7), and a structural unit shown by the following general formula (8),

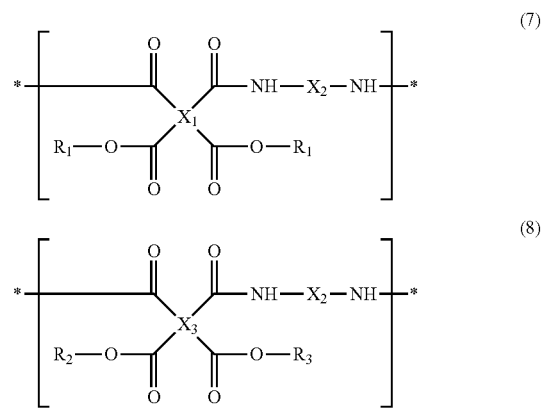

wherein in general formula (7), $X_1$ represents a tetravalent organic group selected from at least one of the following formulae:

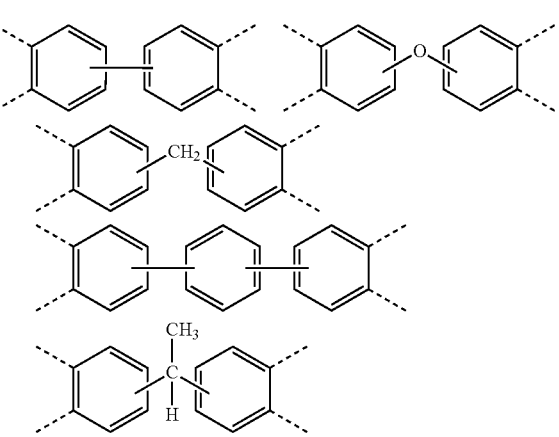

-continued

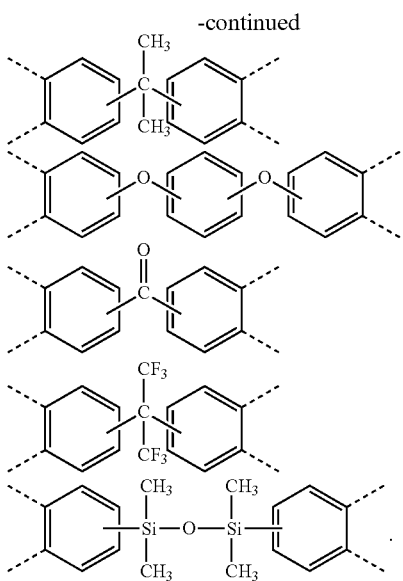

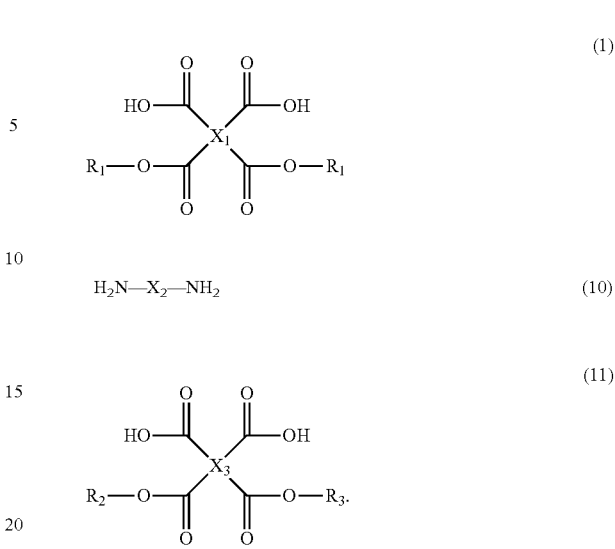

wherein the dotted line represents a bond;
$X_2$ represents a divalent organic group; and $R_1$ represents a group shown by the following general formula (2),

wherein the dotted line represents a bond; $Y_1$ represents an organic group with a valency of k+1; Rf represents a linear, branched, or cyclic alkyl group having 1 to 20 carbon atoms or an aromatic group in which a part or all of hydrogen atoms is/are substituted with a fluorine atom(s), and provided that at least one hydrogen on a terminal carbon is substituted with a fluorine atom; "k" represents 1, 2, or 3; and "n" represents 0 or 1, and wherein in general formula (8), $X_3$ represents a tetravalent organic group that is the same as or different from $X_1$; and $R_2$ and $R_3$ independently represent a hydrogen atom, a linear, branched, or cyclic alkyl group having 1 to 6 carbon atoms, or an organic group shown by the following general formula (9), provided that at least one of $R_2$ and $R_3$ is an organic group shown by the general formula (9),

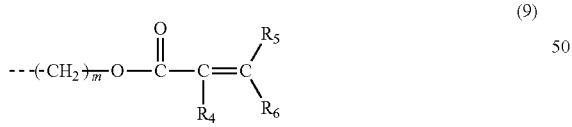

wherein the dotted line represents a bond; $R_4$ represents a hydrogen atom or an organic group having 1 to 3 carbon atoms; $R_5$ and $R_6$ independently represent a hydrogen atom or an organic group having 1 to 3 carbon atoms; and "m" represents an integer of 2 to 10.

2. A method for producing the polyimide precursor polymer according to claim 1, comprising
reacting a tetracarboxylic acid diester compound shown by the following general formula (1) with a diamine shown by the following general formula (10) and a tetracarboxylic acid diester compound shown by the following general formula (11), 3. A negative photosensitive resin composition comprising:
(A) the polyimide precursor polymer according to claim 1;
(B) a photo-radical initiator; and
(D) a solvent.

4. A patterning process comprising:
(1) applying the negative photosensitive resin composition according to claim 3 onto a substrate to form a photosensitive material film;
(2) exposing the photosensitive material film to a high energy beam having a wavelength of 190 to 500 nm or an electron beam via a photomask after a heat treatment; and
(3) performing development with a developer of an organic solvent.

5. The patterning process according to claim 4, further comprising performing post-exposure bake between the exposing step and the development step.

6. A method for forming a cured film, comprising baking a film having a pattern formed by the patterning process according to claims 4 at 100 to 300° C. and post-curing the film.

7. A negative photosensitive resin composition comprising:
(A') the polyimide precursor polymer according to claim 1;
(B) a photo-radical initiator;
(C) a crosslinking agent having two or more photopolymerizable unsaturated linking groups per molecule; and
(D) a solvent.

8. A negative photosensitive resin composition comprising:
(A') the polyimide precursor polymer according to claim 1;
(B') a photo acid generator;
(C') one or two or more crosslinking agents selected from an amino condensate modified with formaldehyde or formaldehyde-alcohol, a phenol compound having on average two or more methylol groups or alkoxymethylol groups per molecule, a polyhydric phenol compound in which a hydrogen atom of a phenolic hydroxyl group is substituted with a glycidyl group, a polyhydric phenol compound in which a hydrogen atom of a phenolic hydroxyl group is substituted with a substituent shown by the following formula (C-1), and a compound containing two or more nitrogen atoms having a glycidyl group as shown by the following formula (C-2),

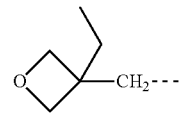
(C-1)

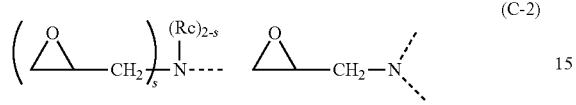
(C-2)

wherein the dotted line represents a bond, Rc represents a linear, branched, or cyclic alkyl group having 1 to 6 carbon atoms, and "s" represents 1 or 2; and (D) a solvent.

* * * * *